United States Patent
Lee

(10) Patent No.: US 10,074,812 B2
(45) Date of Patent: Sep. 11, 2018

(54) COMPOUND AND ORGANIC LIGHT-EMITTING DEVICE INCLUDING THE SAME

(71) Applicant: Samsung Display Co., Ltd., Yongin-si, Gyeonggi-do (KR)

(72) Inventor: Jungsub Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 137 days.

(21) Appl. No.: 15/296,852

(22) Filed: Oct. 18, 2016

(65) Prior Publication Data
US 2017/0271596 A1    Sep. 21, 2017

(30) Foreign Application Priority Data
Mar. 18, 2016  (KR) .......... 10-2016-0032908

(51) Int. Cl.
*H01L 51/00* (2006.01)
*C07D 471/06* (2006.01)
(Continued)

(52) U.S. Cl.
CPC ........ *H01L 51/0072* (2013.01); *C07D 401/04* (2013.01); *C07D 401/10* (2013.01);
(Continued)

(58) Field of Classification Search
CPC .. C07D 401/04; C07D 401/10; C07D 401/14; C07D 471/06; C07D 491/06;
(Continued)

(56) References Cited

U.S. PATENT DOCUMENTS

2013/0043463 A1*  2/2013  Yamada ............... C07C 13/62
                                                                257/40
2015/0060791 A1   3/2015  Shin et al.
(Continued)

FOREIGN PATENT DOCUMENTS

KR   10-2011-0088118 A   8/2011
KR   10-2011-0116635 A   10/2011
(Continued)

OTHER PUBLICATIONS

Machine translation for KR 10-2015-0012835 A (Publication date: Feb. 2015).*
(Continued)

*Primary Examiner* — Dawn Garrett
(74) *Attorney, Agent, or Firm* — Lewis Roca Rothgerber Christie LLP

(57) ABSTRACT

A compound is represented by one selected from Formulae 1 and 2:

Formula 1

(Continued)

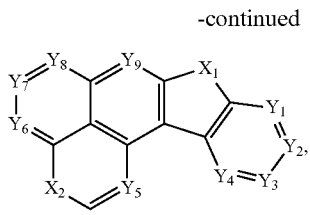

Formula 2

Wherein the components of Formulae 1 and 2 are each independently defined as set forth in the present disclosure. An organic light-emitting device includes at least one of the compound represented by one selected from Formulae 1 and 2.

23 Claims, 5 Drawing Sheets

(51) Int. Cl.
| | | |
|---|---|---|
| C07D 401/10 | (2006.01) | |
| C07D 491/06 | (2006.01) | |
| C07D 495/06 | (2006.01) | |
| H01L 51/50 | (2006.01) | |
| C07D 519/00 | (2006.01) | |
| C09K 11/06 | (2006.01) | |
| C07D 401/04 | (2006.01) | |
| C07D 401/14 | (2006.01) | |

(52) U.S. Cl.
CPC ......... *C07D 401/14* (2013.01); *C07D 471/06* (2013.01); *C07D 491/06* (2013.01); *C07D 495/06* (2013.01); *C07D 519/00* (2013.01); *C09K 11/06* (2013.01); *H01L 51/005* (2013.01); *H01L 51/0067* (2013.01); *H01L 51/0071* (2013.01); *H01L 51/0077* (2013.01); *H01L 51/0081* (2013.01); *H01L 51/506* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC ... C07D 495/06; C07D 519/00; H01L 51/005; H01L 51/0067; H01L 51/0071; H01L 51/0072; H01L 51/0077; H01L 51/0081; H01L 51/5016; H01L 51/5056; H01L 51/506; H01L 51/5072; H01L 51/5088; H01L 51/5092; H01L 51/5096
See application file for complete search history.

(56) References Cited

U.S. PATENT DOCUMENTS

| | | |
|---|---|---|
| 2015/0263293 A1 | 9/2015 | Hwang et al. |
| 2016/0079546 A1 | 3/2016 | Park et al. |

FOREIGN PATENT DOCUMENTS

| | | | |
|---|---|---|---|
| KR | 10-2011-0134581 A | | 12/2011 |
| KR | 10-2012-0030941 A | | 3/2012 |
| KR | 10-2013-0076842 A | | 7/2013 |
| KR | 10-2015-0012835 A | * | 2/2015 |
| KR | 10-2015-0065383 A | | 6/2015 |
| WO | WO 2011/093609 A1 | | 8/2011 |
| WO | WO 2011/132866 A1 | | 10/2011 |
| WO | WO 2014/092354 A1 | | 6/2014 |

OTHER PUBLICATIONS

Partial English translation of relevant parts of WO 2014/092354 A1 dated Jun. 19 2014, listed above (1 page).
EPO Extended Search Report dated Dec. 8, 2016, for corresponding European Patent Application No. 16195530.7 (7 pages).

* cited by examiner

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2016-0032908, filed on Mar. 18, 2016, in the Korean Intellectual Property Office, the entire content of which is incorporated herein by reference.

BACKGROUND

1. Field

One or more embodiments relate to a compound and an organic light-emitting device including the same.

2. Description of the Related Art

Organic light-emitting devices are self-emission devices and have wide viewing angles, high contrast ratios, short response times, and excellent luminance, driving voltage, and response speed characteristics, and produce full-color images.

For example, an organic light-emitting device may include a first electrode on a substrate, and a hole transport region, an emission layer, an electron transport region, and a second electrode, which are sequentially on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. When the excitons drop (e.g., transition) from an excited state to a ground state, light is emitted.

SUMMARY

One or more embodiments include a material for forming an electron transport region and an organic light-emitting device including the material and accordingly having improved characteristics.

Additional aspects of embodiments will be set forth in part in the description which follows and, in part, will be apparent from the description, or may be learned by practice of the presented embodiments.

According to one or more embodiments, a compound may be represented by one selected from Formulae 1 and 2:

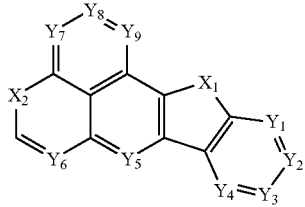

Formula 1

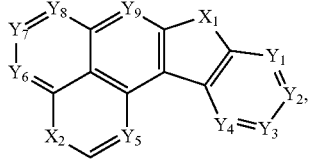

Formula 2 wherein, in Formulae 1 and 2, $X_1$ and $X_2$ may each independently be selected from O, S, $N(Ar_1)$, and $C(Ar_2)(Ar_3)$, provided that $X_1$ and $X_2$ may each be different from or identical to each other and at least one selected from $X_1$ and $X_2$ may be $N(Ar_1)$, $Y_1$ to $Y_9$ may each independently be N or $C(R_1)$, provided that $Y_1$ to $Y_9$ may each be different from or identical to each other, and a plurality of $R_1$s may be different from or identical to each other when $R_1$ is plural in number (e.g., when more than one selected from $Y_1$ to $Y_9$ is $C(R_1)$, the $R_1$ groups of the plurality of $C(R_1)$ may be different from or identical to each other), $Ar_1$ to $Ar_3$ and $R_1$ may each independently be selected from hydrogen, deuterium, halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$, and $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more embodiments, an organic light-emitting includes: a first electrode, a second electrode facing the first electrode, and an organic layer between the first electrode and the second electrode and including an emission layer, the organic layer including the compound represented by one selected from Formulae 1 and 2.

According to one or more embodiments, a display device includes the organic light-emitting device, wherein the first electrode of the organic light-emitting device is electrically coupled with a source electrode or a drain electrode of a thin film transistor.

BRIEF DESCRIPTION OF THE DRAWINGS

These and/or other aspects of embodiments will become apparent and more readily appreciated from the following description of the embodiments, taken in conjunction with the accompanying drawings in which.

DETAILED DESCRIPTION

Figure 1:
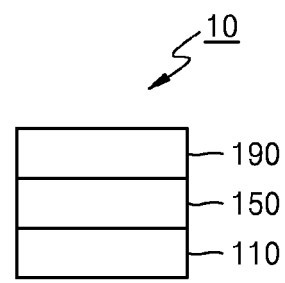
FIG. 1 is a schematic diagram illustrating an organic light-emitting device according to an embodiment.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of an embodiment of the present disclosure, a compound is represented by one selected from Formulae 1 and 2:

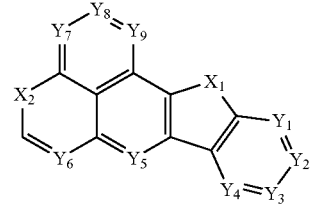

Formula 1

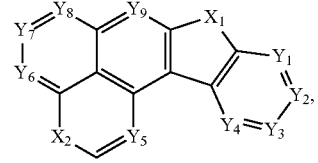

Formula 2 wherein, in Formulae 1 and 2, $X_1$ and $X_2$ may each independently be selected from O, S, $N(Ar_1)$, and $C(Ar_2)(Ar_3)$, provided that $X_1$ and $X_2$ may each be different from or identical to each other and at least one selected from $X_1$ and $X_2$ may be $N(Ar_1)$, $Y_1$ to $Y_9$ may each independently be N or $C(R_1)$, provided that $Y_1$ to $Y_9$ may each be different from or identical to each other, and a plurality of $R_1$s may be different from or identical to each other when $R_1$ is plural in number (e.g., when more than one selected from $Y_1$ to $Y_9$ is $C(R_1)$, the $R_1$ groups of the plurality of $C(R_1)$ may be different from or identical to each other), $Ar_1$ to $Ar_3$ and $R_1$ may each independently be selected from hydrogen, deuterium, halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group (e.g., a hydrazino group), a hydrazone group (e.g., a hydrazono group), a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Early researchers of organic light-emitting devices observed light emission at an organic thin film when a high alternating current voltage was applied to a polymer thin film containing organic pigments. Later, blue fluorescence was obtained through singlet excitons produced by applying a current to anthracene single crystals.

As a method of improving the efficiency of the organic light-emitting device, the research on manufacturing a multi-layered organic layer, instead of a single-layered organic layer, in the organic light-emitting device has been conducted. For example, an organic light-emitting device having a stacked structure including separate functional layers, such as a hole injection layer and an emission layer has been suggested. Accordingly, organic light-emitting devices may have a structure including a substrate, an anode, a hole injection layer that accepts holes provided from the anode, a hole transport layer that transports holes, an emission layer where holes and electrons recombine to emit light, an electron transport layer that transports electrons, an electron injection layer that accepts electrons provided from a cathode, and a cathode. One reason why organic light-emitting devices are manufactured to have multiple layers is that holes and electrons may have a different speed of mobility. Thus, the manufacture of the suitable or appropriate hole injection layer, hole transport layer, electron transport layer, and electron injection layer may allow the holes and electrons to be transported in an efficient manner, and accordingly, there may be good balance between the holes and electrons in the organic light-emitting device, thereby increasing the emission efficiency of the organic light-emitting device.

A quinoline-based hole-transporting (HT) moiety and an electron-transporting (ET) moiety, such as a triazine group, coexist in a host of the materials used in embodiments of the present disclosure, thereby forming an excimer as a hybridized host. The formation of the excimer facilitates energy transfer to a phosphorescent dopant, and accordingly, the organic light-emitting device may have features of improved luminous efficiency and long lifespan.

The substituents of Formulae 1 and 2 will be described in more detail.

In an embodiment, in Formulae 1 and 2, $R_1$ may be hydrogen or deuterium.

In an embodiment, in Formulae 1 and 2, $Ar_2$ and $Ar_3$ may each independently be selected from a substituted or unsubstituted $C_1$-$C_{60}$ alkyl group, a substituted or unsubstituted $C_6$-$C_{60}$ aryl group, and a substituted or unsubstituted $C_1$-$C_{60}$ heteroaryl group.

In an embodiment, in Formulae 1 and 2, at least one $Ar_1$ may be a group represented by one selected from Formulae 2a to 2g:

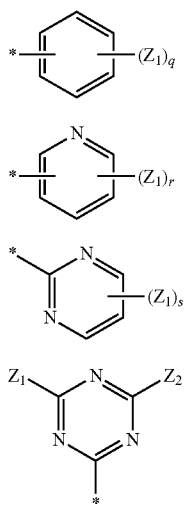

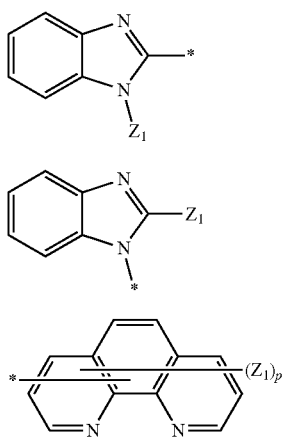

In Formulae 2a to 2g, $Z_1$ and $Z_2$ may each independently be selected from hydrogen, deuterium, halogen, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p may be an integer selected from 1 to 7, q may be an integer selected from 1 to 5, r may be an integer selected from 1 to 4, s may be an integer selected from 1 to 3 and when p, q, r, and/or s is 2 or more, a plurality of $Z_1$(s) may be identical to or different from each other, and

* indicates a binding site.

In an embodiment, Formulae 1 and 2 may be represented by Formulae 3 and 4, respectively:

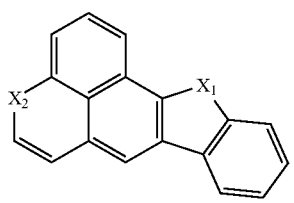

The definitions of substituents of Formulae 3 and 4 are the same as described above. For example, in Formulae 3 and 4, $X_1$ and $X_2$ may be the same as described in connection with Formulae 1 and 2. In some embodiments, at least one $Ar_1$ may be a group represented by one selected from Formulae 2a to 2g.

In some embodiments, at least one $Ar_1$ may be selected from Formulae 3a to 3i, where, in Formulae 3a to 3i, * indicates a binding site.

-continued

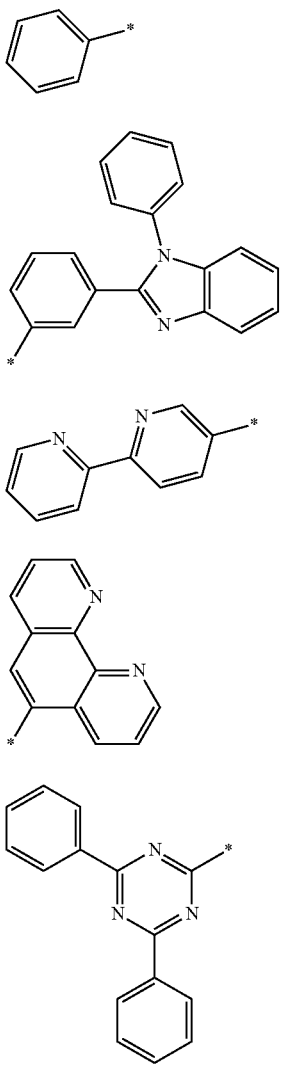

3e

3f

3g

3h

3i

In an embodiment, Formulae 1 and 2 may be represented by Formulae 5 and 6, respectively:

Formula 5

Formula 6

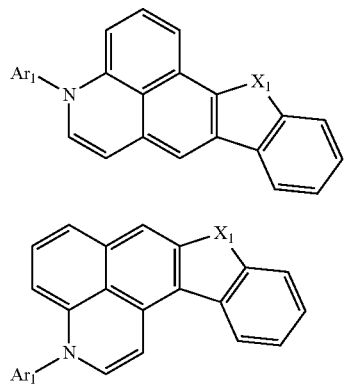

The definitions of substituents of Formulae 5 and 6 are the same as described above. For example, in Formulae 5 and 6, $X_1$ and $Ar_1$ may be the same as described in connection with Formulae 1 and 2. In some embodiments, $Ar_2$ and $Ar_3$ may each be a methyl group.

In an embodiment, the compound represented by one selected from Formulae 1 and 2 may be one selected from any of the following compounds (Compounds A1 to A120):

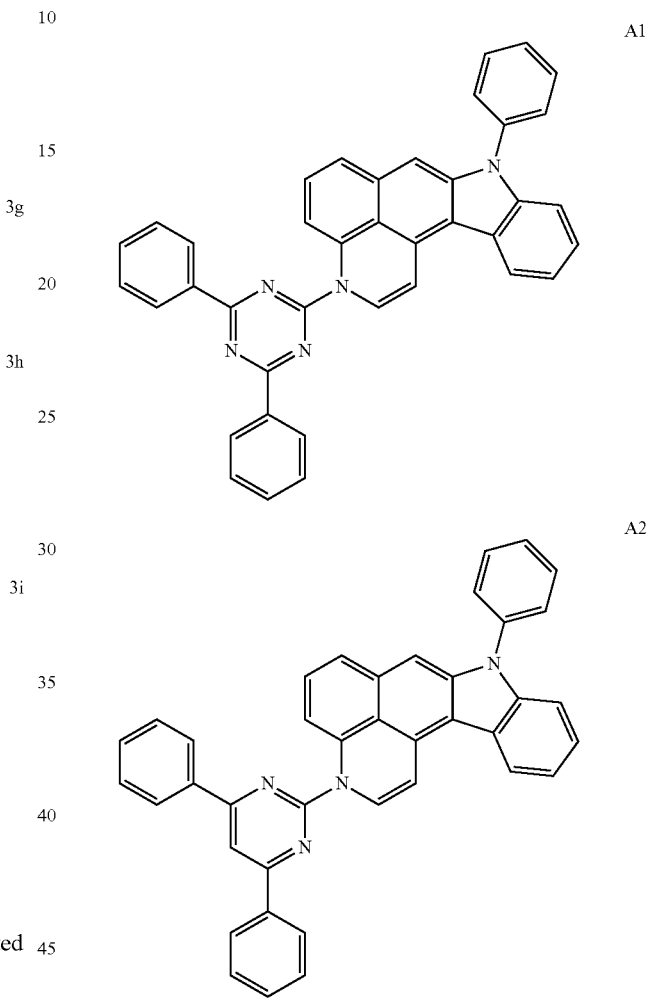

A1

A2

A3

A4
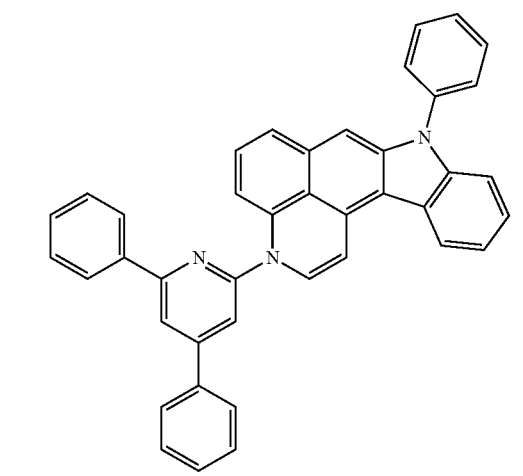
A5
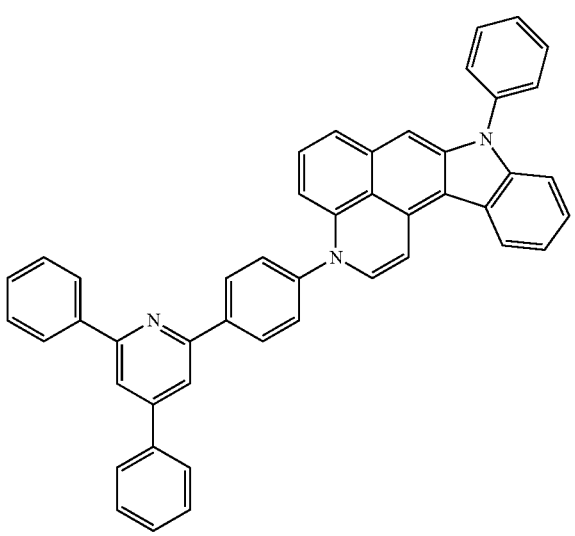
A6
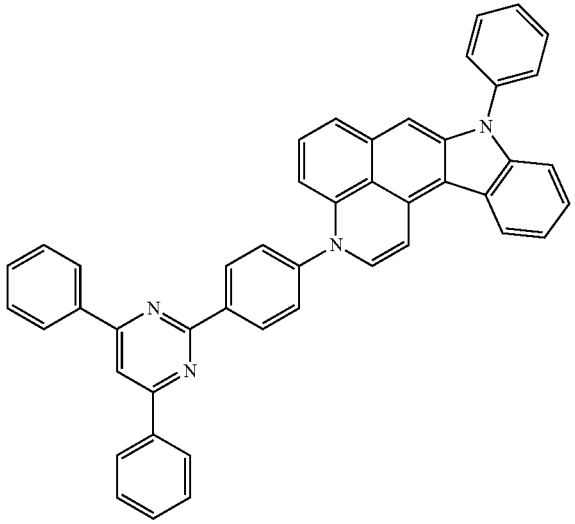
A7
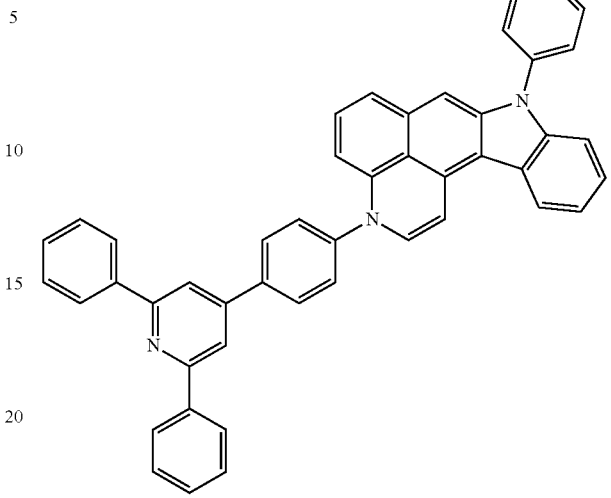
A8
A9
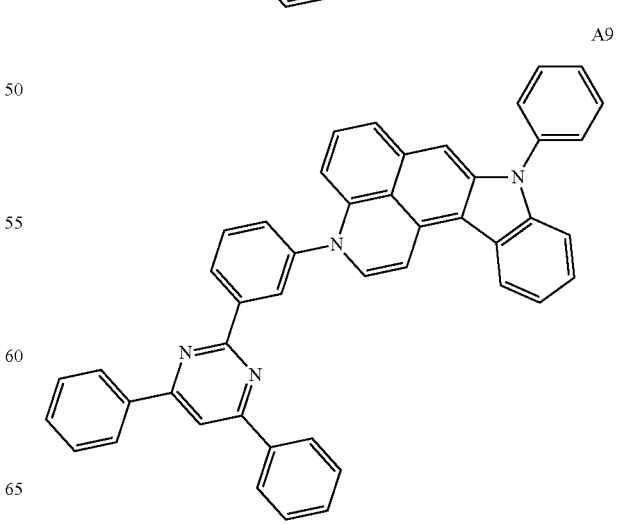

-continued
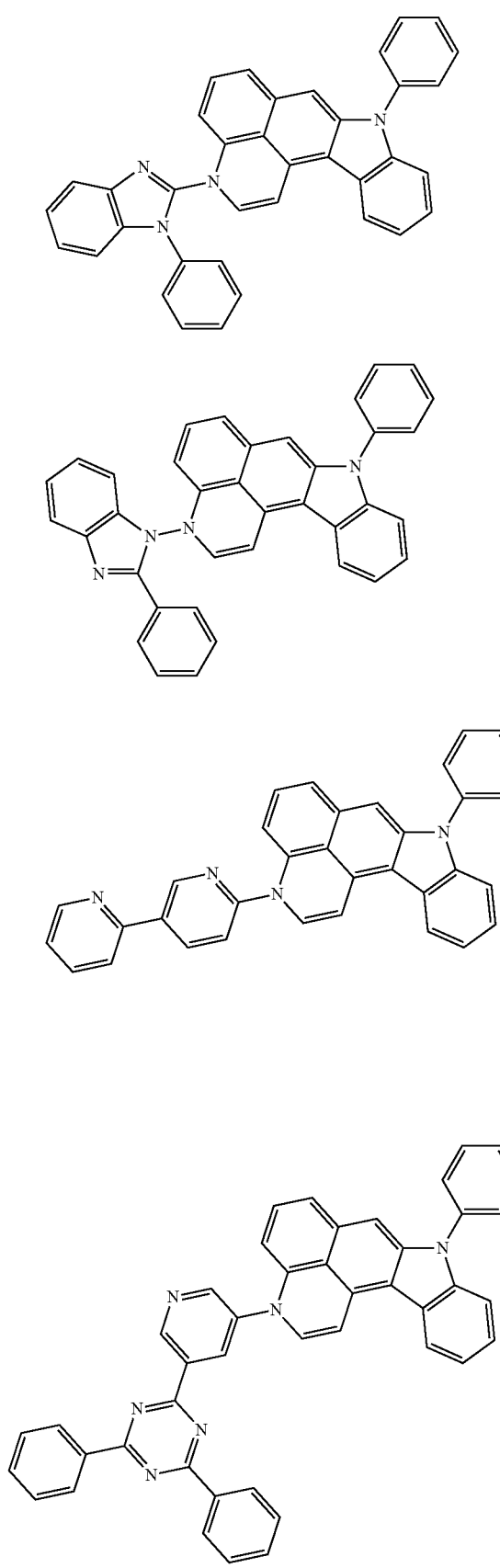
A10
A11
A12
A13
-continued
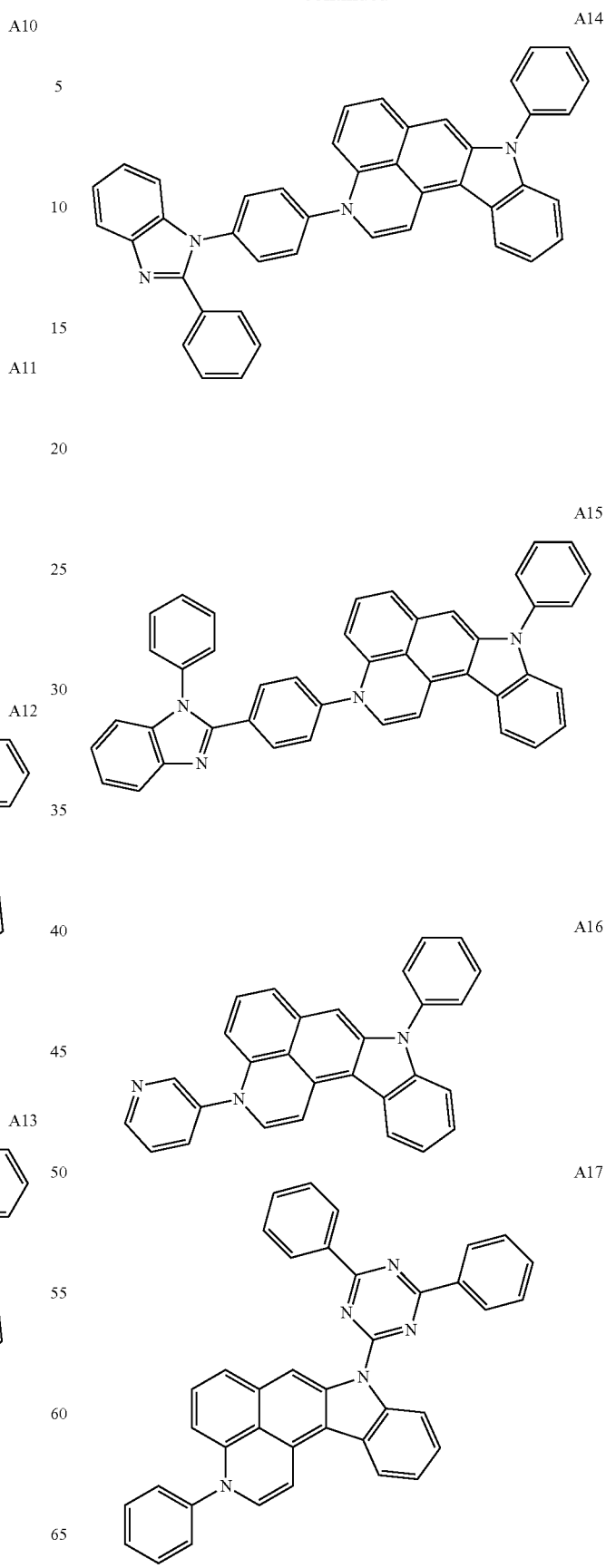
A14
A15
A16
A17

-continued
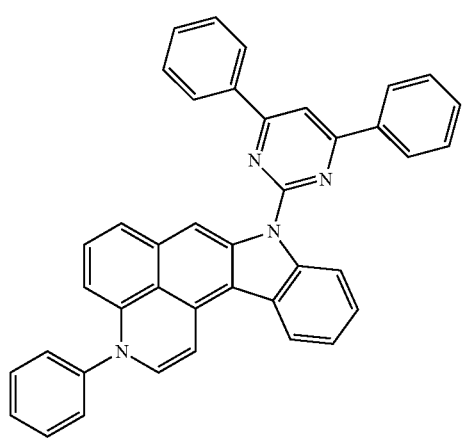
A18
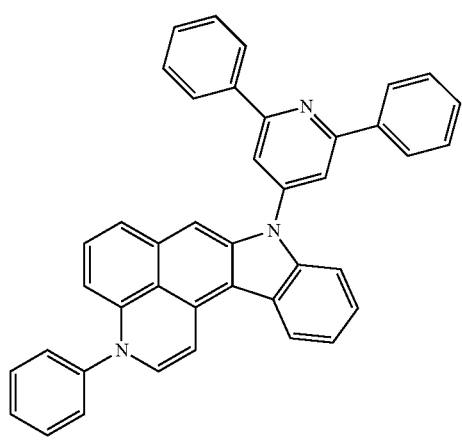
A19
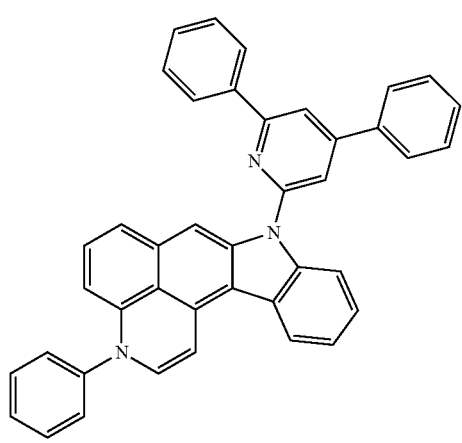
A20
-continued
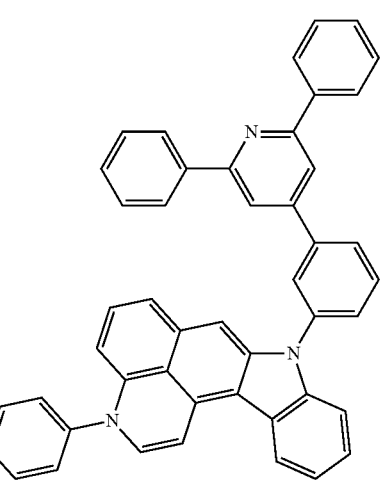
A21
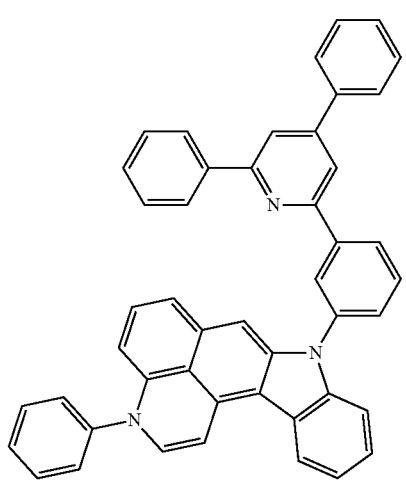
A22
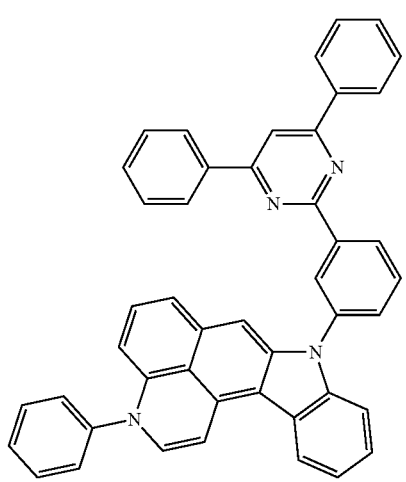
A23

-continued
A24
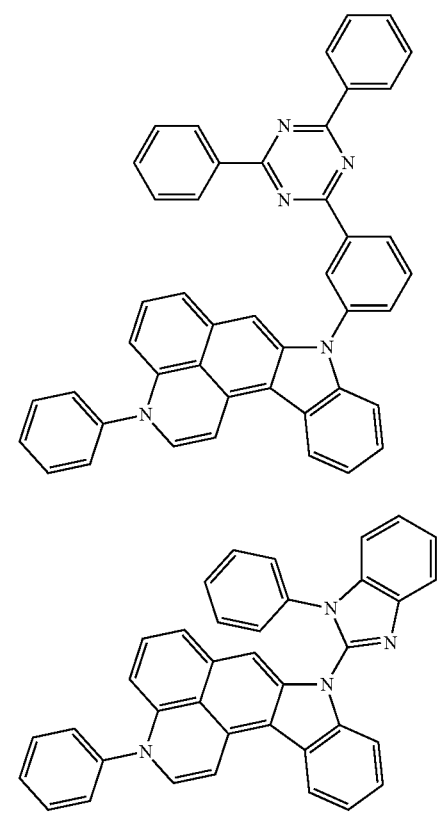
A25
A26
A27
-continued
A28
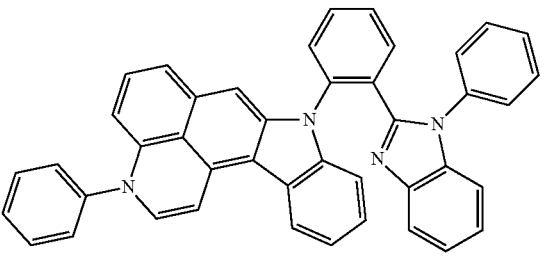
A29
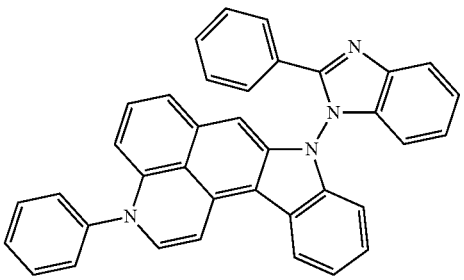
A30
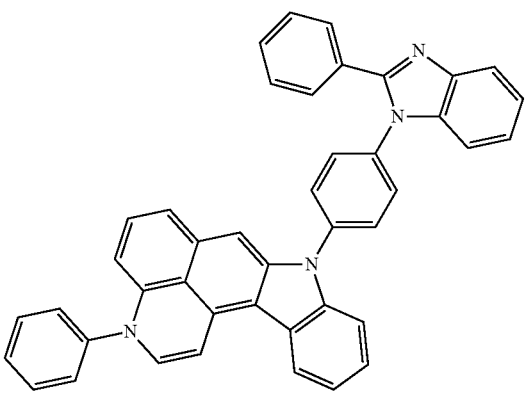
A31
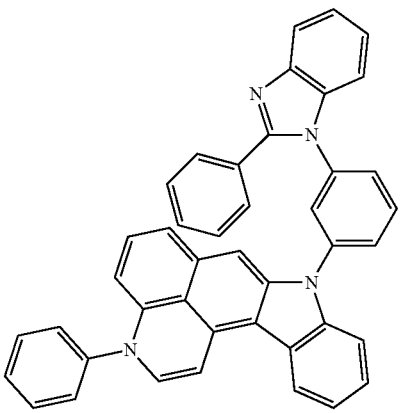

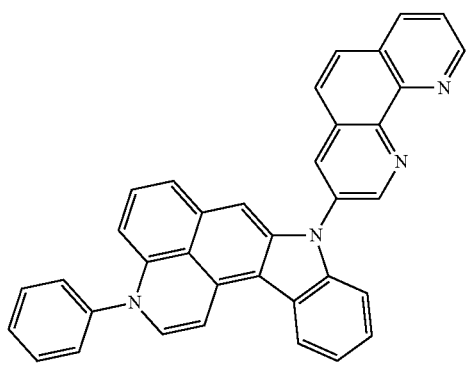
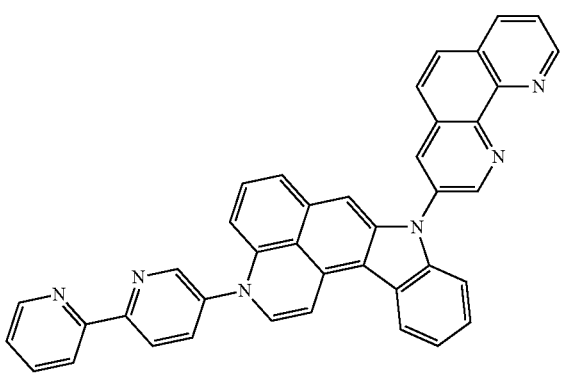
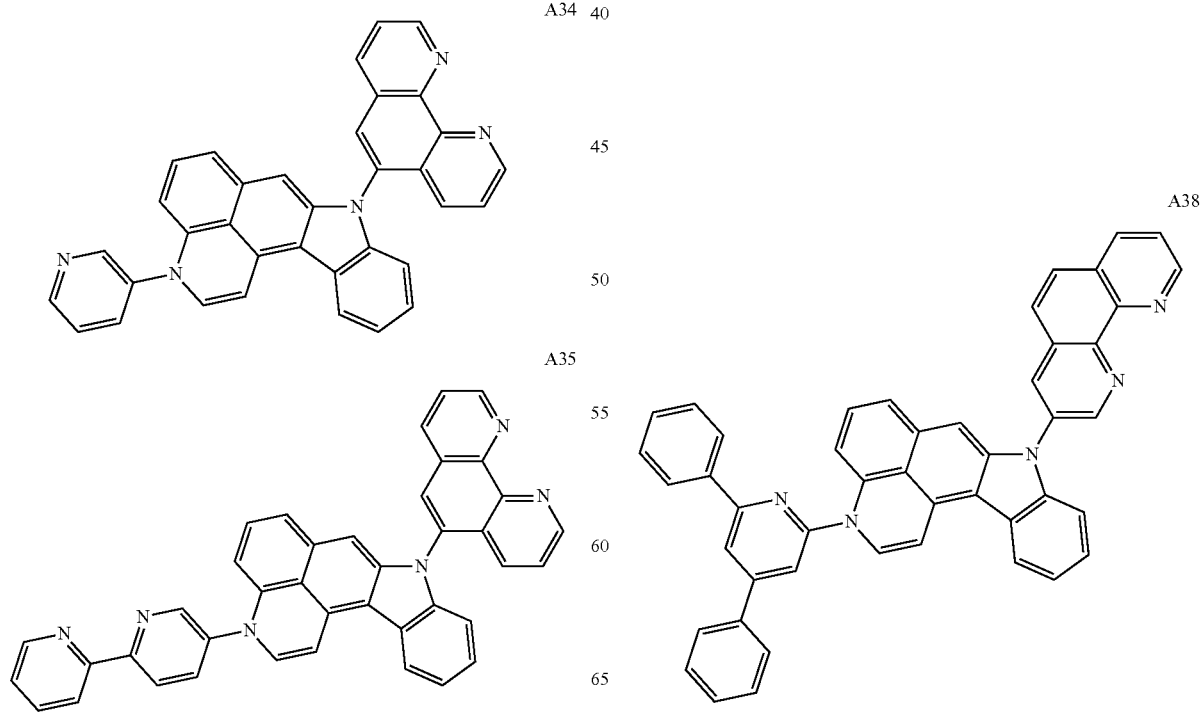

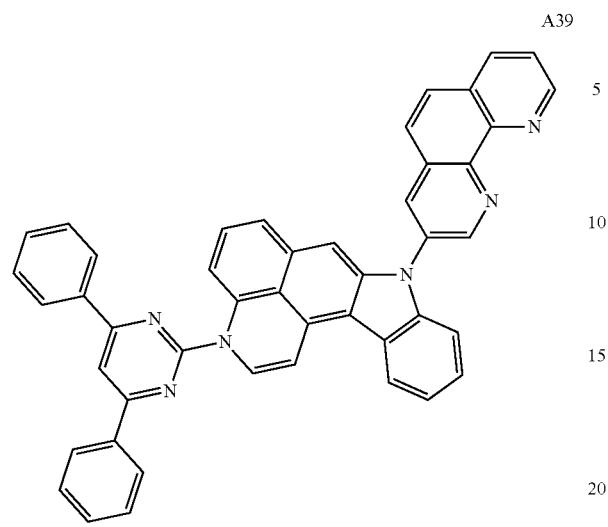
A39
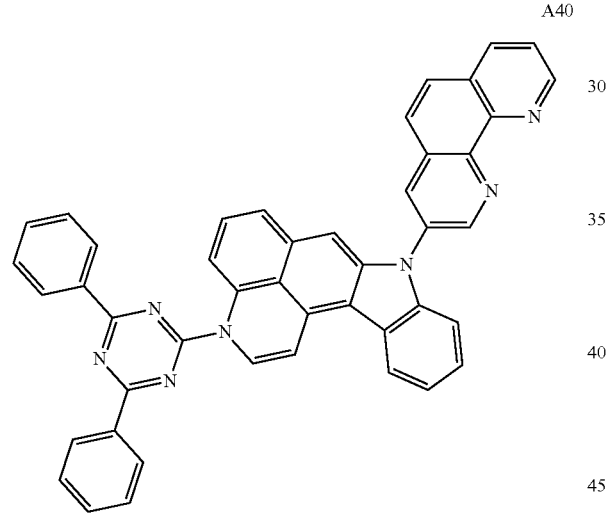
A40
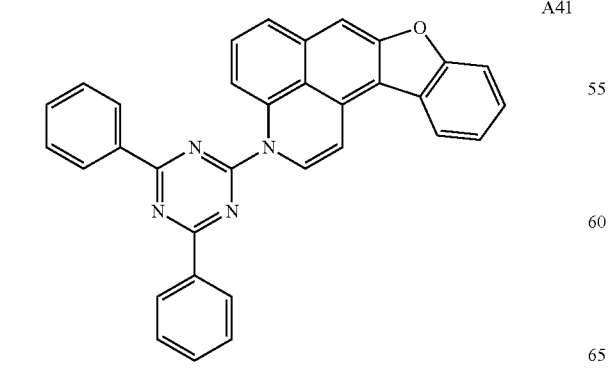
A41
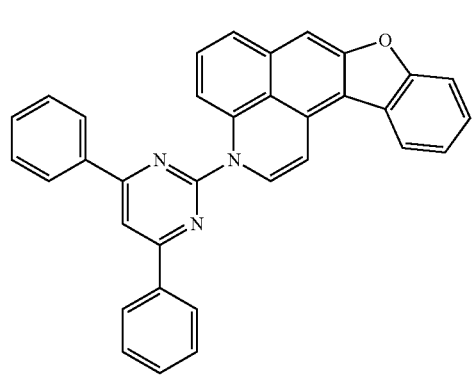
A42
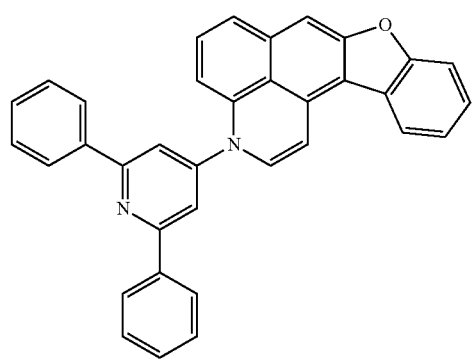
A43
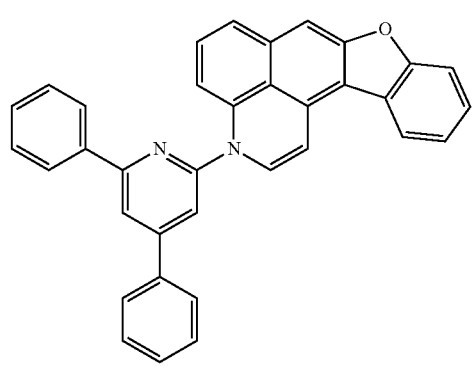
A44
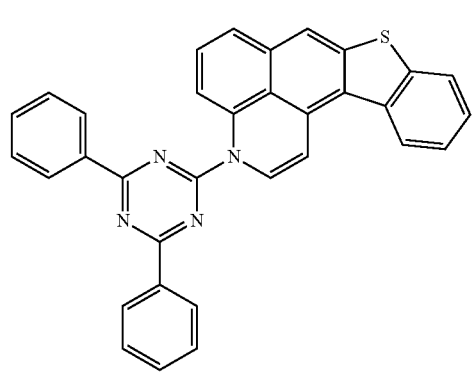
A45

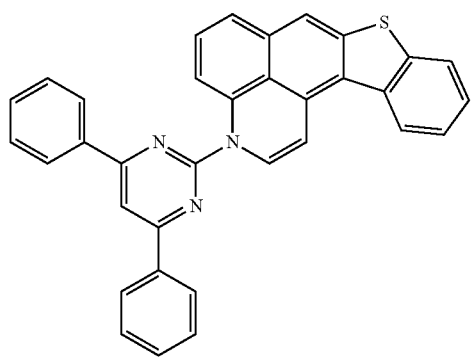
A46
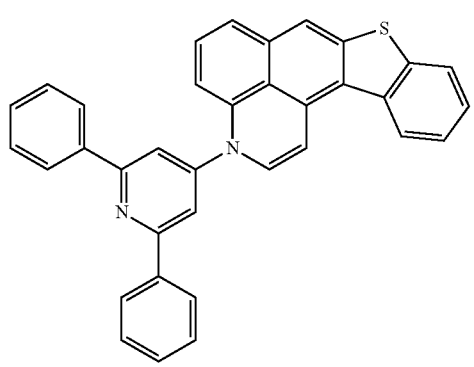
A47
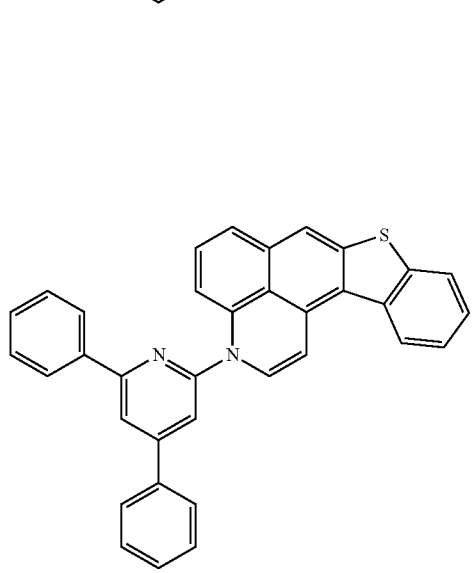
A48
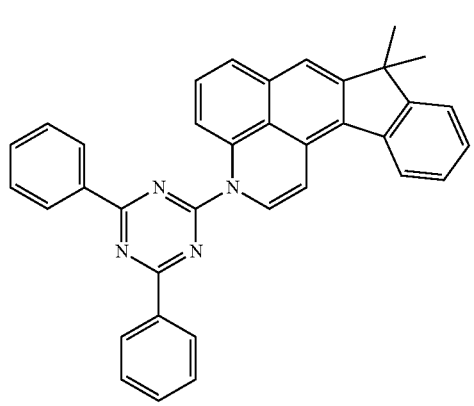
A49
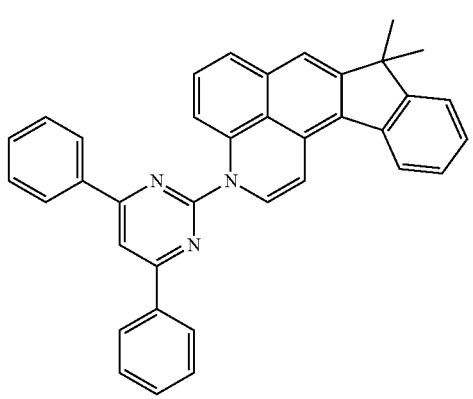
A50
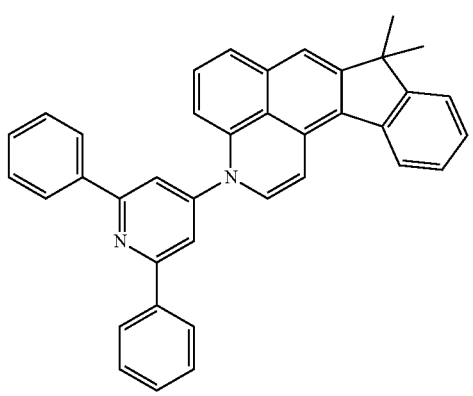
A51
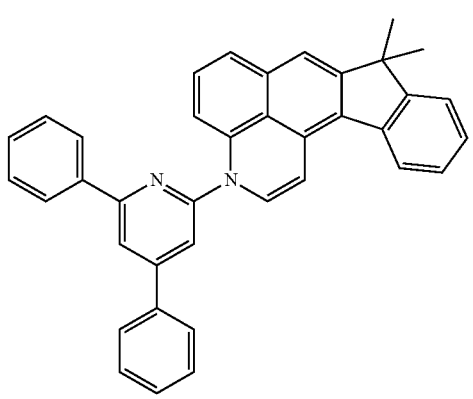
A52
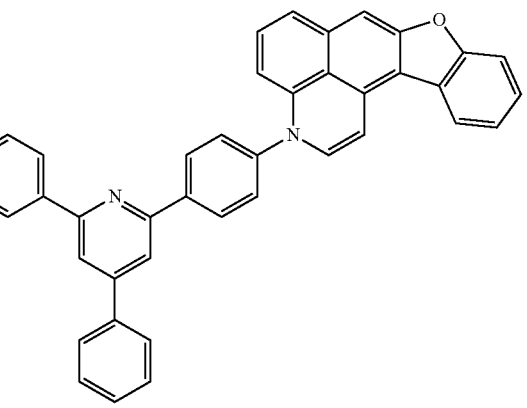
A53

-continued
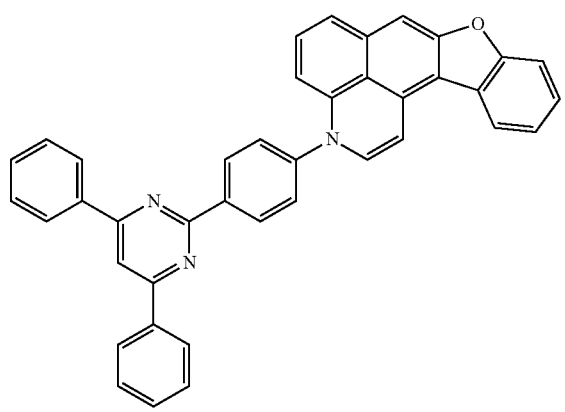
A54
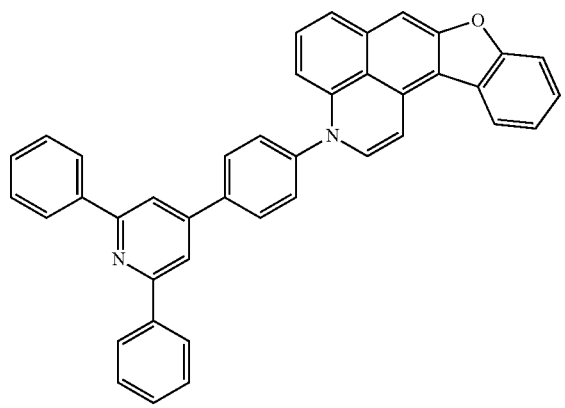
A55
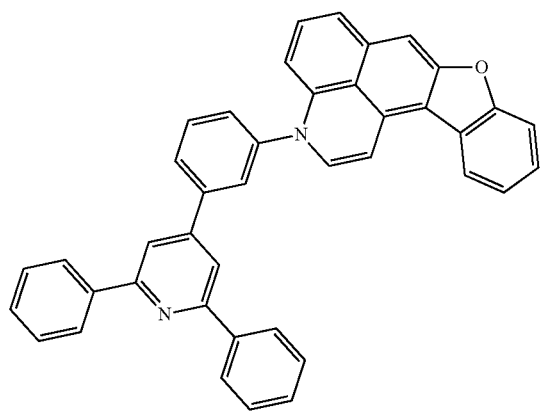
A56
-continued
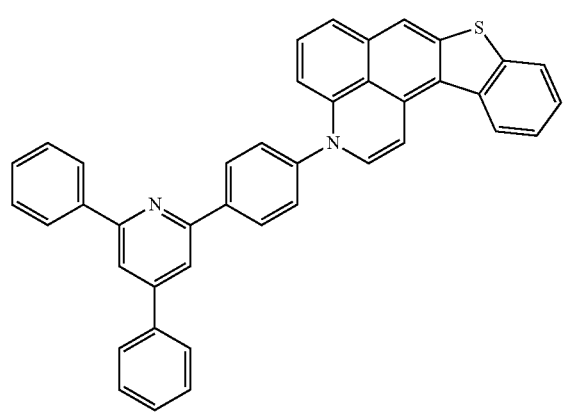
A57
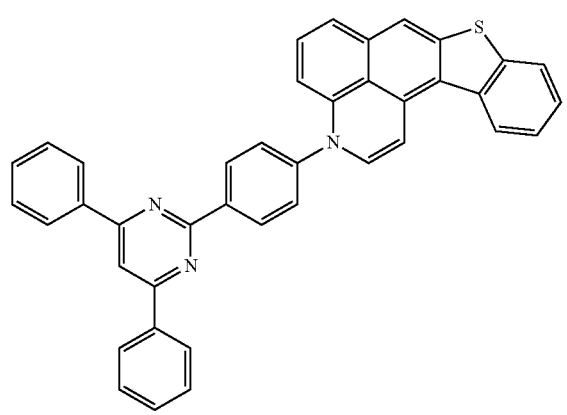
A58
A59

A60
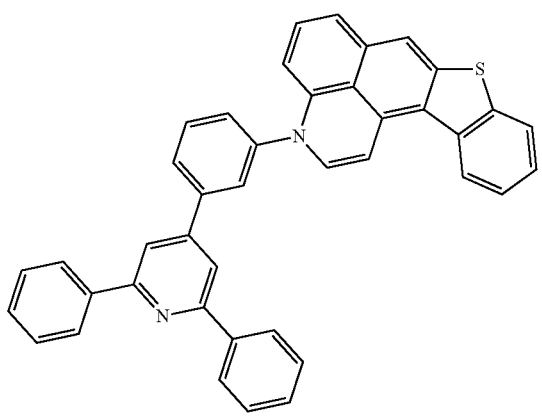
A61
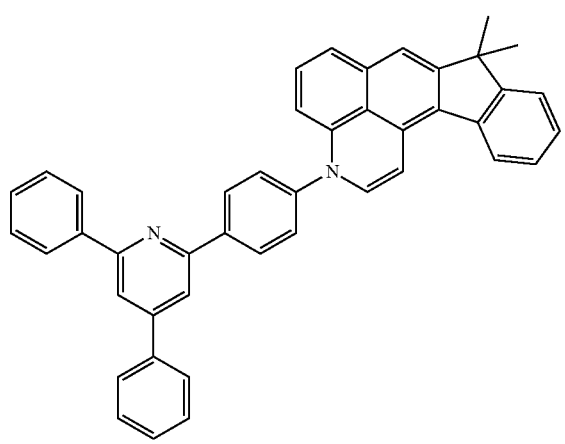
A62
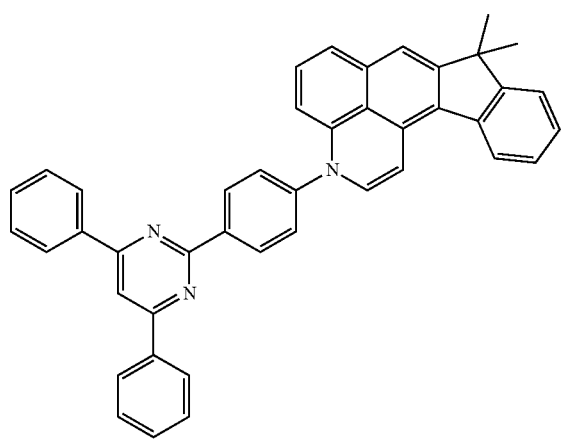
A63
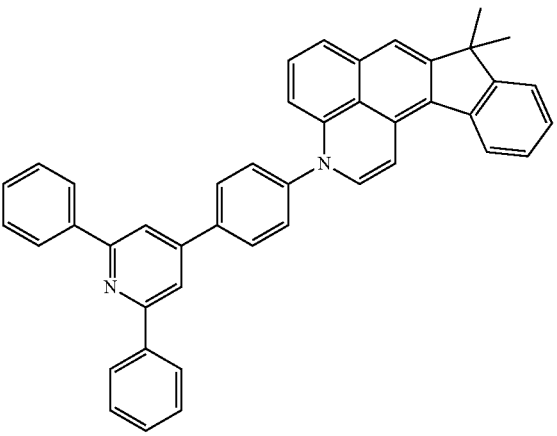
A64
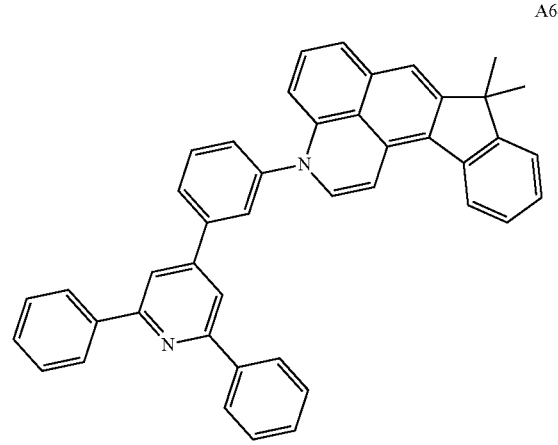
A65
A66
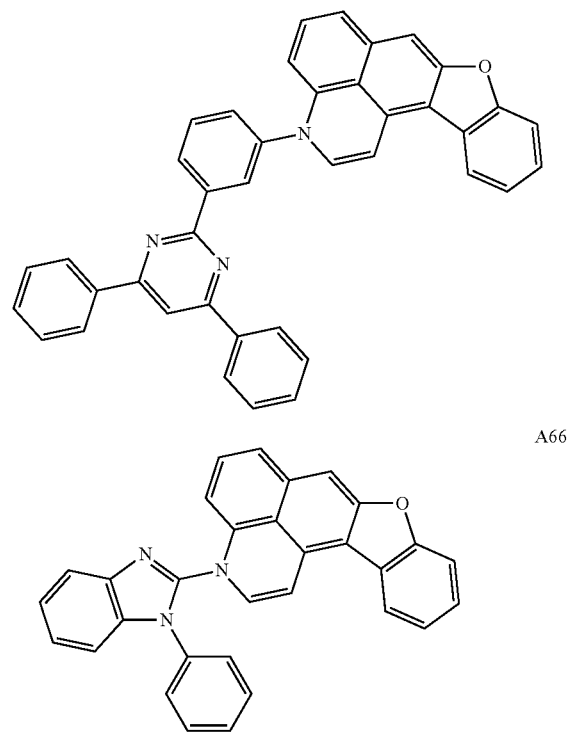

A67
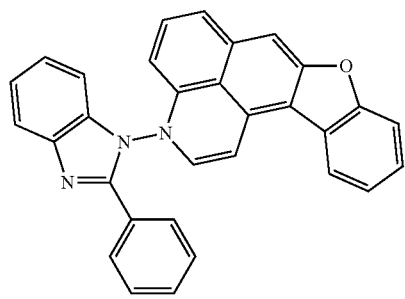
A68
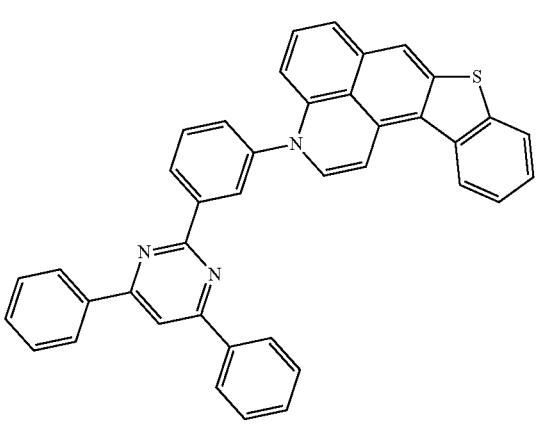
A69
A70
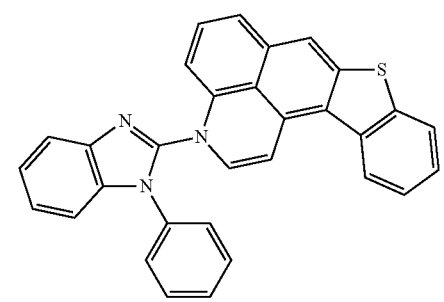
A71
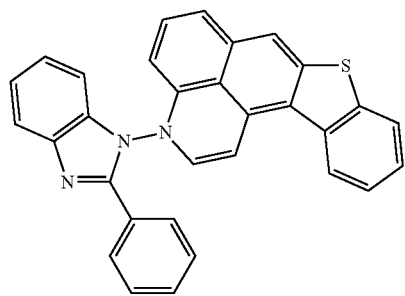
A72
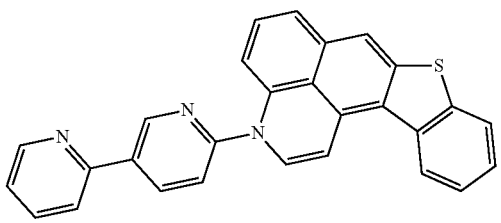
A73
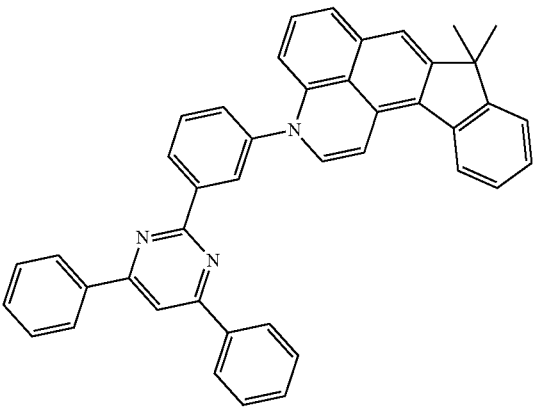
A74
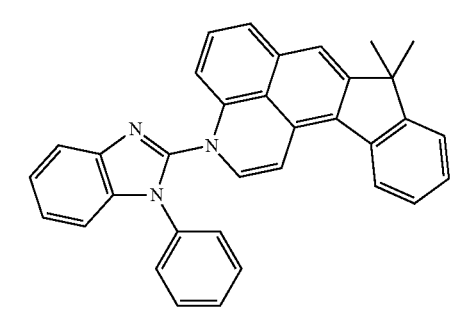
A75
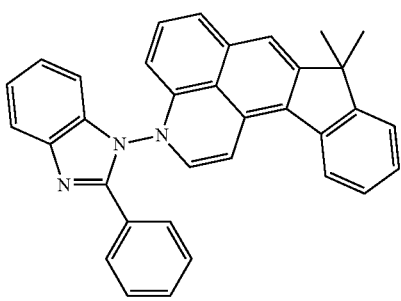
A76
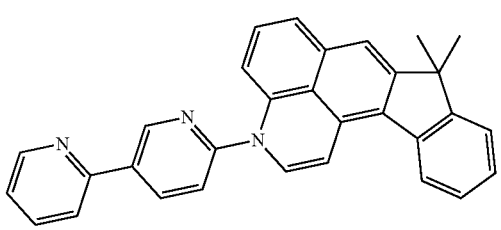

-continued
A77
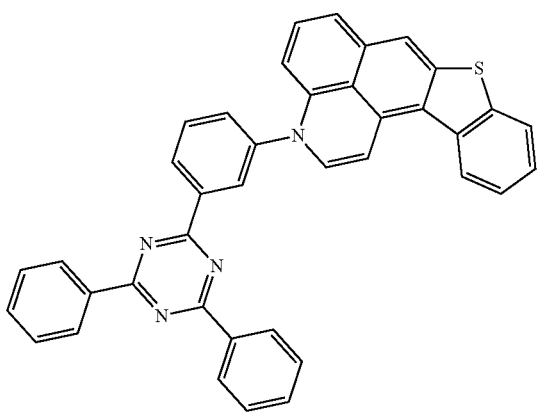
A78
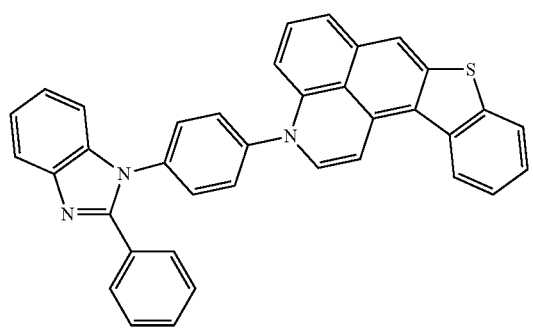
A79
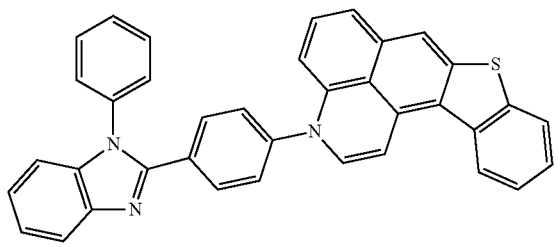
A80
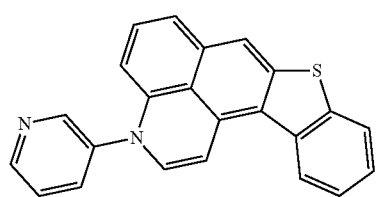
-continued
A81
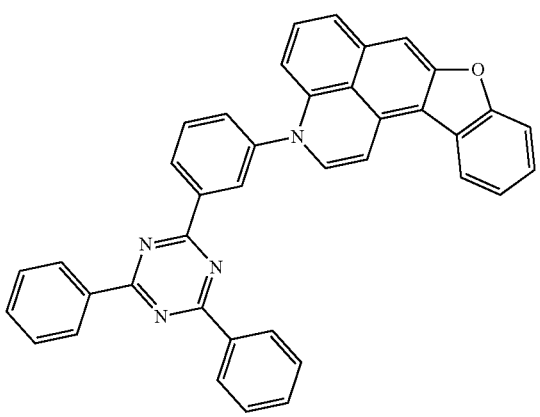
A82
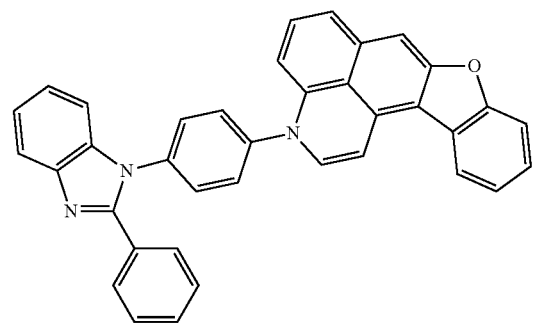
A83
A84
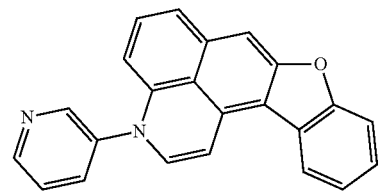

A85
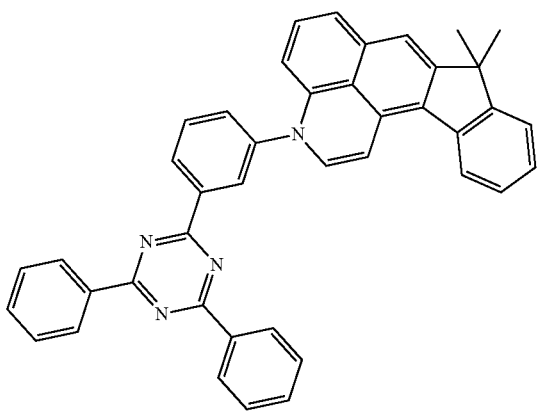
A86
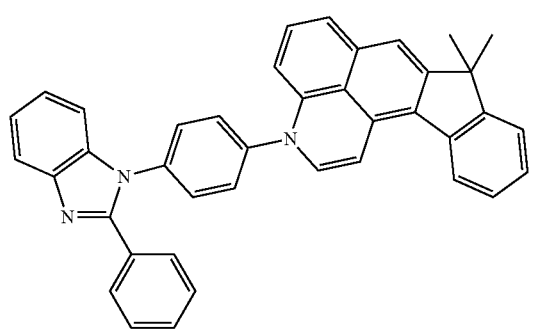
A87
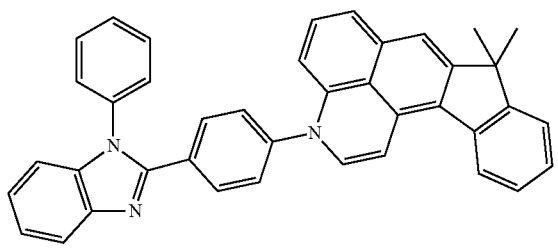
A88
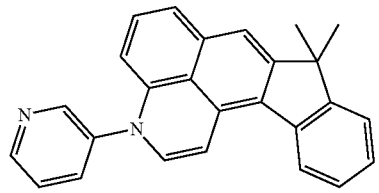
A89
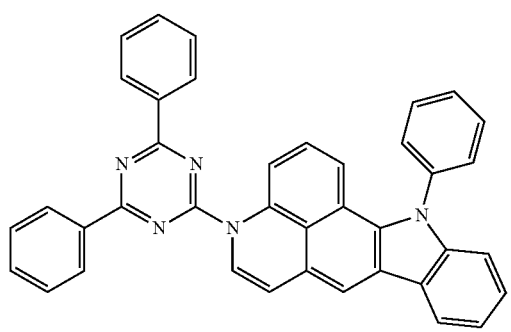
A90
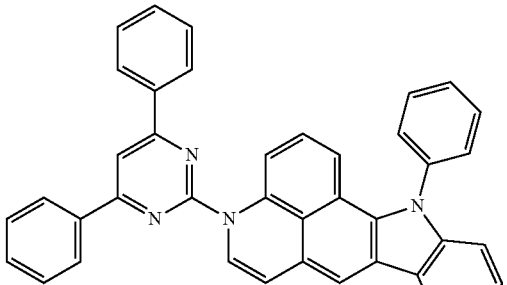
A91
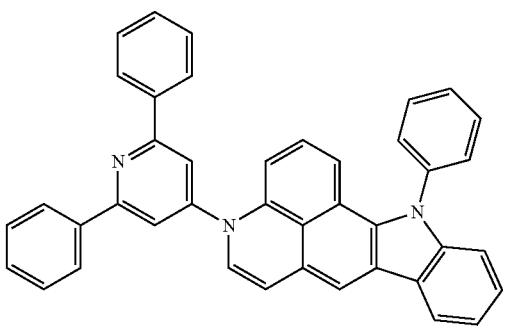
A92
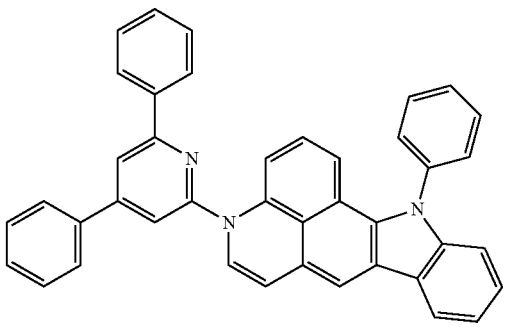
A93
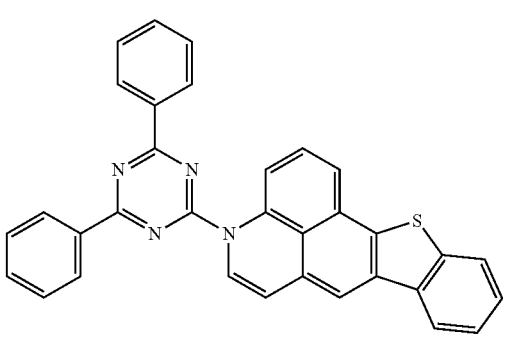

A94 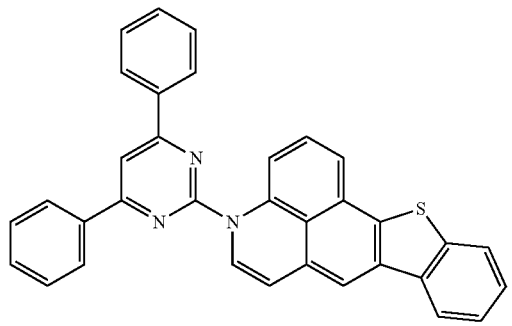
A95 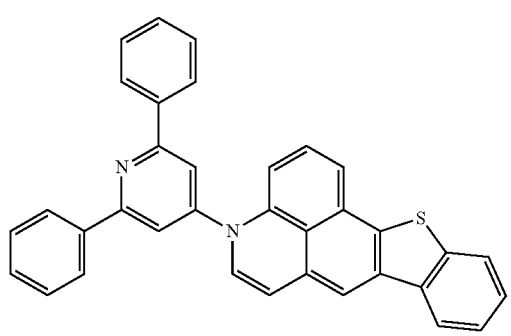
A96 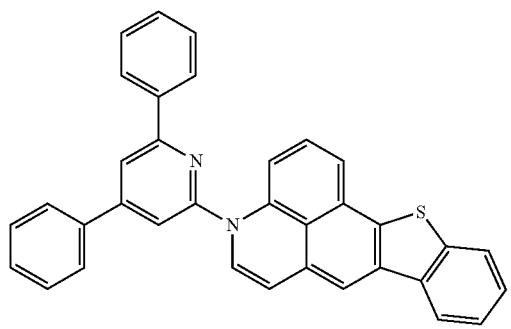
A97 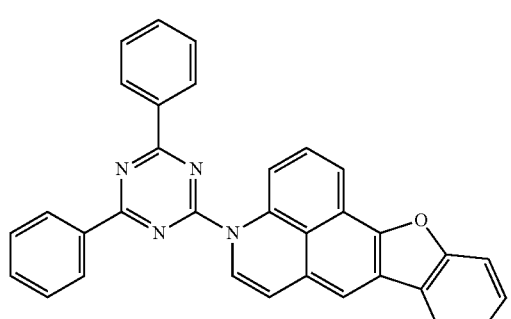
A98 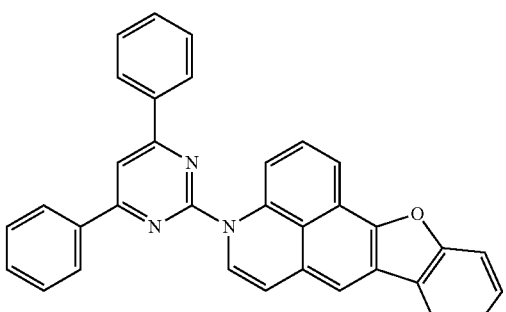
A99 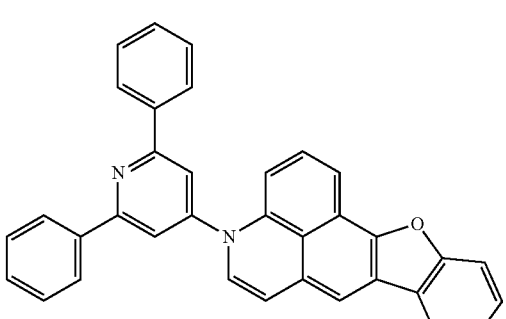
A100 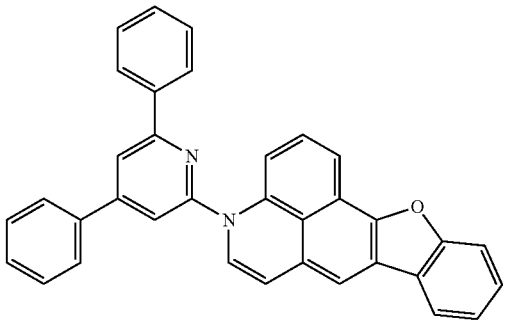
A101 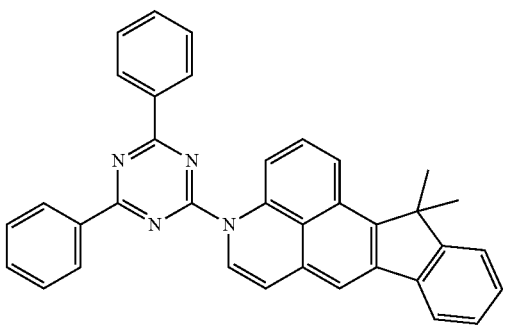

A102
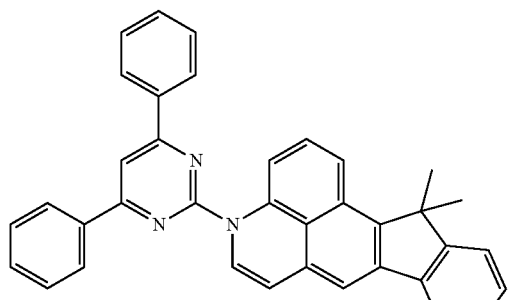
A103
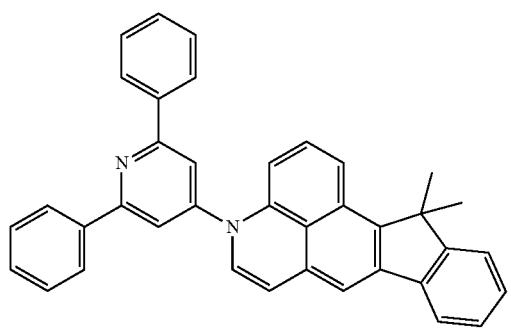
A104
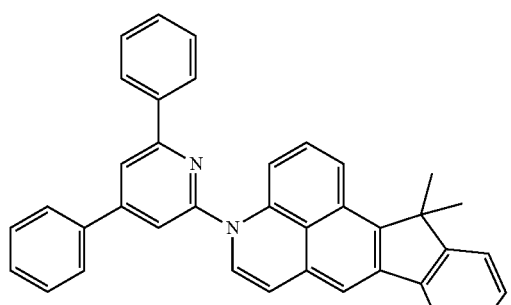
A105
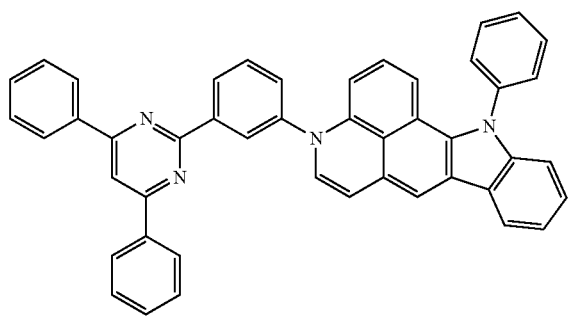
A106
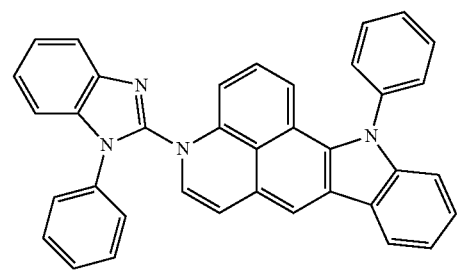
A107
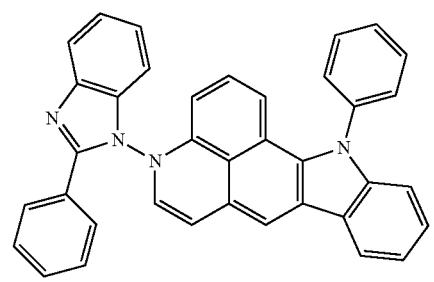
A108
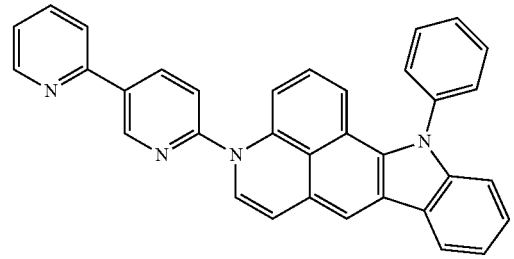
A109
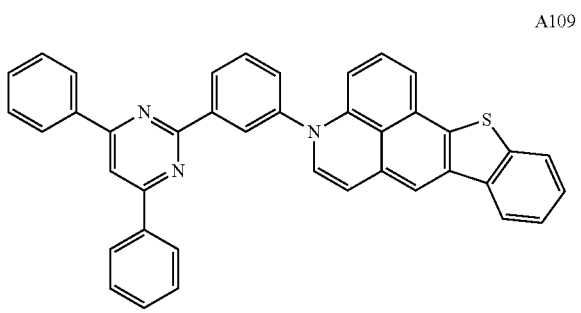
A110
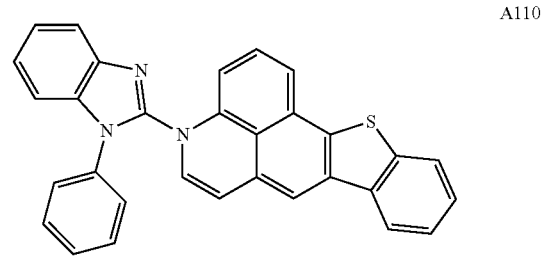

A111
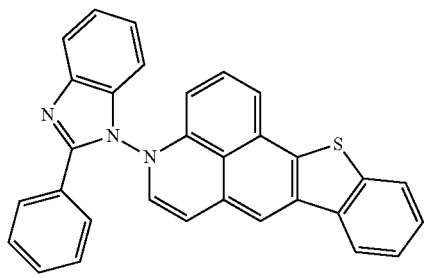

A112
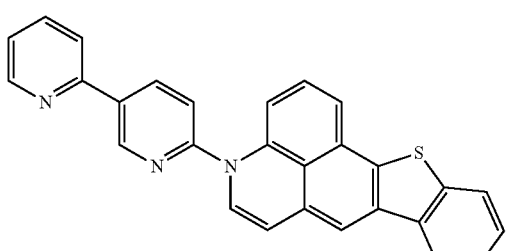

A113
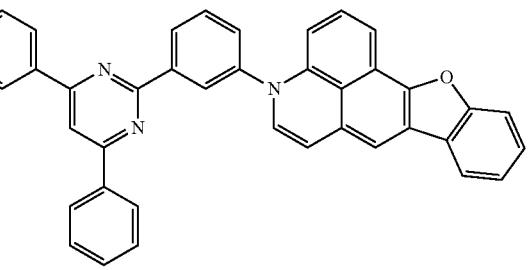

A114
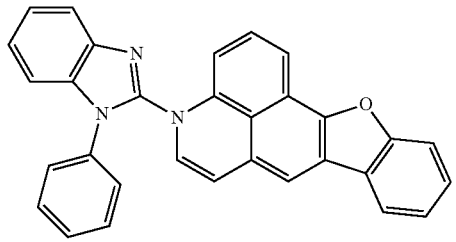

A115
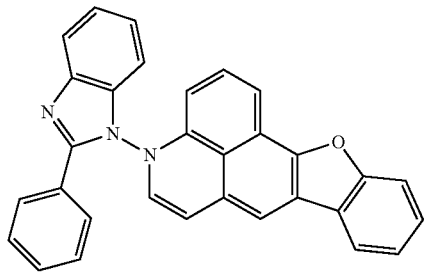

A116
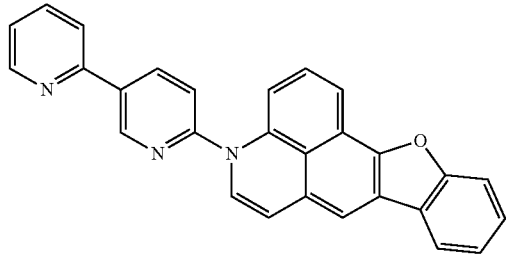

A117
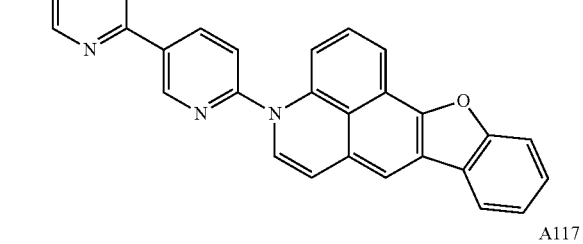

A118
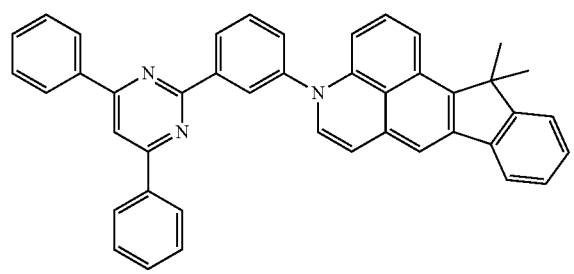

A119
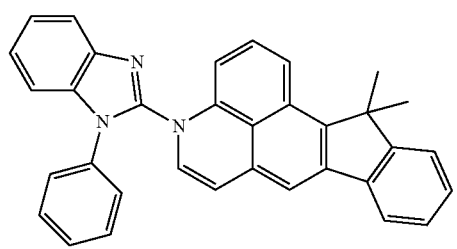

A120
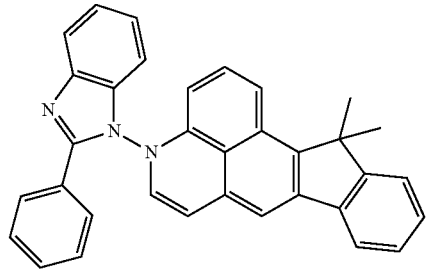

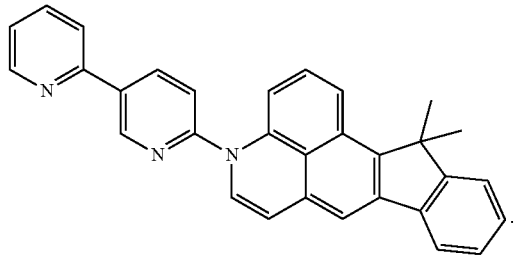

In some compounds, the compound represented by one selected from Formulae 1 and 2 (or represented by one selected from Formulae 3 and 4) may be one selected from compounds A1, A2, A9, A14, A15, A17, A23, A27, A35, A41, A45, A49, A78, A79, A82, A83, A86, A87, A89, A93, A97, and A101.

Descriptions of FIG. 1

FIG. 1 is a diagram schematically illustrating a cross-section of a structure of an organic light-emitting device 10 according to an embodiment. The organic light-emitting device 10 includes a first electrode 110, an organic layer 150 on the first electrode 110, and a second electrode 190 on the organic layer 150.

Hereinafter, the structure of the organic light-emitting device 10 according to an embodiment and a method of manufacturing the organic light-emitting device 10, according to an embodiment, will be described in connection with FIG. 1.

First Electrode 110

In FIG. 1, a substrate may be located under the first electrode 110 or above the second electrode 190. The substrate may be a glass substrate or a transparent plastic substrate, each having excellent mechanical strength, thermal stability, transparency, surface smoothness, ease of handling, and water-resistance.

The first electrode 110 may be formed by depositing or sputtering a material for the first electrode 110 on the substrate. When the first electrode 110 is an anode, the material for the first electrode 110 may be selected from materials having a high work function to facilitate hole injection.

The first electrode 110 may be a reflective electrode, a semi-transmissive electrode, or a transmissive electrode. When the first electrode 110 is a transmissive electrode, the material for the first electrode 110 may be selected from indium tin oxide (ITO), indium zinc oxide (IZO), tin oxide ($SnO_2$), zinc oxide (ZnO), and any combinations thereof, but the first electrode 110 is not limited thereto. In various embodiments, when the first electrode 110 is a semi-transmissive electrode or a reflective electrode, the material for the first electrode 110 may be selected from magnesium (Mg), aluminum (Al), aluminum-lithium (Al—Li), calcium (Ca), magnesium-indium (Mg—In), magnesium-silver (Mg—Ag), and any combinations thereof, but the first electrode 110 is not limited thereto.

The first electrode 110 may have a single-layered structure, or a multi-layered structure including a plurality of layers. For example, the first electrode 110 may have a three-layered structure of ITO/Ag/ITO, but the structure of the first electrode 110 is not limited thereto.

Organic Layer 150

The organic layer 150 is on the first electrode 110. The organic layer 150 may include an emission layer.

The organic layer 150 may include a hole transport region between the first electrode 110 and the emission layer, and an electron transport region between the emission layer and the second electrode 190.

Hole Transport Region of Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer, but the hole transport region is not limited thereto.

For example, the hole transport region may have a single-layered structure including a single layer including a plurality of different materials, or a multi-layered structure having a structure of hole injection layer/hole transport layer, a structure of hole injection layer/hole transport layer/emission auxiliary layer, a structure of hole injection layer/emission auxiliary layer, a structure of hole transport layer/emission auxiliary layer, or a structure of hole injection layer/hole transport layer/electron blocking layer, wherein, for each structure, constituting layers are sequentially stacked from the first electrode 110 in the stated order, but the structure of the hole transport region is not limited thereto.

The hole transport region may include at least one selected from m-MTDATA, TDATA, 2-TNATA, NPB (also referred to as NPD), β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA), polyaniline/poly(4-styrenesulfonate) (Pani/PSS), a compound represented by Formula 201, and a compound represented by Formula 202:

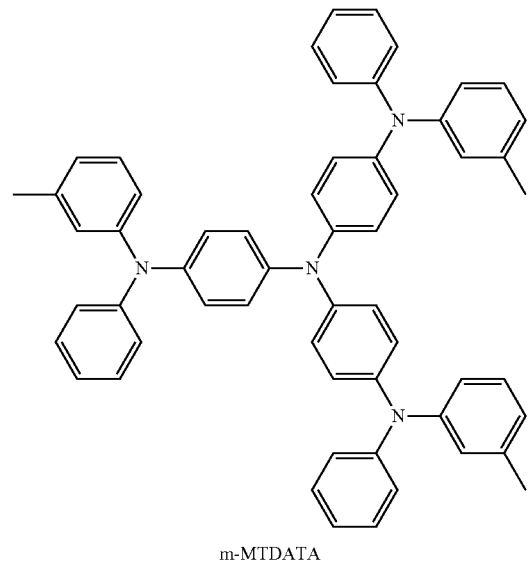

m-MTDATA

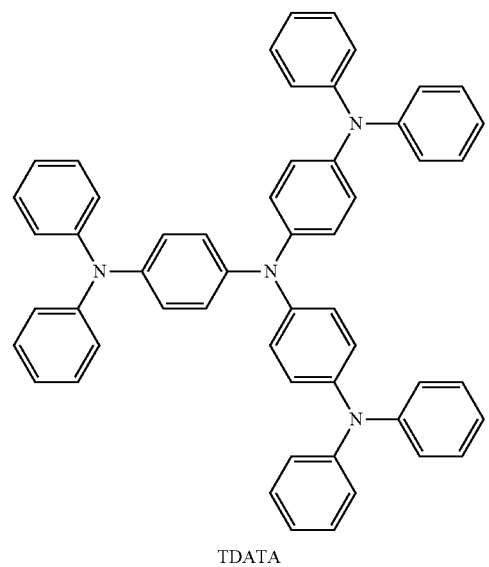

TDATA

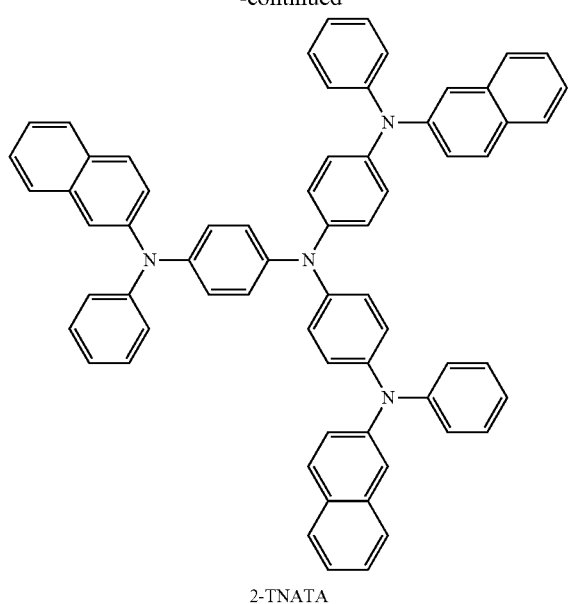
2-TNATA
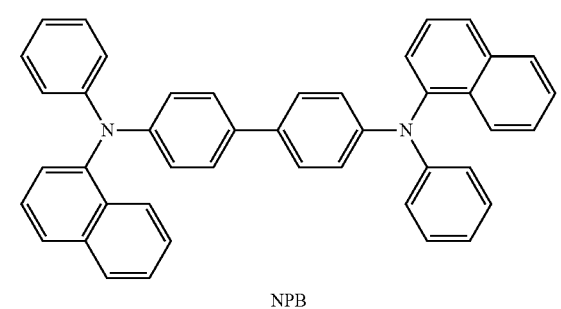
NPB
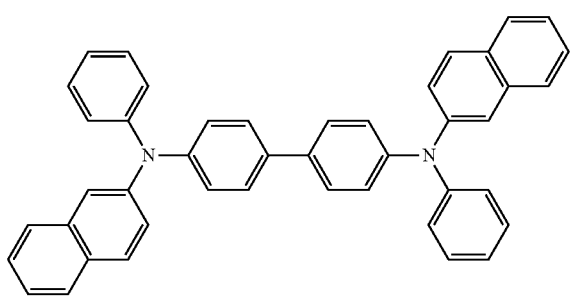
β-NPB
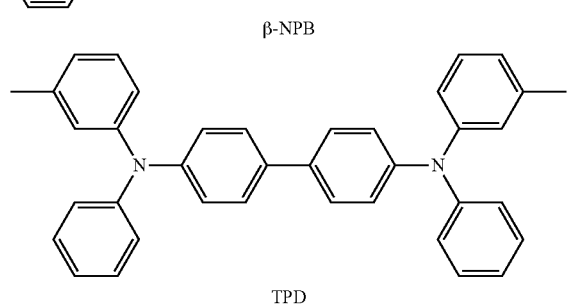
TPD
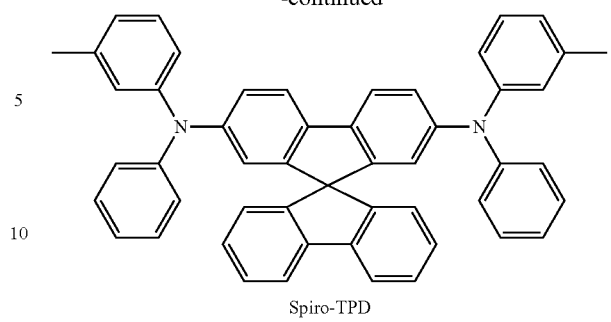
Spiro-TPD
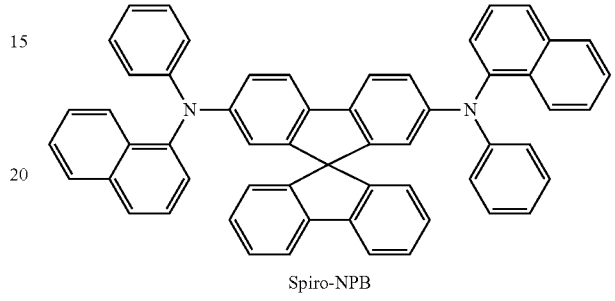
Spiro-NPB
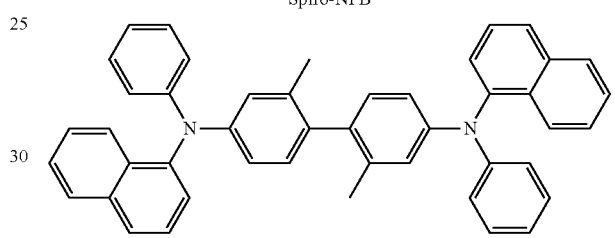
methylated NPB
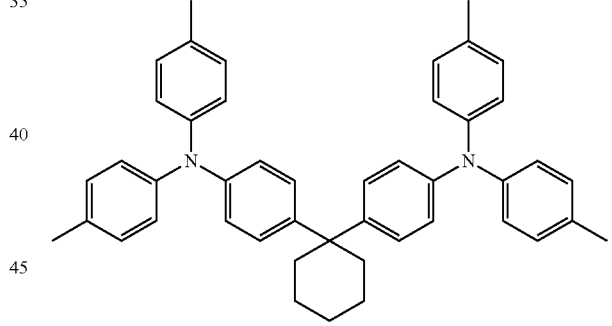
TAPC
HMTPD
Formula 201
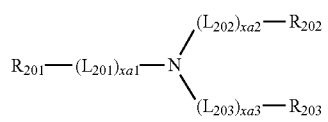

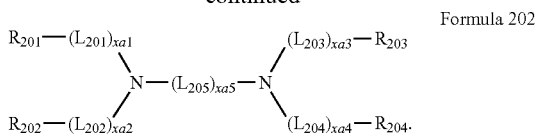

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, where * indicates a binding site, xa1 to xa4 may each independently be an integer selected from 0 to 3, xa5 may be an integer selected from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked to each other through a single bond, a dimethyl-methylene group, or a diphenyl-methylene group, and $R_{203}$ and $R_{204}$ may optionally be linked through a single bond, a dimethyl-methylene group, or a diphenyl-methylene group.

In an embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In various embodiments, xa1 to xa4 may each independently be 0, 1, or 2.

In various embodiments, xa5 may be 1, 2, 3, or 4.

In various embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be the same as described elsewhere herein in connection with those provided in the present disclosure (e.g., $Q_{31}$ to $Q_{33}$ may be the same as described in connection with $L_{201}$ to $L_{205}$).

In various embodiments, in Formula 201, at least one selected from $R_{201}$ to $R_{203}$ may be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the compound represented by Formula 202 are not limited thereto.

In various embodiments, in Formula 202, i) $R_{201}$ and $R_{202}$ may be linked to each other through a single bond and/or ii) $R_{203}$ and $R_{204}$ may be linked to each other through a single bond.

In various embodiments, in Formula 202, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the compound represented by Formula 202 are not limited thereto.

The compound represented by Formula 201 may be represented by Formula 201A:

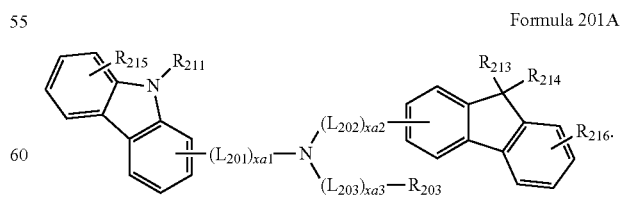

Formula 201A

For example, the compound represented by Formula 201 may be represented by Formula 201A(1), but embodiments of the compound represented by Formula 201 are not limited thereto:

Formula 201A(1)

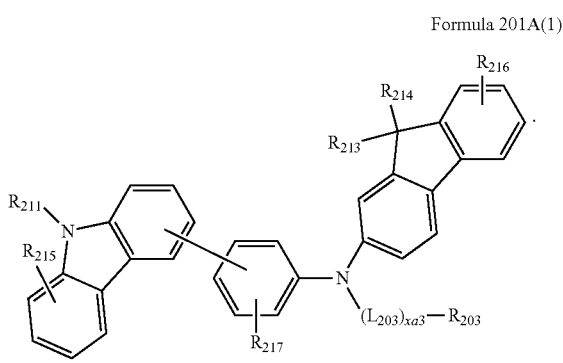

In various embodiments, the compound represented by Formula 201 may be represented by Formula 201A-1, but embodiments of the compound represented by Formula 201 are not limited thereto:

Formula 201A-1

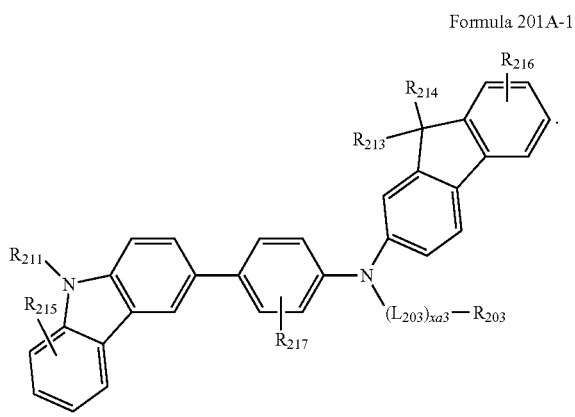

In various embodiments, the compound represented by Formula 202 may be represented by Formula 202A:

Formula 202A

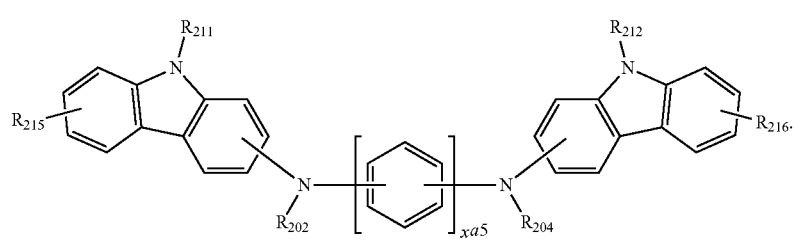

In various embodiments, the compound represented by Formula 202 may be represented by Formula 202A-1:

Formula 202A-1

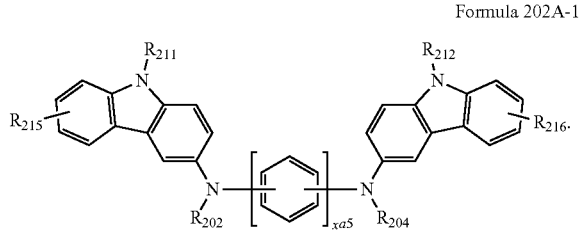

In Formulae 201A, 201A(1), 201A-1, 202A, and 202A-1, $L_{201}$ to $L_{203}$, xa1 to xa3, xa5, and $R_{202}$ to $R_{204}$ may each independently be the same as described herein in connection with those provided in the present disclosure (e.g., $L_{201}$ to $L_{203}$, xa1 to xa3, xa5, and $R_{202}$ to $R_{204}$ may be the same as described in connection with Formulae 201 and 202), $R_{211}$ and $R_{212}$ may each independently be the same as described herein in connection with $R_{203}$ (e.g., $R_{203}$ as described in connection with Formulae 201 and 202), and $R_{213}$ to $R_{217}$ may each independently be selected from hydrogen, deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the hole transport region are not limited thereto:

51
HT1
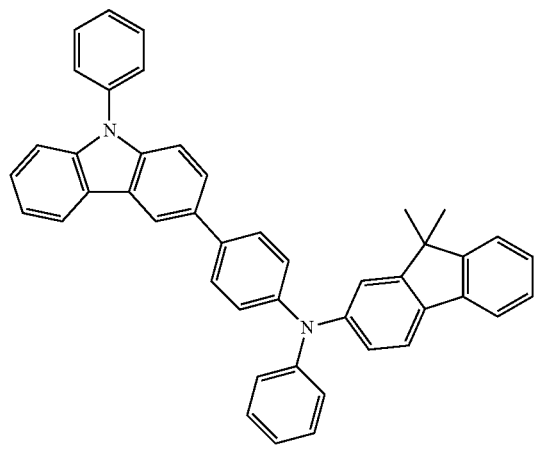
52
HT2
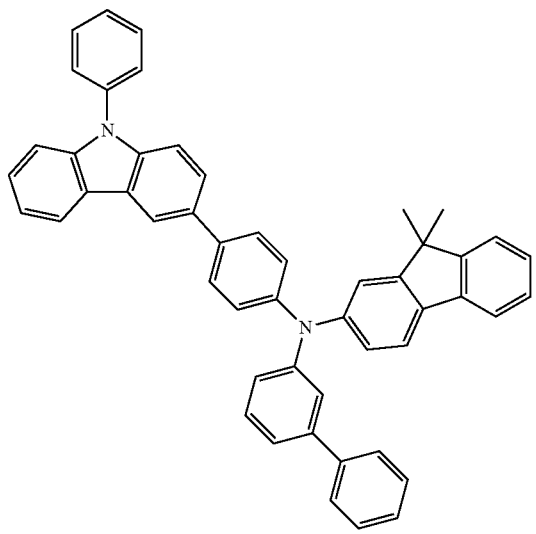
HT3
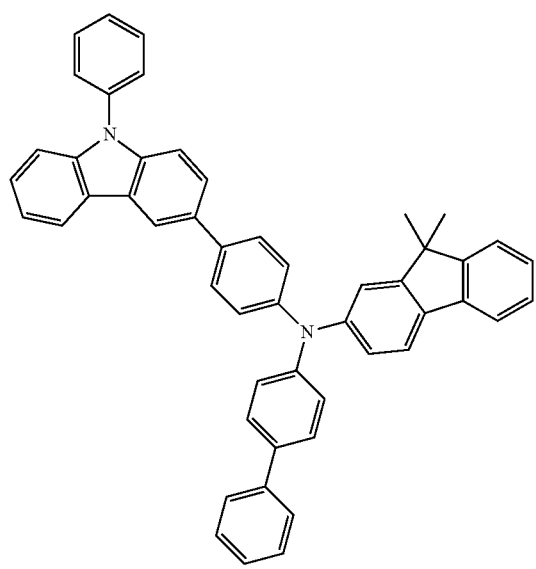
HT4
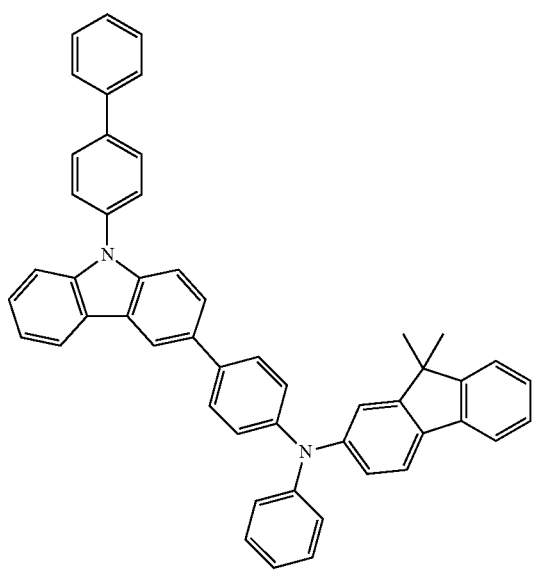

-continued
HT5
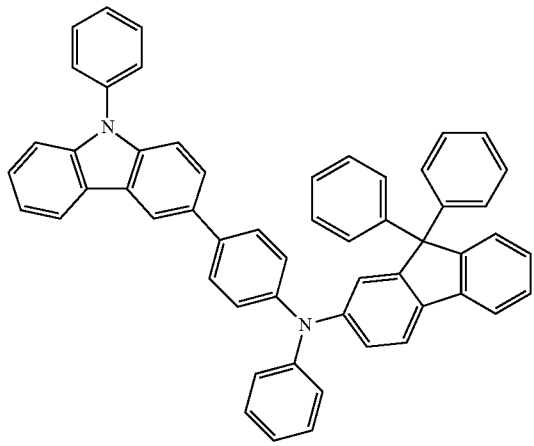
HT6
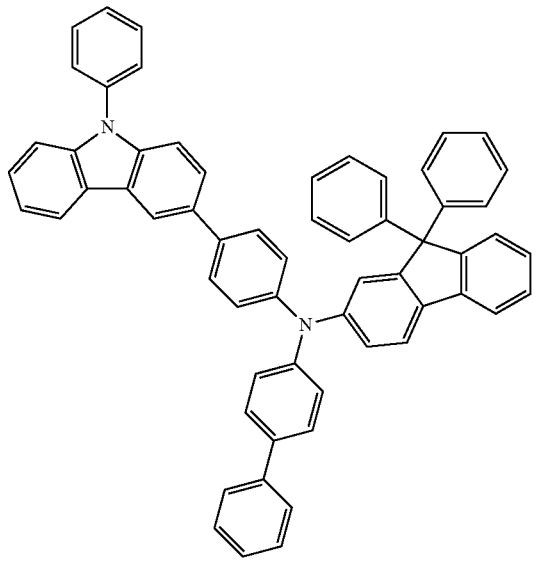
HT7
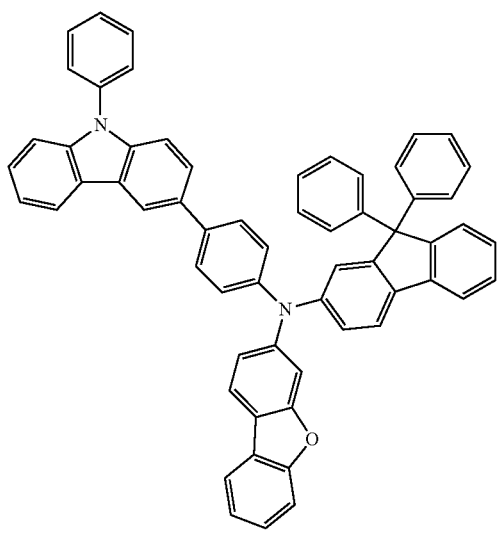
HT8
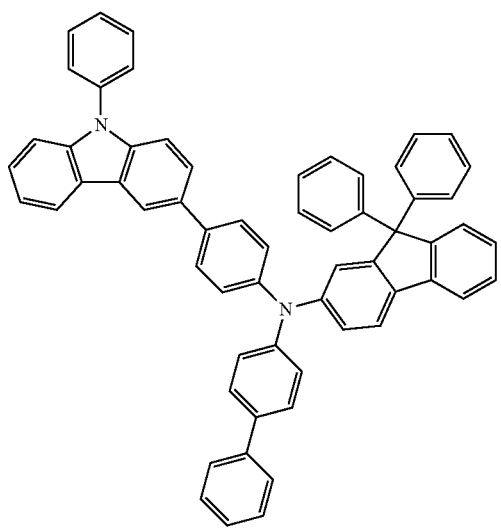
HT9
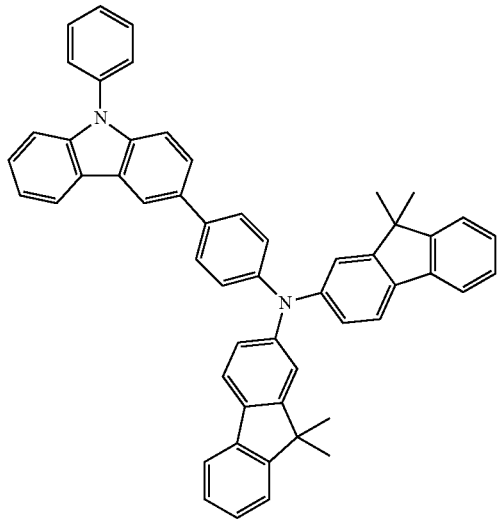
HT10
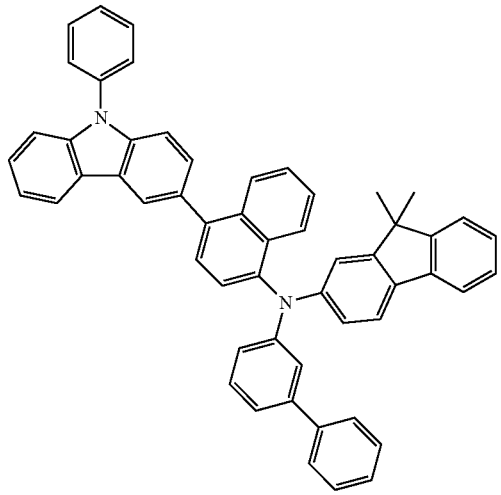

-continued
HT11
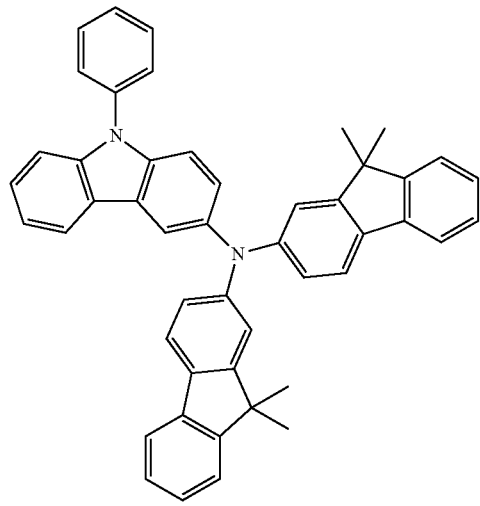
HT12
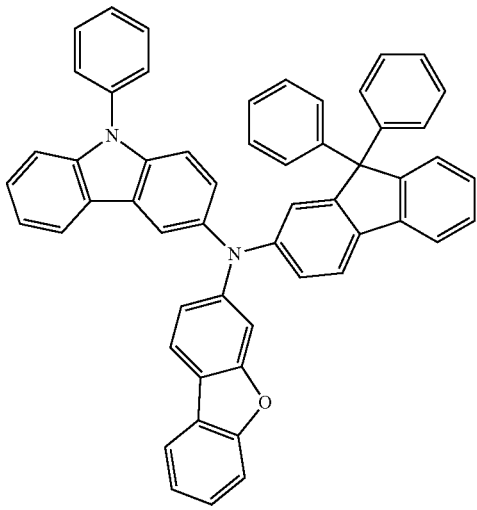
HT13
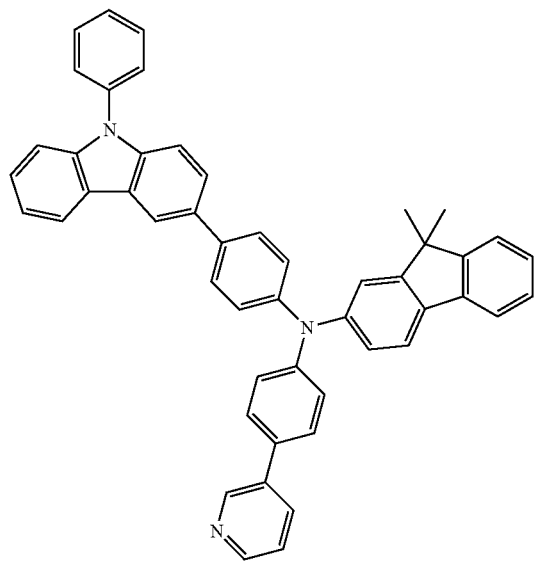
HT14
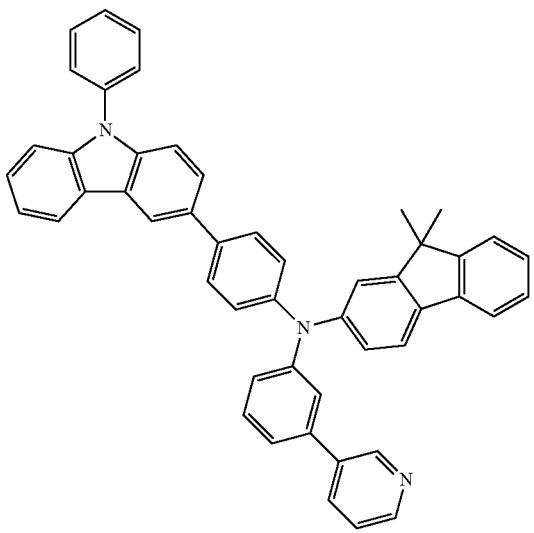
HT15
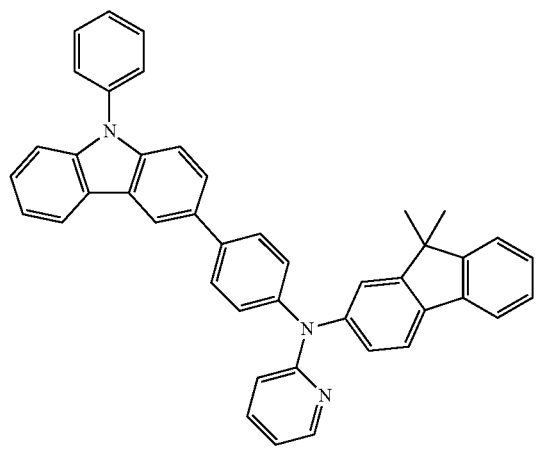
HT16
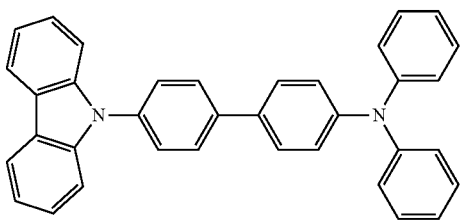

-continued
HT17
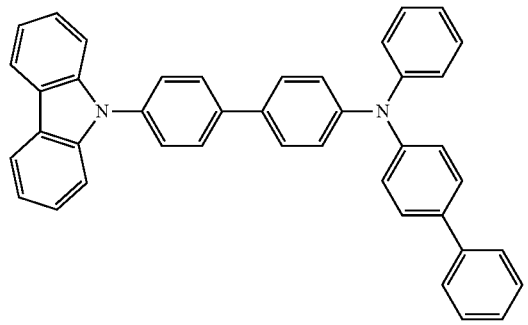
HT18
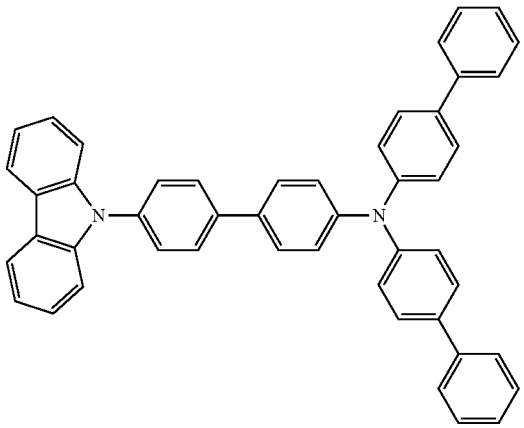
HT19
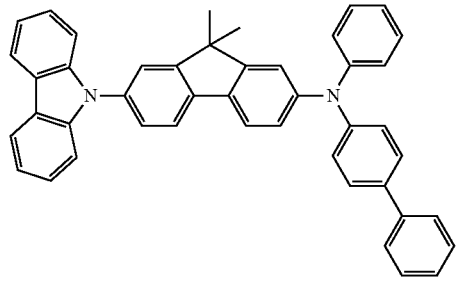
HT20
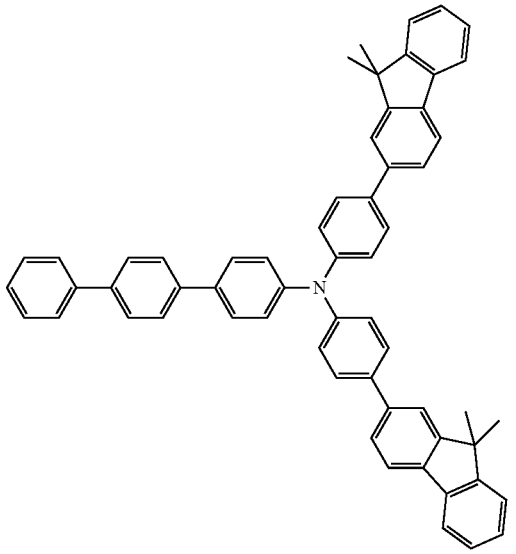
HT21
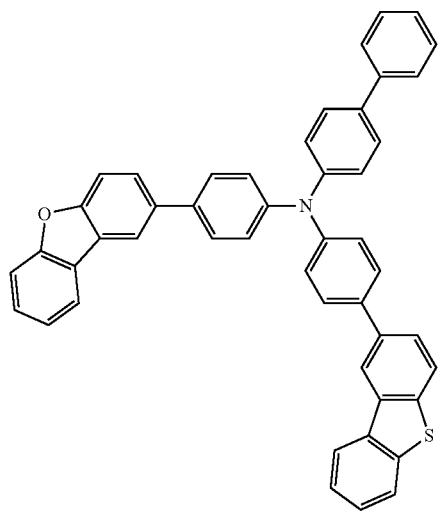
HT22
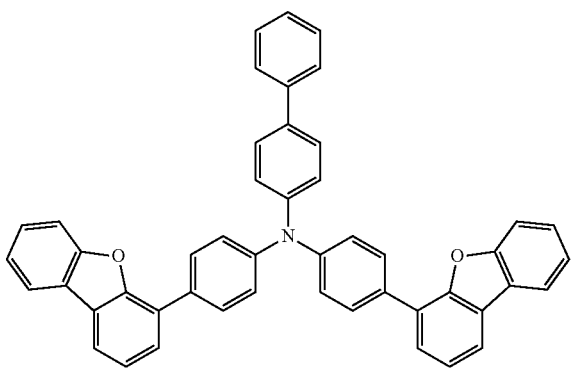

HT23
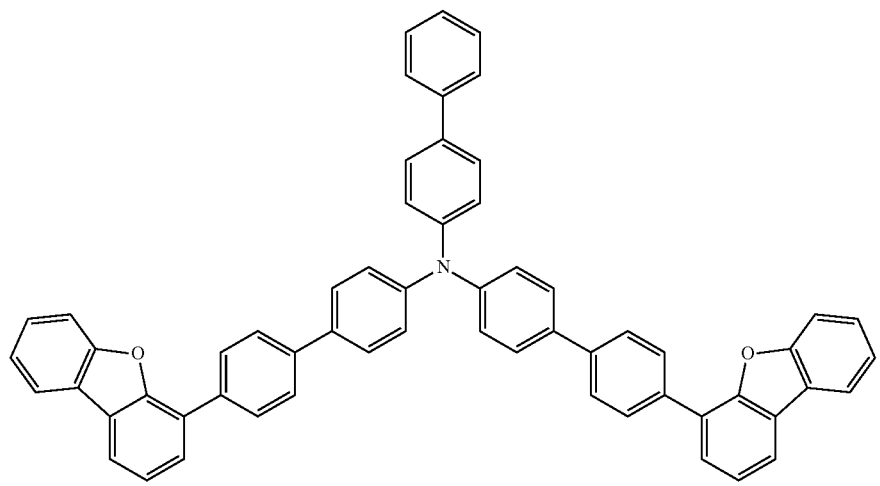
HT24 HT25
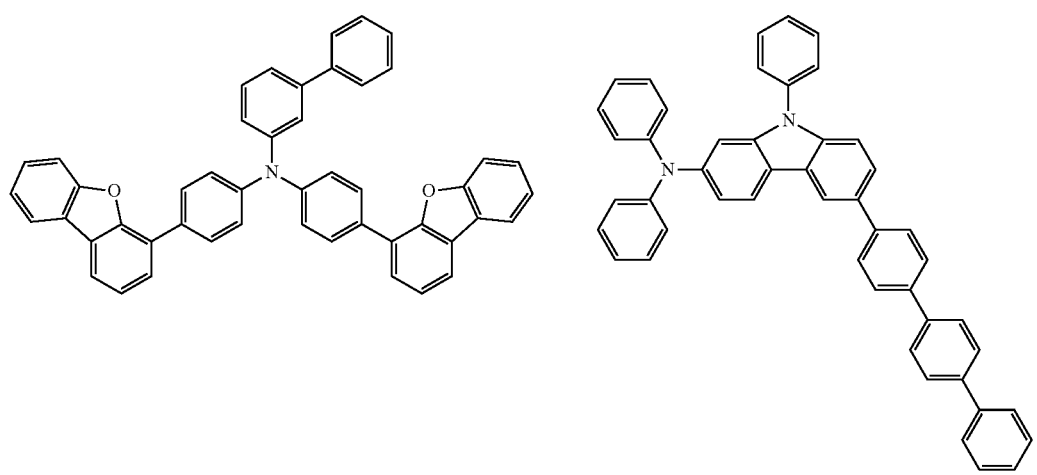
HT26 HT27
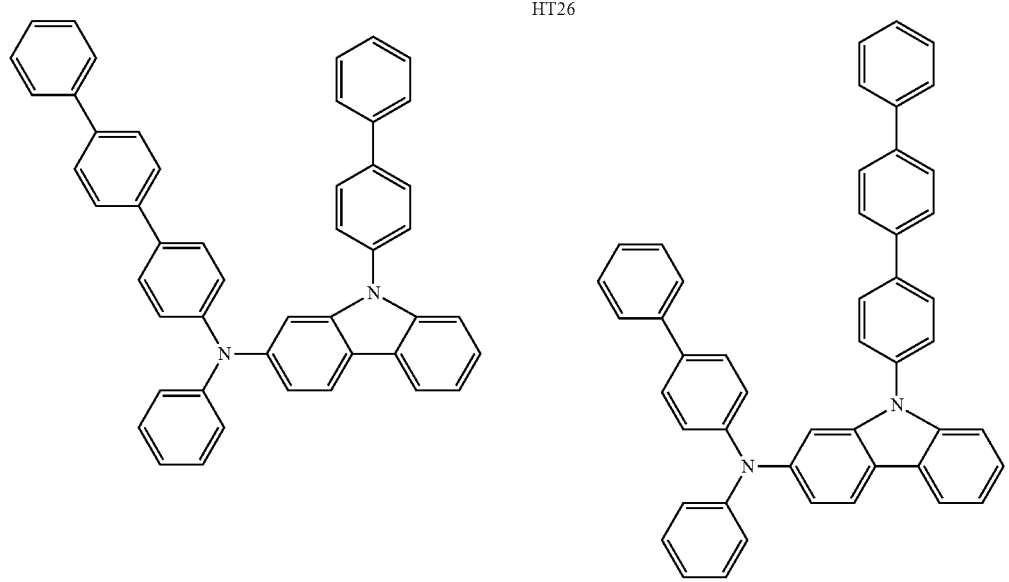

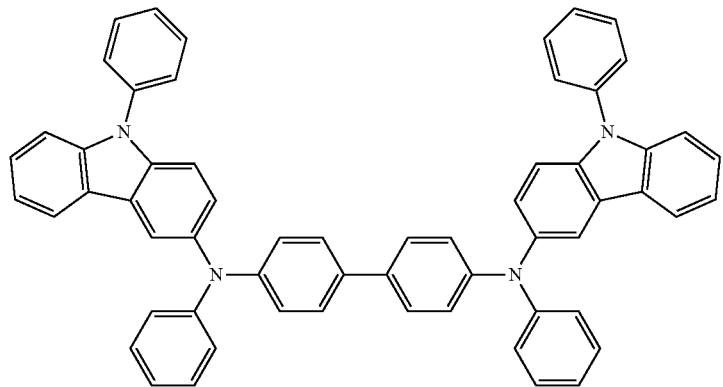
HT28
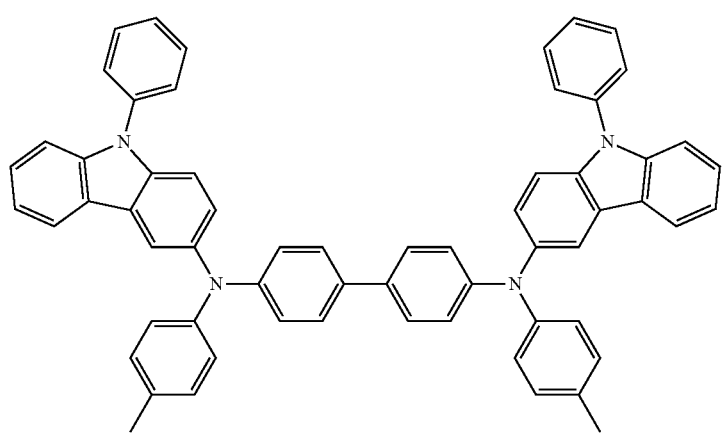
HT29
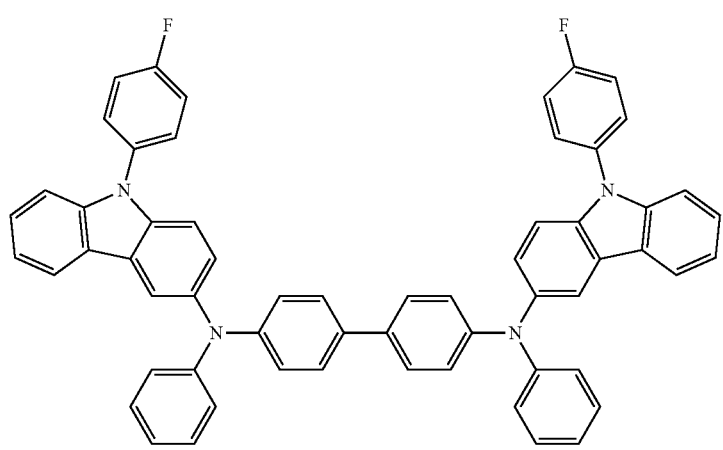
HT30

-continued
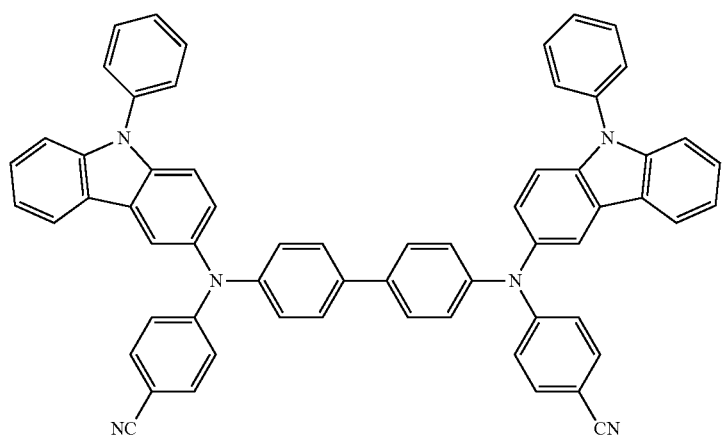
HT31
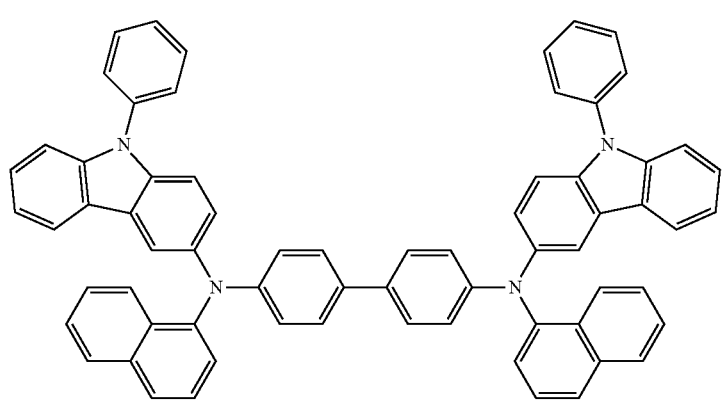
HT32
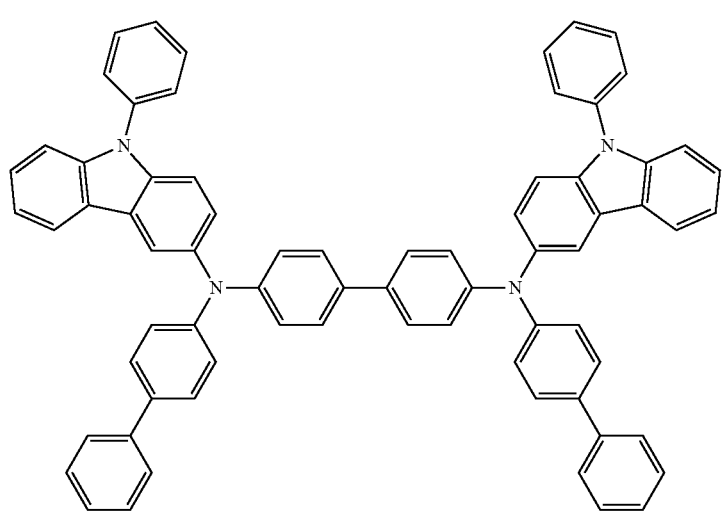
HT33

-continued

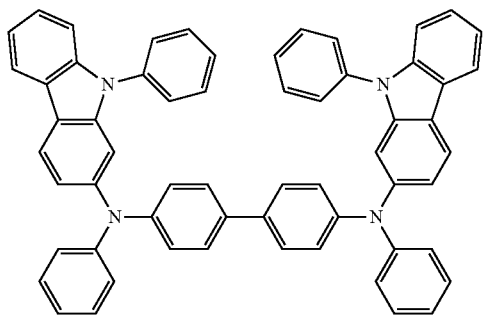
HT34

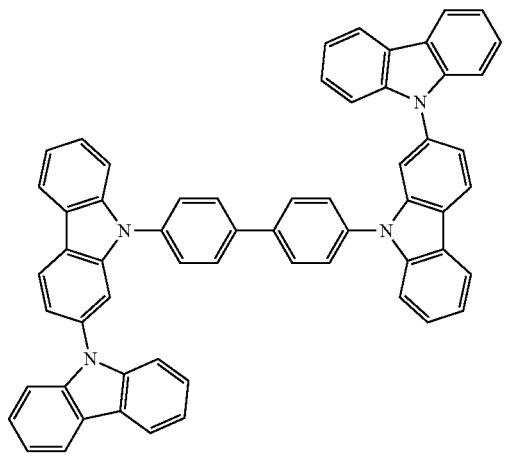
HT35

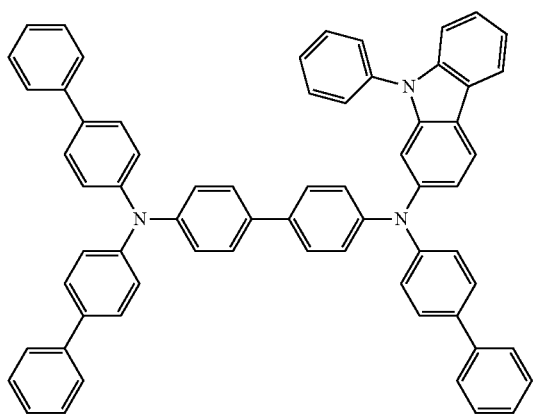
HT36

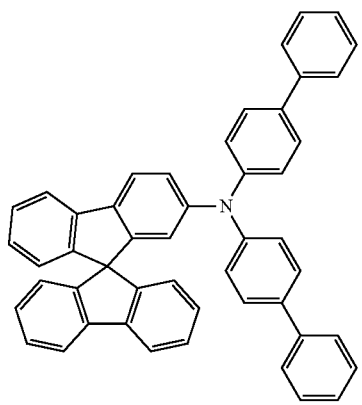
HT37

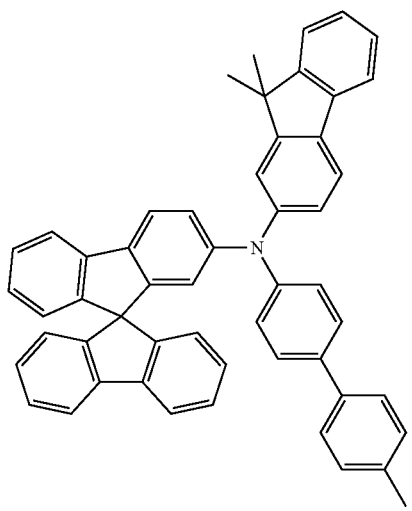
HT38

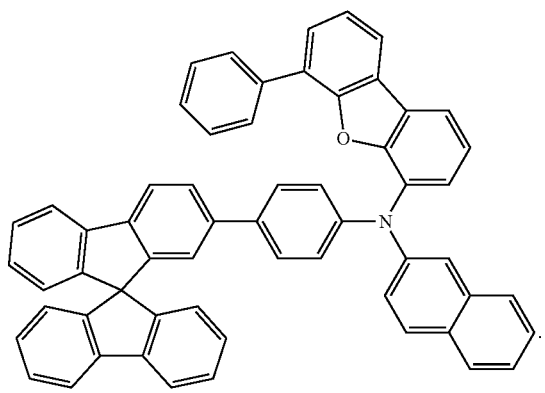
HT39

A thickness of the hole transport region may be in a range of about 100 Å to about 10,000 Å, for example, about 100 Å to about 1,000 Å. When the hole transport region includes at least one selected from a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of the light emitted by the emission layer, and the electron blocking layer may block or reduce the flow of electrons from the electron transport region. The emission auxiliary layer and the electron blocking layer may include any of the materials described above.

P-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In an embodiment, a lowest unoccupied molecular orbital (LUMO) of the p-dopant may be −3.5 eV or less.

The p-dopant may be one selected from a quinone derivative, a metal oxide, and a cyano group-containing compound, but embodiments of the p-dopant are not limited thereto.

For example, the p-dopant may include at least one selected from:

a quinone derivative, such as tetracyanoquinodimethane (TCNQ) and 2,3,5,6-tetrafluoro-7,7,8,8-tetracyanoquinodimethane (F4-TCNQ);

a metal oxide, such as a tungsten oxide and a molybdenum oxide;

1,4,5,8,9,11-hexaazatriphenylene-hexacarbonitrile (HAT-CN); and a compound represented by Formula 221, but embodiments of the p-dopant are not limited thereto:

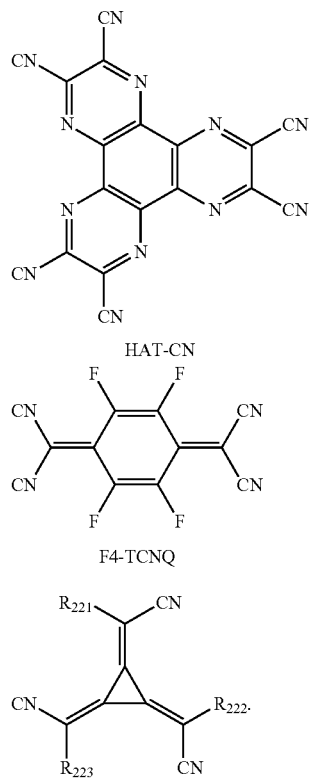

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer of Organic Layer 150

When the organic light-emitting device 10 is a full color organic light-emitting device, the emission layer may be patterned into a red emission layer, a green emission layer, and a blue emission layer, according to an individual subpixel. In various embodiments, the emission layer may have a stacked structure of two or more layers selected from a red emission layer, a green emission layer, and a blue emission layer, in which the two or more layers contact (e.g., physically contact) each other or are separated from each other. In various embodiments, the emission layer may include two or more materials selected from a red-light emission material, a green-light emission material, and a blue-light emission material, in which the two or more materials are mixed with each other in a single layer to emit white light.

The emission layer may include a host and a dopant. The dopant may include at least one selected from a phosphorescent dopant and a fluorescent dopant.

In the emission layer, an amount of the dopant may be generally in a range of about 0.01 to about 15 parts by weight based on 100 parts by weight of the host, but embodiments of the emission layer are not limited thereto.

A thickness of the emission layer may be in a range of about 100 Å to about 1,000 Å, for example, about 200 Å to about 600 Å. When the thickness of the emission layer is within these ranges, excellent light-emission characteristics may be obtained without a substantial increase in driving voltage.

Host of Emission Layer

The host may include a compound represented by Formula 301:

$$[Ar_{301}]_{xb11}-[(L_{301})_{xb1}-R_{301}]_{xb21}. \quad \text{Formula 301}$$

In Formula 301, $Ar_{301}$ may be a substituted or unsubstituted $C_5$-$C_{60}$ carbocyclic group or a substituted or unsubstituted $C_1$-$C_{60}$ heterocyclic group, Xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer selected from 0 to 5, $R_{301}$ may be selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer selected from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and, $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the host are not limited thereto.

In Formula 301, when xb11 is 2 or more, a plurality of $Ar_{301}$(s) may be linked through a single bond, or a plurality of single bonds (e.g., a first $Ar_{301}$ may be linked to a second $Ar_{301}$ via a first single bond, the second $Ar_{301}$ may be linked to a third $Ar_{301}$ via a second single bond, and so forth).

In various embodiments, the compound represented by Formula 301 may be represented by Formula 301-1 or Formula 301

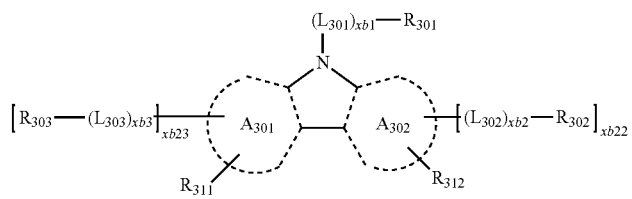

Formula 301-1

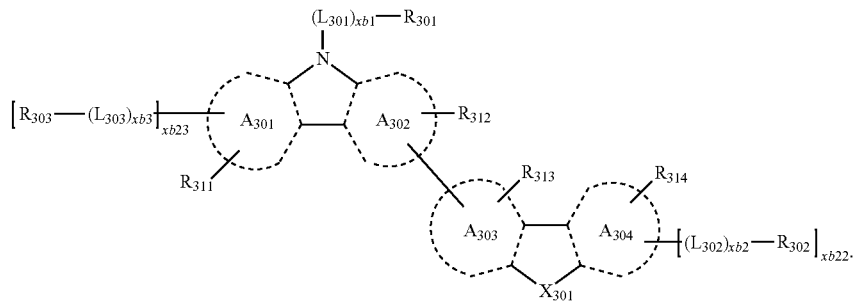

Formula 301-2

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), In an embodiment, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydraxb22 and xb23 may each independently 0, 1, or 2, $L_{301}$, xb1, $R_{301}$, and $Q_3$, to $Q_{33}$ may each independently be the same as described herein in connection with those provided in the present disclosure (e.g., $L_{301}$, xb1, $R_{301}$, and $Q_{31}$ to $Q_{33}$ may be the same as described herein in connection with Formula 301), $L_{302}$ to $L_{304}$ may each independently be the same as described herein in connection with $L_{301}$ (e.g., $L_{302}$ to $L_{304}$ may be the same as $L_{301}$ as described herein in connection with Formula 301), Xb2 to xb4 may each independently be the same as described herein in connection with xb1 (e.g., xb2 to xb4 may be the same as xb1 as described herein in connection with Formula 301), and $R_{302}$ to $R_{304}$ may each independently be the same as described herein in connection with $R_{301}$ (e.g., $R_{302}$ to $R_{304}$ may be the same as $R_{301}$ as described herein in connection with Formula 301).

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$ ($Q_{31}$), and —P(=O)($Q_{31}$)($Q_{32}$), and $Q_{31}$ to $Q_{33}$ may each independently be the same as described herein in connection with those provided in the present disclosure (e.g., $Q_{31}$ to $Q_{33}$ may be the same as described herein in connection with Formulae 301).

In various embodiments, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$ ($Q_{31}$), and —P(=O)($Q_{31}$)($Q_{32}$), and $Q_{31}$ to $Q_{33}$ may each independently be the same as described herein in connection with those provided in the present disclosure (e.g., $Q_{31}$ to $Q_{33}$ may be the same as described herein in connection with Formulae 201 and 202).

In various embodiments, the host may include an alkaline earth-metal complex. For example, the host may be selected from a beryllium (Be) complex (for example, Compound H55, shown below), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the host are not limited thereto:

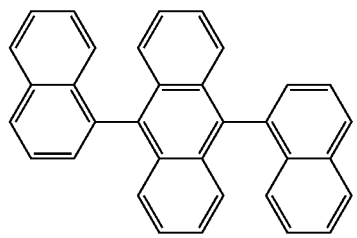

H1

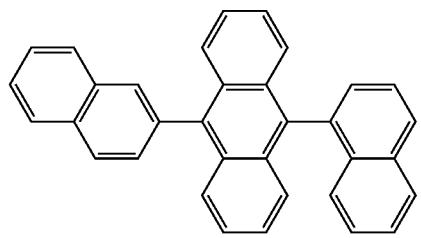

H2

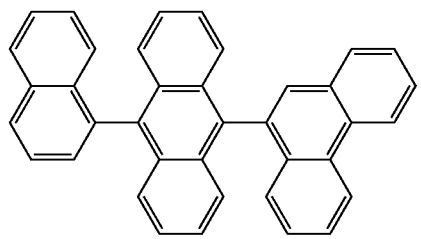

H3

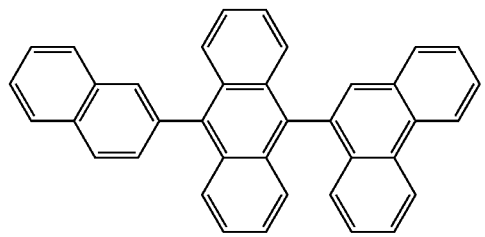

H4

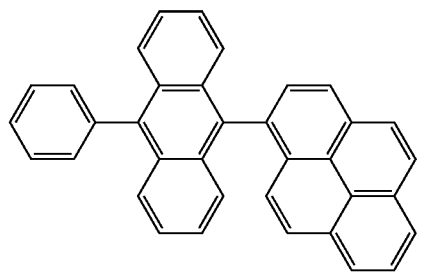

H5

H6 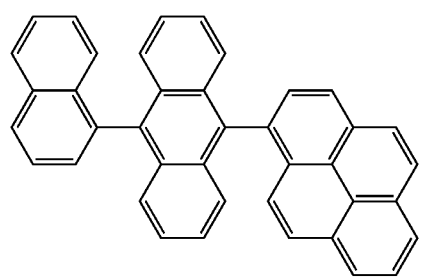
H7 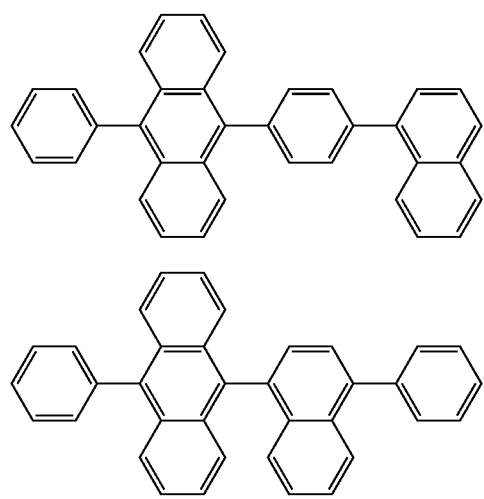
H8
H9 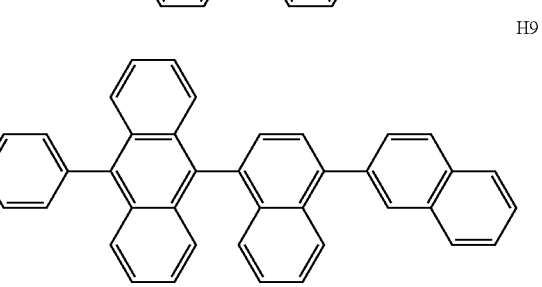
H10 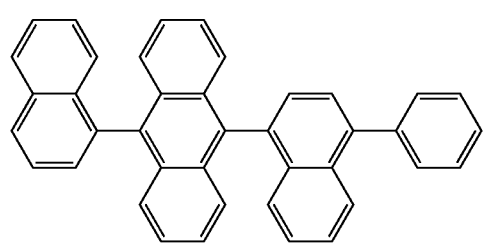
H11 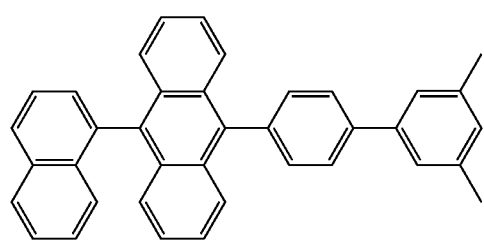
H12 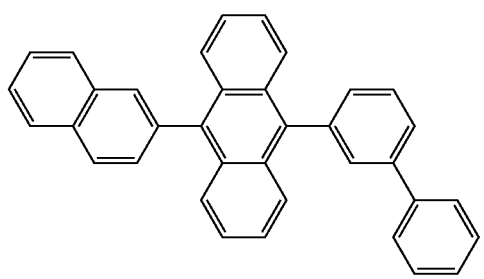
H13 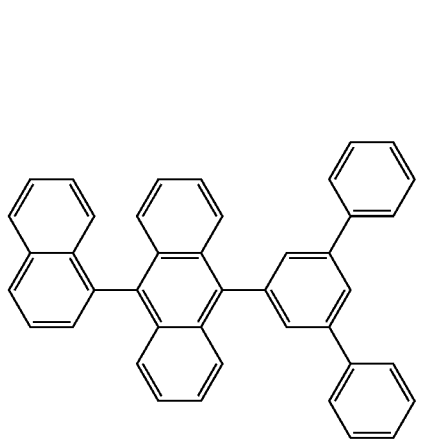
H14 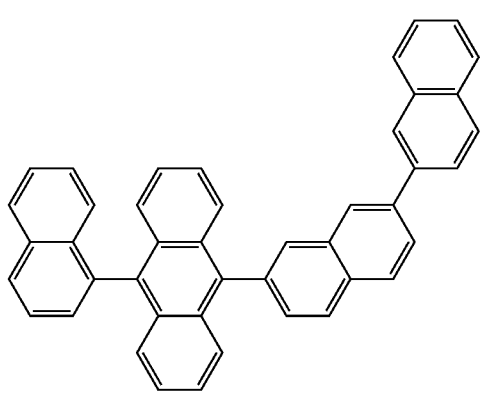
H15 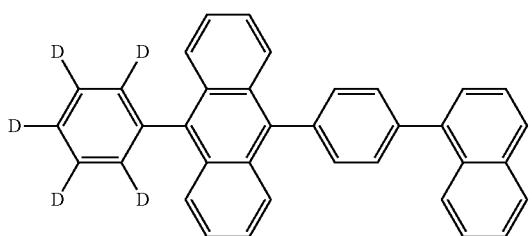
H16 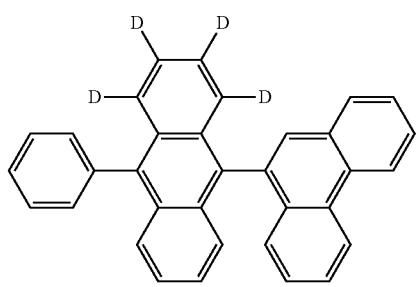

-continued
H17
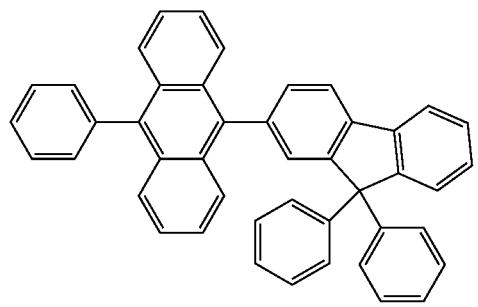
H18
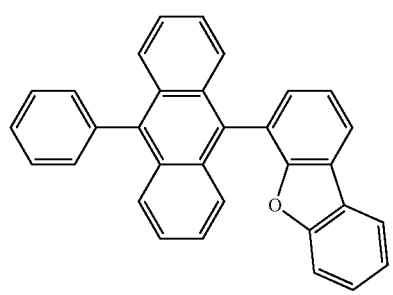
H19
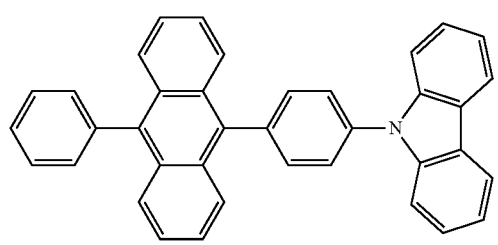
H20
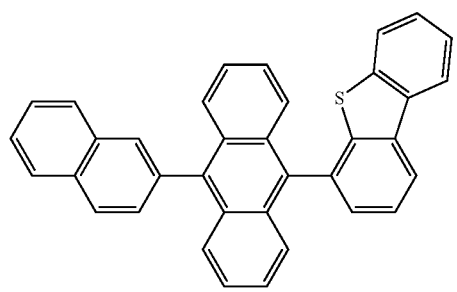
H21
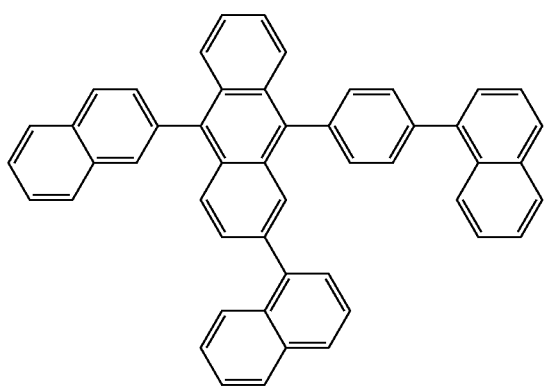
-continued
H22
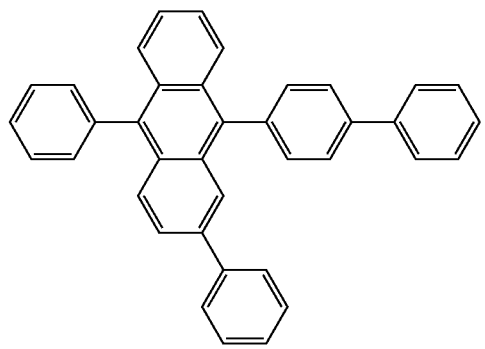
H23
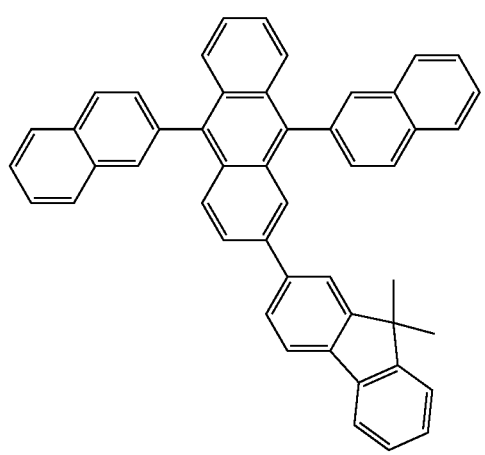
H24
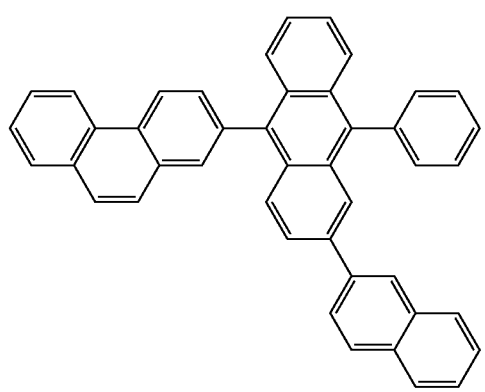

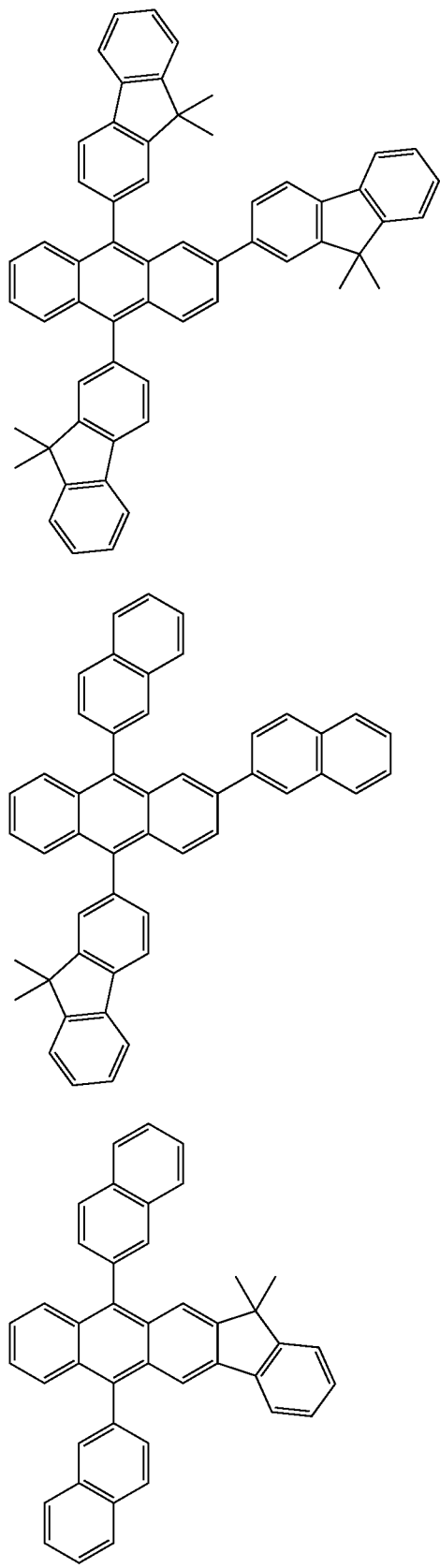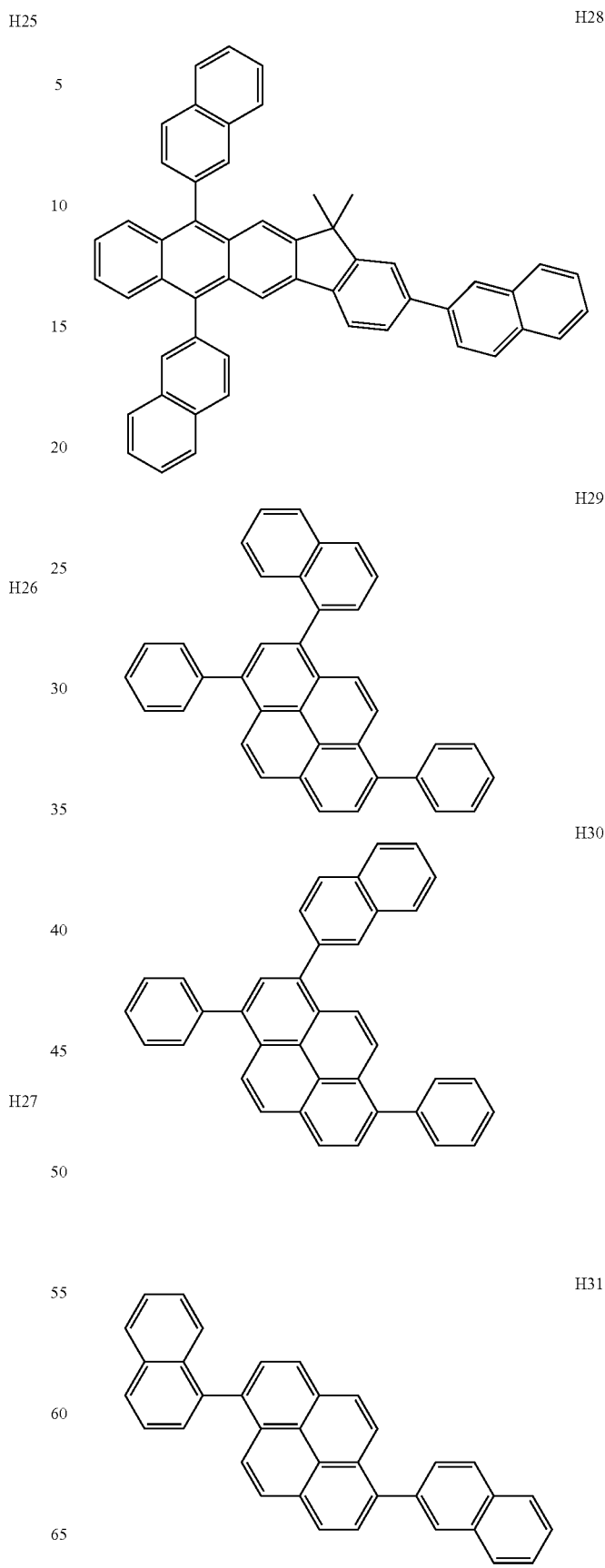

H32
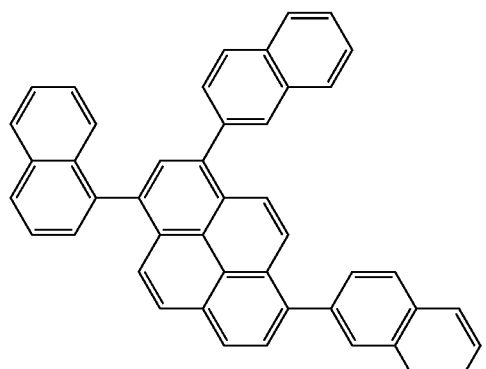
H33
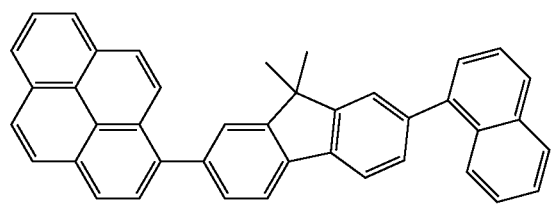
H34
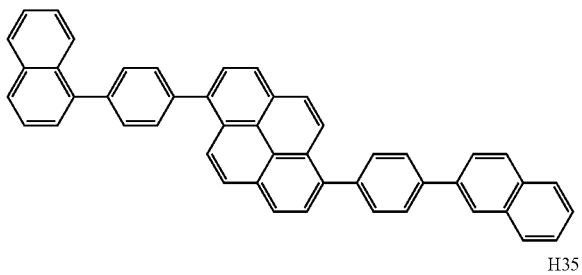
H35
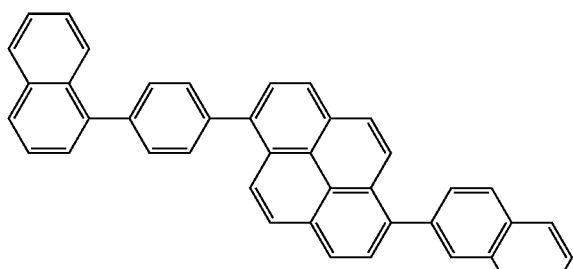
H36
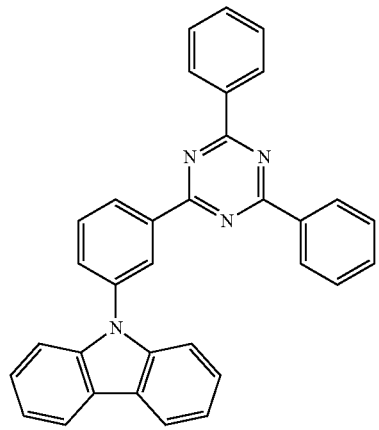
H37
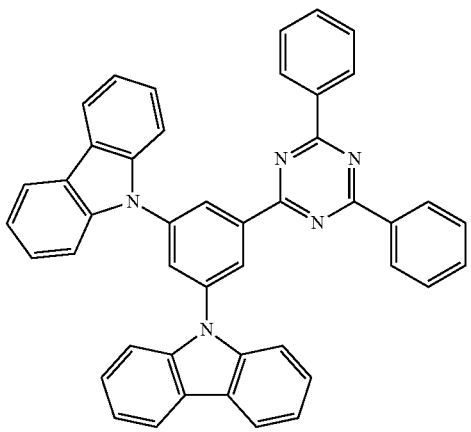
H38
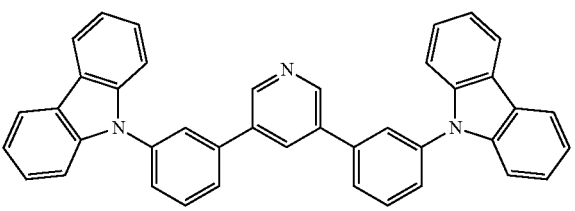
H39
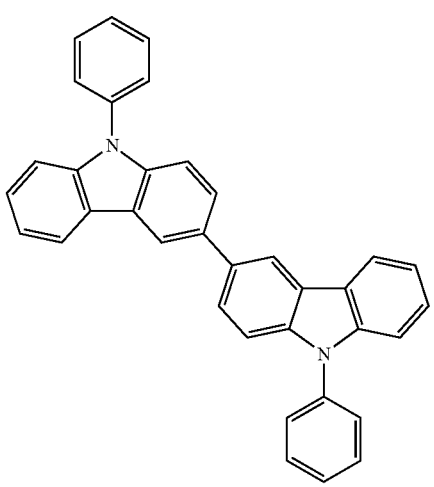

H40
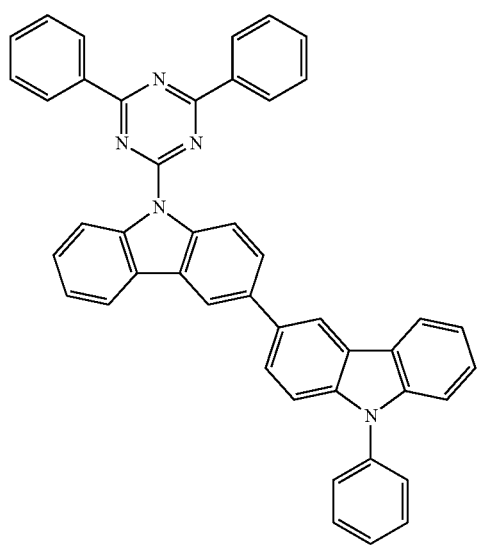
H41
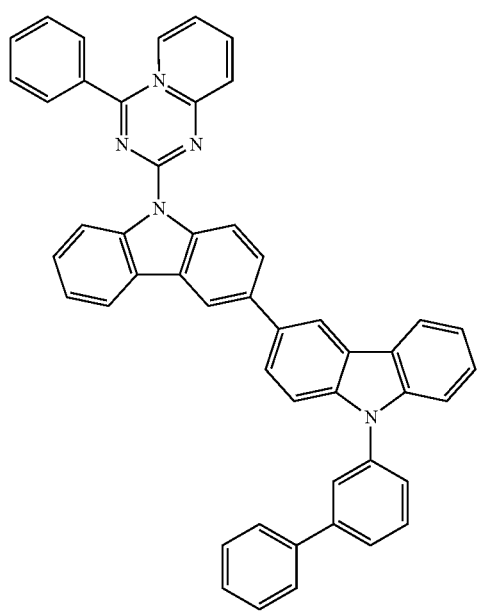
H42
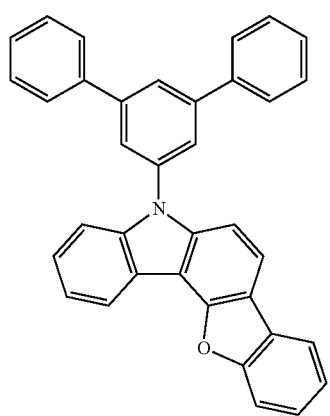
H43
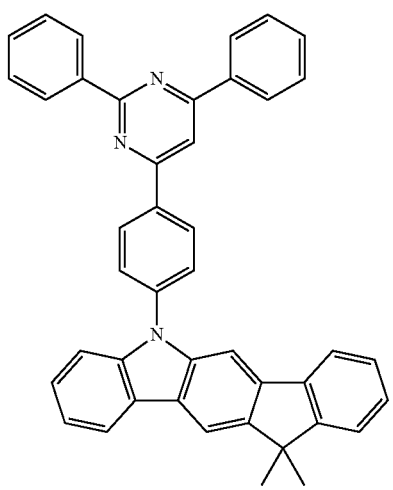
H44
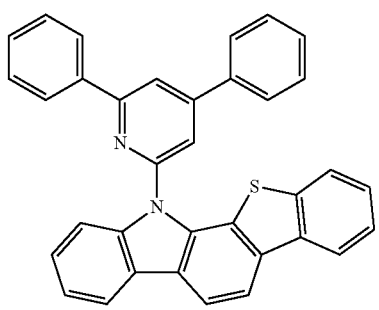
H45
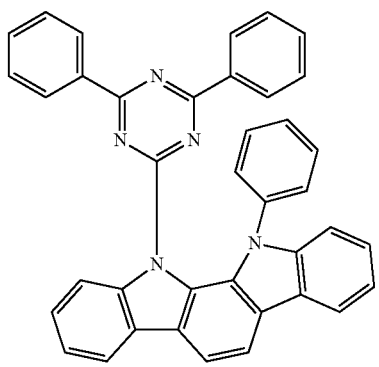
H46
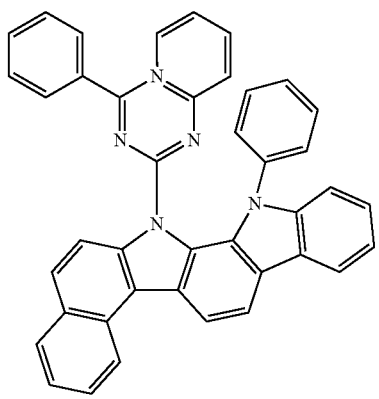

H47
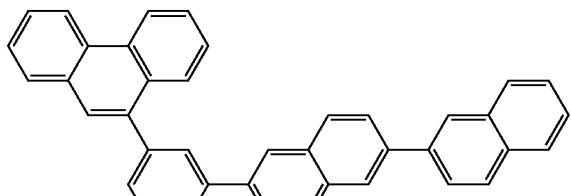
H48
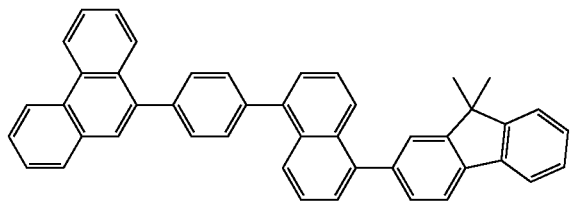
H49
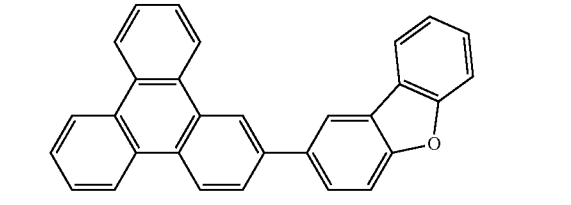
H50
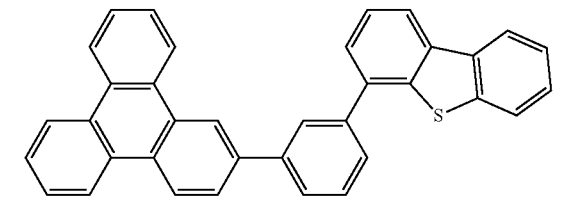
H51
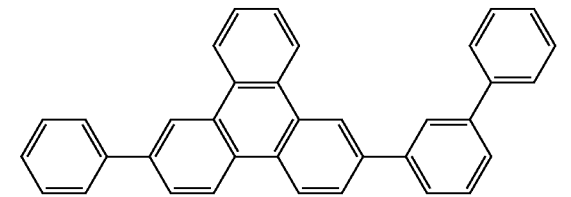
H52
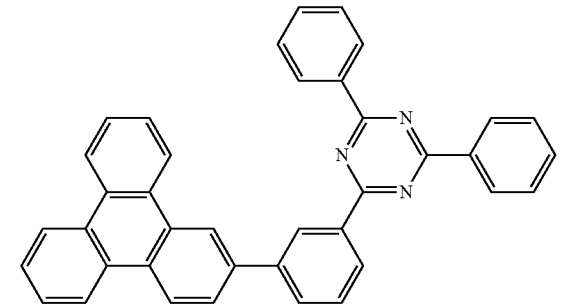
H53
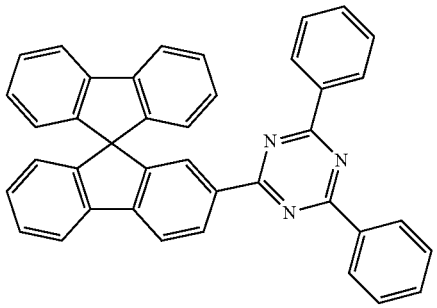
H54
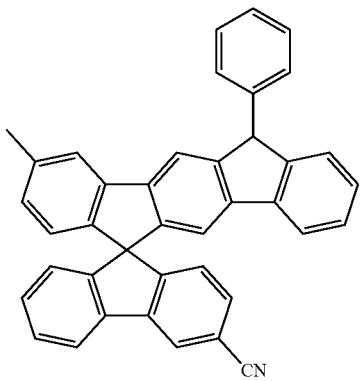
H55
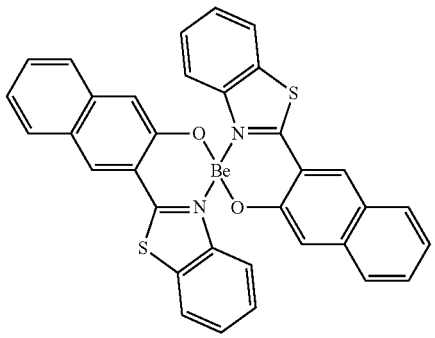
Phosphorescent Dopant of Emission Layer of Organic Layer 150
The phosphorescent dopant may include an organic metal complex represented by Formula 401:
$$M(L_{401})_{xc1}(L_{402})_{xc2}$$ Formula 401
Formula 402
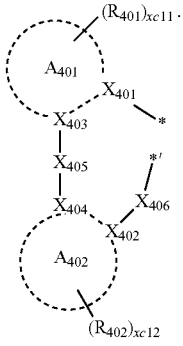

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from a ligand represented by Formula 402, and xc1 may be 1, 2, or 3, provided that when xc1 is 2 or more, a plurality of $L_{401}$(s) may be identical to or different from each other, $L_{402}$ may be an organic ligand, and xc2 may be an integer selected from 0 to 4, provided that when xc2 is 2 or more, a plurality of $L_{402}$(s) may be identical to or different form each other, $X_{401}$ to $X_{404}$ may each independently be a nitrogen atom or a carbon atom, $X_{401}$ and $X_{403}$ may be linked to each other through a single bond or a double bond, and $X_{402}$ and $X_{404}$ may be linked to each other through a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)*', *—C($Q_{411}$)=C($Q_{412}$)-*', *—C($Q_{411}$)=*', or *=C($Q_{411}$)—*', provided that $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group (e.g., a hydrazino group), a hydrazono group (e.g., a hydrazino group), a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), provided that $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer selected from 0 to 10, and

* and *' in Formula 402 each indicate a binding site to M in Formula 401.

In an embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In various embodiments, in Formula 402, i) $X_{401}$ may be a nitrogen atom and $X_{402}$ may be a carbon atom, or ii) $X_{401}$ and $X_{402}$ may each be a nitrogen atom.

In various embodiments, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the phosphorescent dopant are not limited thereto.

In various embodiments, in Formula 401, when xc1 is 2 or more, two $A_{401}$(s) selected from a plurality of $L_{401}$(s) may be optionally linked to each other through a linking group, for example, $X_{407}$. In various embodiments, in Formula 401, when xc1 is 2 or more, two $A_{402}$(s) selected from a plurality of $L_{402}$(S) may be optionally linked to each other through a linking group, for example, $X_{406}$ (see, for example, Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C ($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the phosphorescent dopant are not limited thereto.

In Formula 401, $L_{402}$ may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine or phosphite), but embodiments of the phosphorescent dopant are not limited thereto.

In various embodiments, the phosphorescent dopant may be selected from, for example, Compounds PD1 to PD25, but embodiments of the phosphorescent dopant are not limited thereto:

PD1

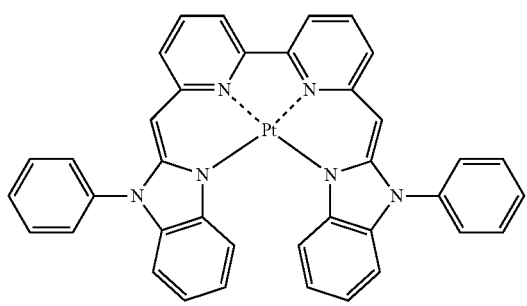

PD2

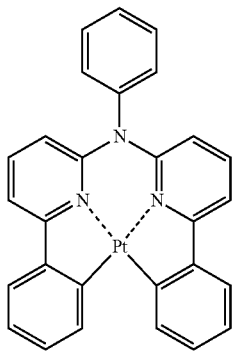

PD3

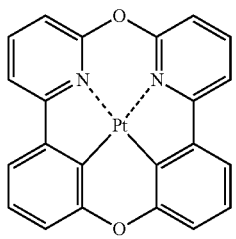

PD4

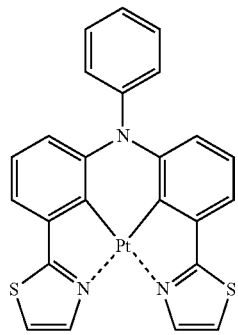

PD5

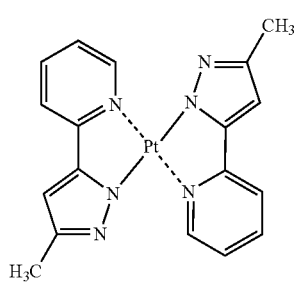

PD6

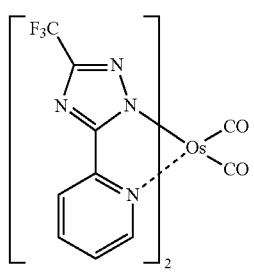

PD7

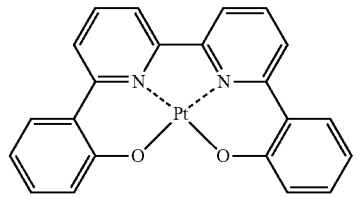

PD8

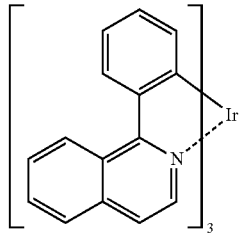

PD9

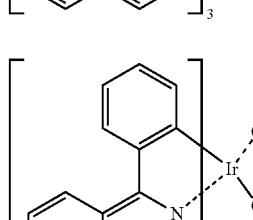

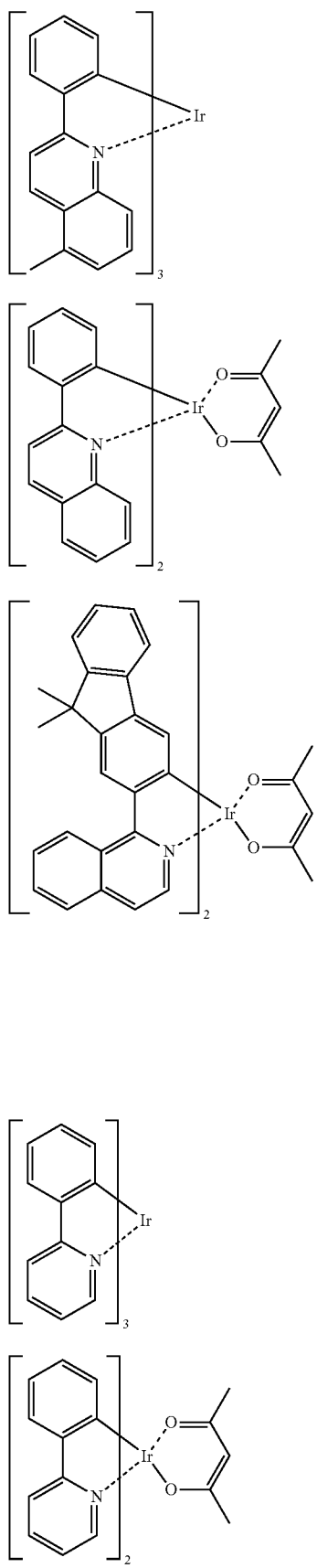
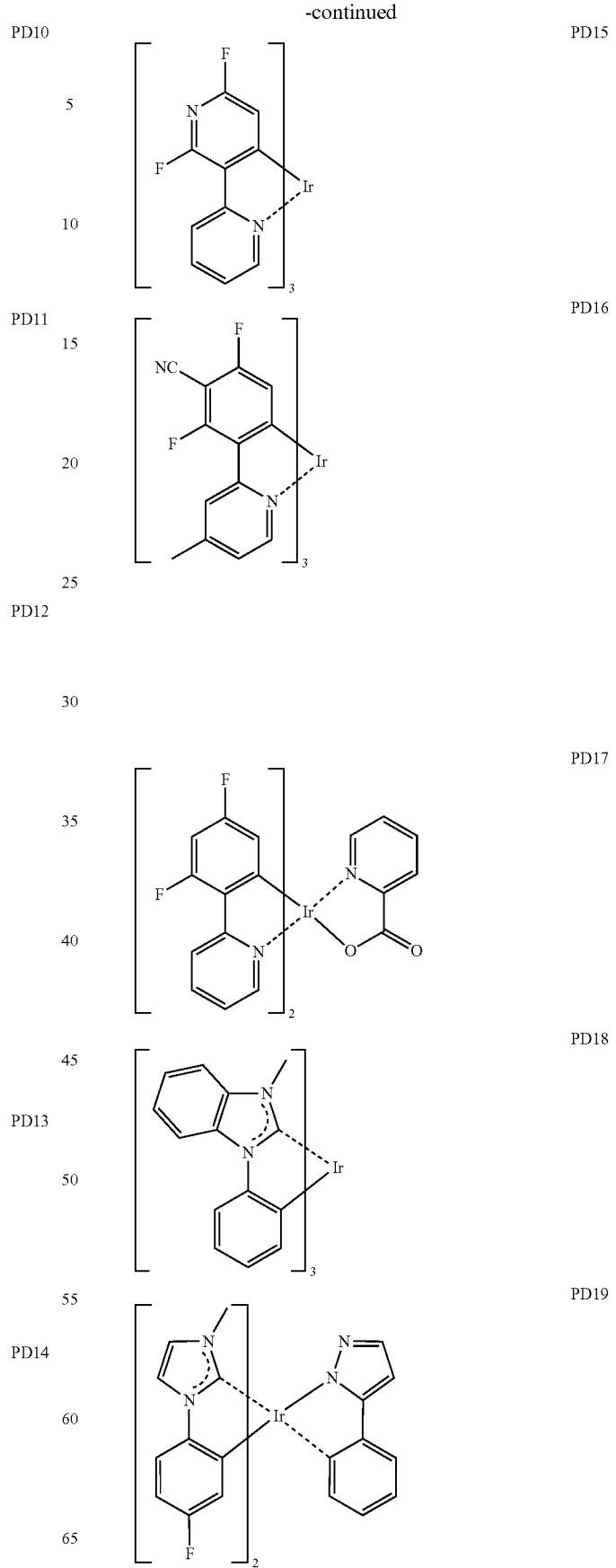

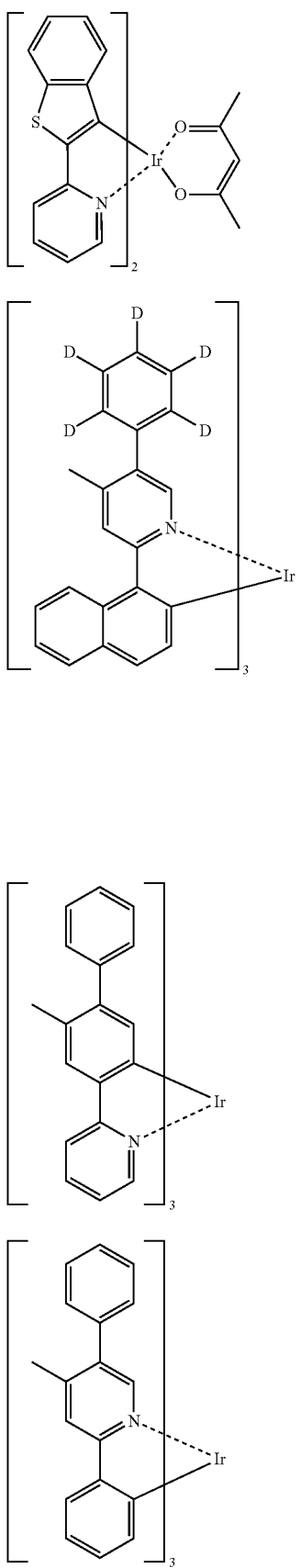

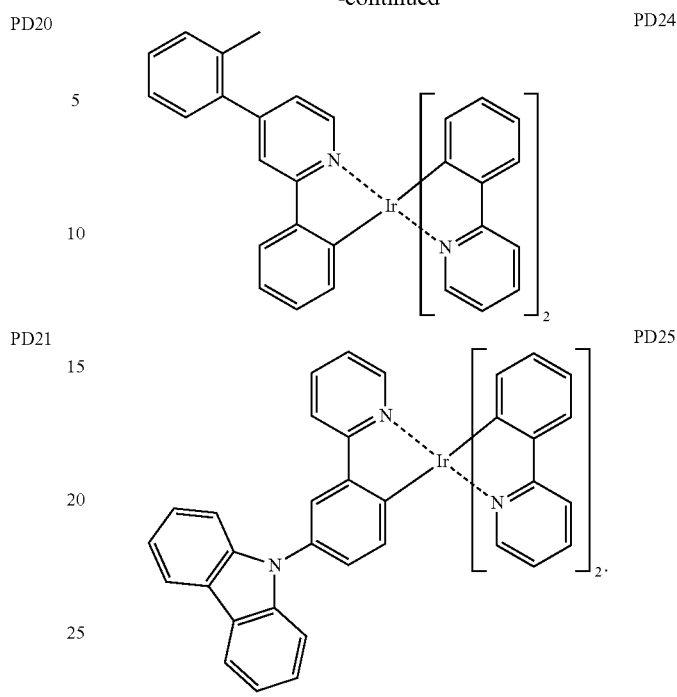

Fluorescent Dopant of Emission Layer

The fluorescent dopant may include an arylamine compound or a styrylamine compound.

The fluorescent dopant may include a compound represented by Formula 501:

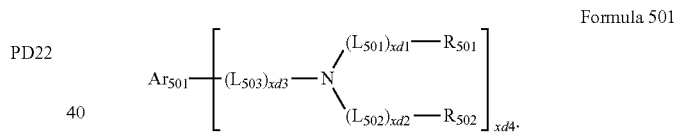

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer selected from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer selected from 1 to 6.

In an embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, and a naphthyl group.

In various embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In various embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In various embodiments, xd4 in Formula 501 may be 2, but embodiments of the fluorescent dopant are not limited thereto.

For example, the fluorescent dopant may be selected from Compounds FD1 to FD22:

FD1 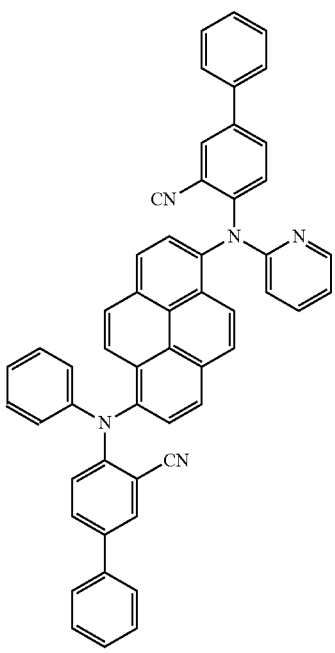
FD2 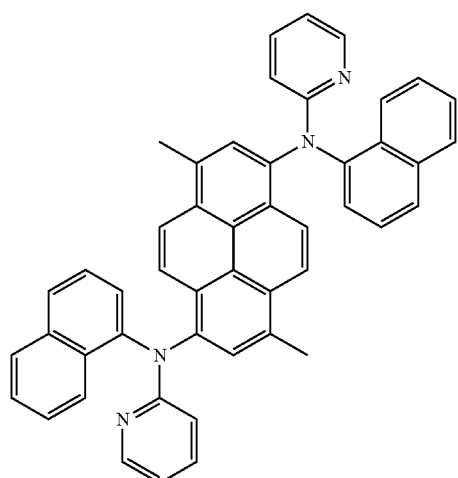
FD3 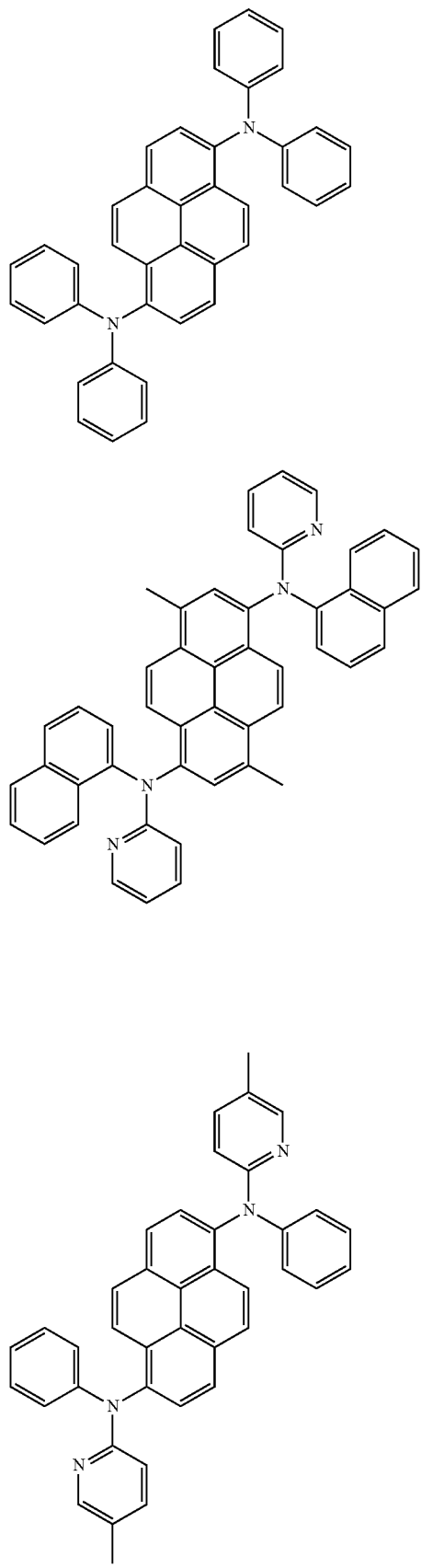
FD4 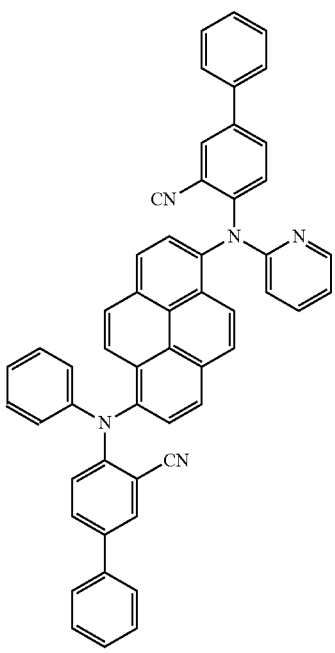
FD5 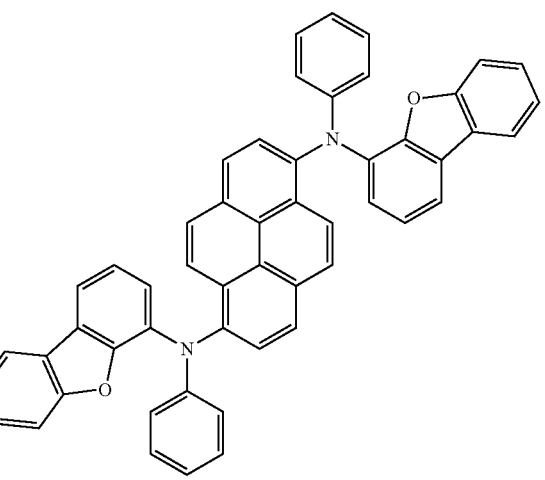
FD6 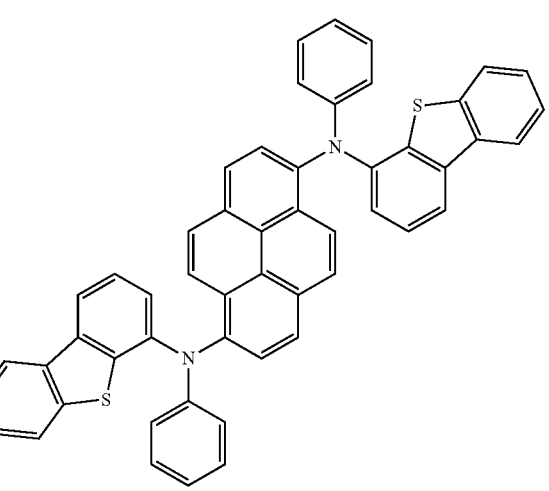

-continued
FD7
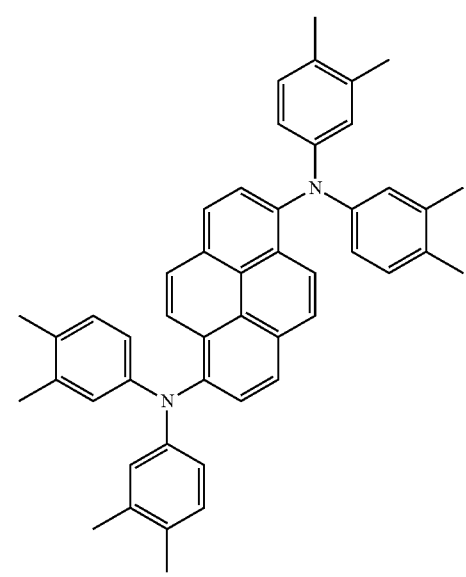
FD8
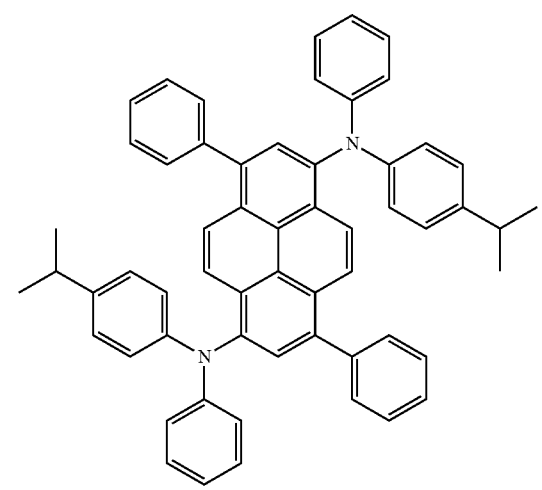
FD9
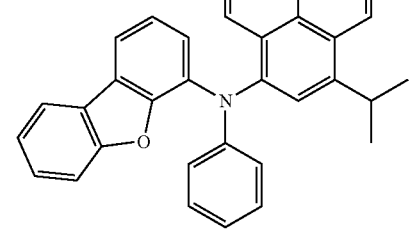
-continued
FD10
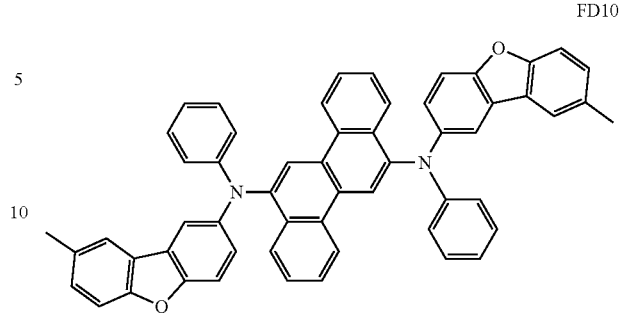
FD11
FD12
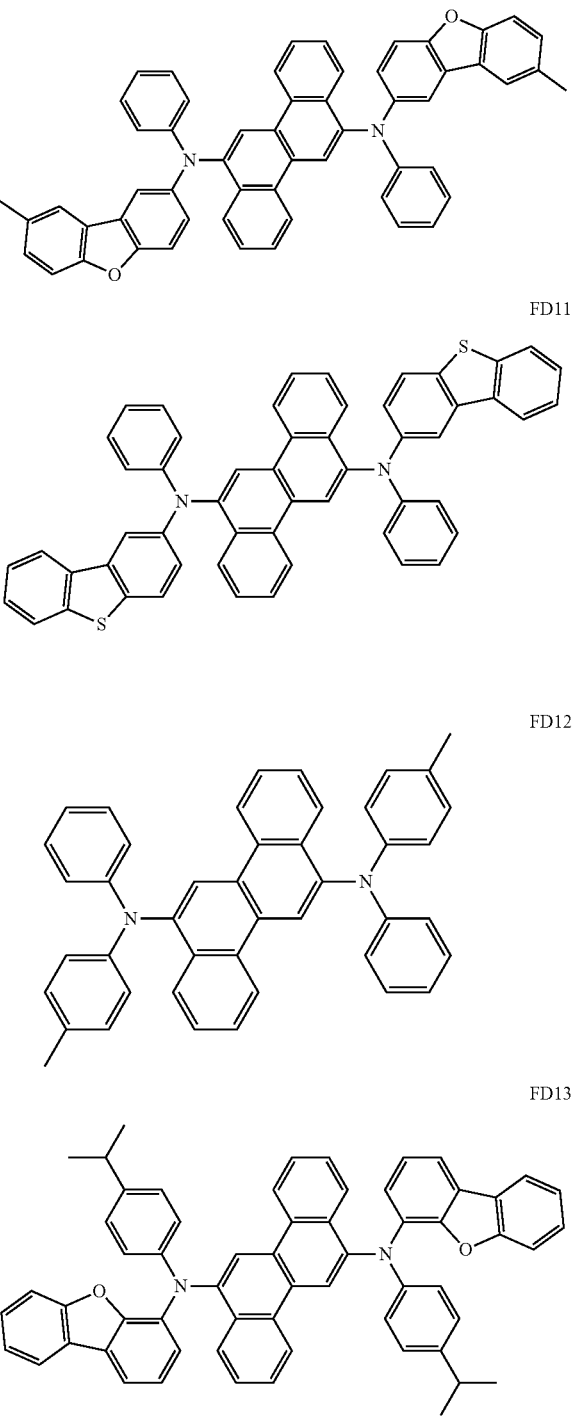
FD13
FD14
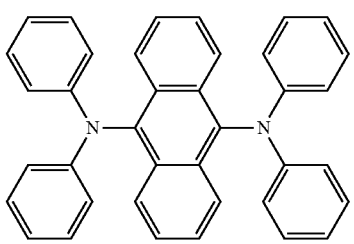

FD15
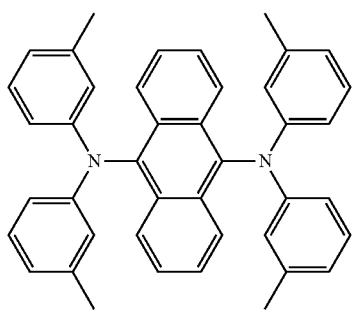
FD16
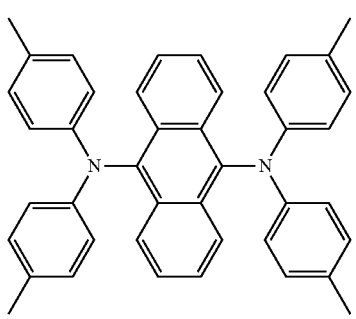
FD17
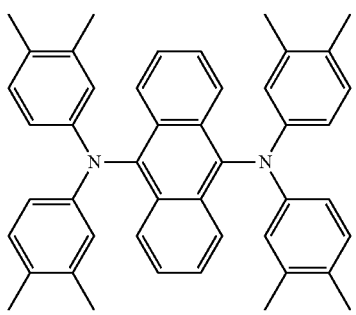
FD18
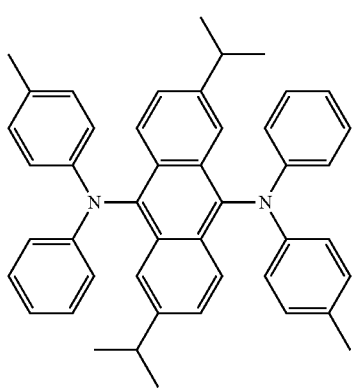
FD19
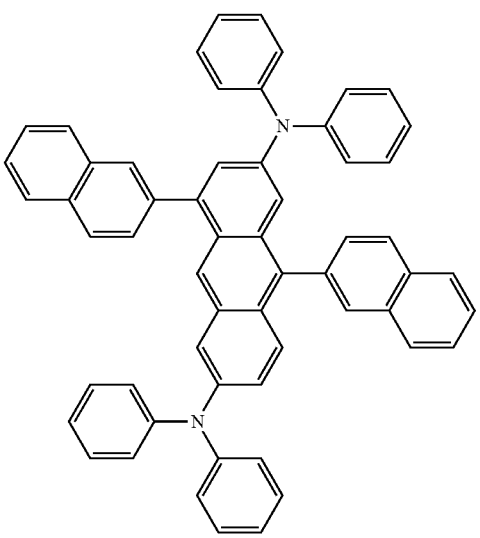
FD20
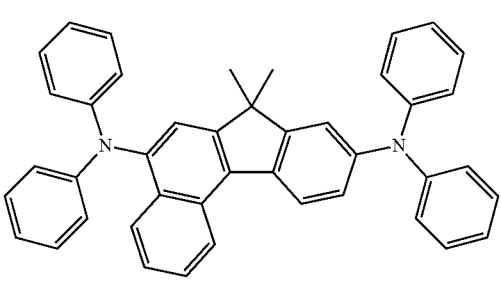
FD21
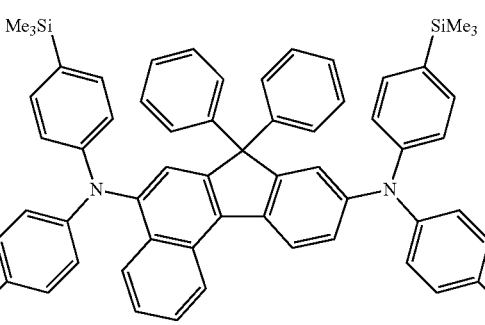
FD22
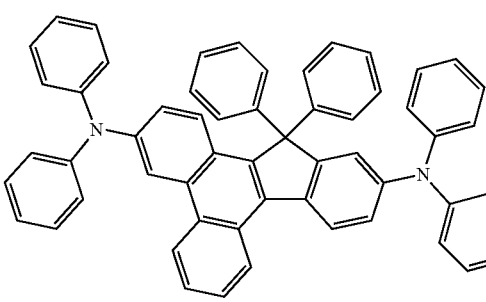
In various embodiments, the fluorescent dopant may be selected from compounds below, but embodiments of the fluorescent dopant are not limited thereto.

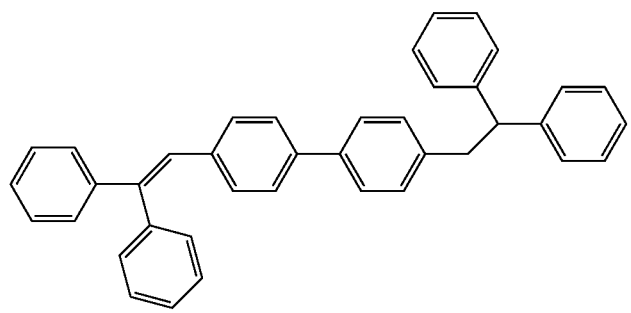
DPVBi
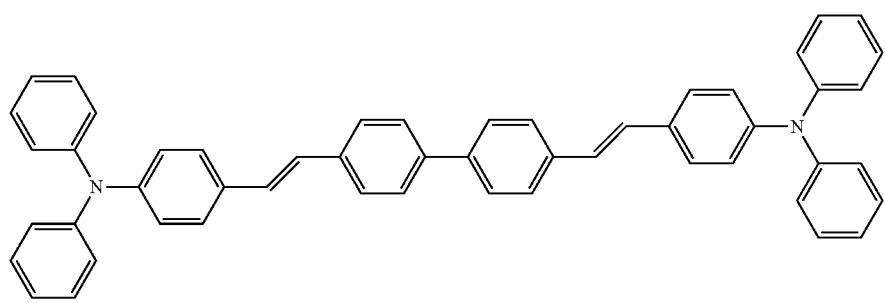
DPAVBi
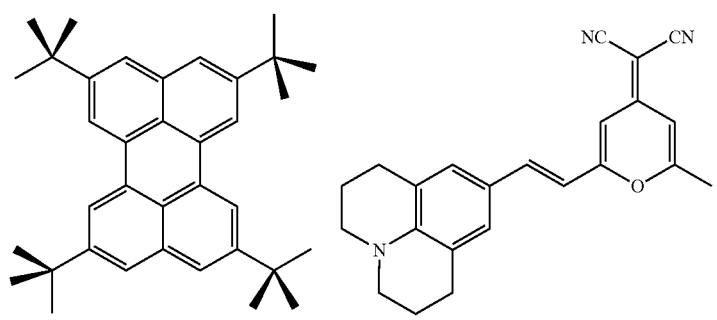
TBPe
DCM
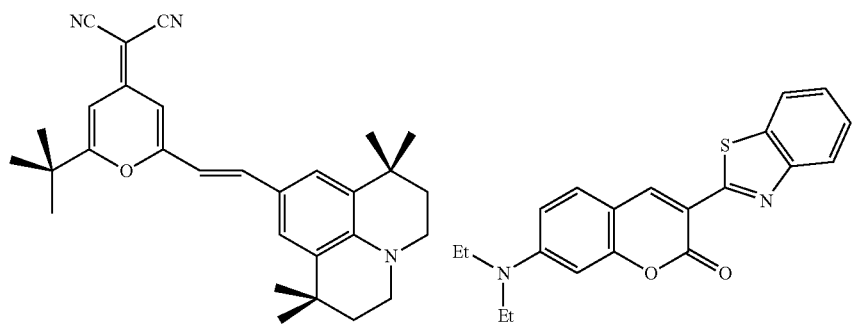
DCJTB
Coumarin 6
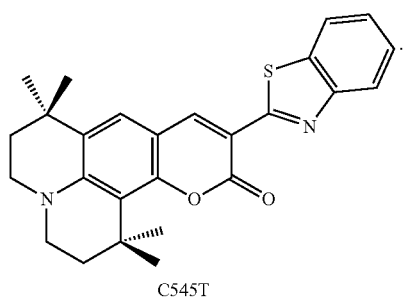
C545T Electron Transport Region of Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include an electron transport layer and at least one layer selected from a buffer layer, a hole blocking layer, an electron control layer, and an electron injection layer, but embodiments of the electron transport region are not limited thereto.

For example, the electron transport region may have a structure of electron transport layer/electron injection layer, a structure of hole blocking layer/electron transport layer/electron injection layer, a structure of electron control layer/electron transport layer/electron injection layer, or a structure of buffer layer/electron transport layer/electron injection layer, wherein for each structure, constituting layers are sequentially stacked from the emission layer in the stated order, but the structure of the electron transport region is not limited thereto.

The electron transport region may include the compound represented by Formula 1 or Formula 2 according to an embodiment. For example, the electron transport layer may include the compound represented by Formula 1 or Formula 2 according to an embodiment.

The electron transport region (for example, a buffer layer, a hole blocking layer, an electron control layer or an electron transport layer in the electron transport region) may include a metal-free compound containing at least one π electron-depleted nitrogen-containing ring.

As used herein, the term "π electron-depleted nitrogen-containing ring" refers to a $C_1$-$C_{60}$ heterocyclic group including at least one *—N=*' moiety as a ring-forming moiety, where * and *' indicate binding sites.

For example, the "π electron-depleted nitrogen-containing ring" may be i) a 5-membered to 7 membered heteromonocyclic group having at least one *—N=*' moiety, ii) a heteropolycyclic group in which at least two or more 5-membered to 7 membered heteromonocyclic groups each having at least one *—N=*' moiety are condensed with each other (e.g., fused together), or iii) a heteropolycyclic group in which at least one 5-membered to 7-membered hetero monocyclic group having at least one *—N=*' moiety is condensed with (e.g., fused together with) at least one $C_5$-$C_{60}$ carbocyclic group, where * and *' indicate binding sites.

Non-limiting examples of the π electron-depleted nitrogen-containing ring may include an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, but embodiments of the π electron-depleted nitrogen-containing ring are not limited thereto.

For example, the electron transport region may further include, in addition to the compound represented by Formula 1 or Formula 2 according to an embodiment, a compound represented by Formula 601:

$$[Ar_{601}]_{xe11}\text{-}[(L_{601})_{xe1}\text{-}R_{601}]_{xe21}. \quad \text{Formula 601}$$

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer selected from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer selected from 1 to 5.

In an embodiment, at least one selected from the xe11 $Ar_{601}$ and at least one selected from the xe21 $R_{601}$ may include the π electron-depleted nitrogen-containing ring as described above.

In an embodiment, in Formula 601, ring $Ar_{601}$ may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, a -phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In Formula 601, when xe11 is 2 or more, 2 or more Ar$_{601}$(s) may be linked to each other through a single bond.

In various embodiments, in Formula 601, A$_{601}$ may include an anthracene group.

In various embodiments, the compound represented by Formula 601 may be represented by Formula 601-1:

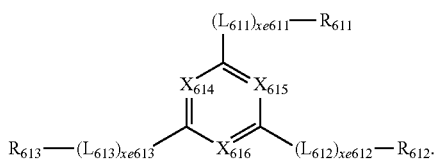

Formula 601-1

In Formula 601-1, $X_{614}$ may be N or C($R_{614}$), $X_{615}$ may be N or C($R_{615}$), and $X_{616}$ may be N or C($R_{616}$), provided that at least one selected from $X_{614}$ to $X_{616}$ is a nitrogen atom, $L_{611}$ to $L_{613}$ may each independently be the same as described herein in connection with $L_{601}$ (e.g., $L_{611}$ to $L_{613}$ may each independently be the same as $L_{601}$ as described in connection with Formula 601), xe611 to xe613 may each independently be the same as described herein in connection with xe1 (e.g., xe611 to xe613 may each independently be the same as xe1 as described in connection with Formula 601), $R_{611}$ to $R_{613}$ may each independently be the same as described herein in connection with $R_{601}$ (e.g., $R_{611}$ to $R_{613}$ may each independently be the same as $R_{601}$ as described in connection with Formula 601), and $R_{614}$ to $R_{616}$ may each independently be selected from hydrogen, deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, and a naphthyl group.

In an embodiment, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the compound represented by one selected from Formulae 601 and 601-1 are not limited thereto.

In various embodiments, in Formulae 601 and 601-1, xe1 and xe611 to xe613 may each independently be 0, 1, or 2.

In various embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ may each independently be the same as described herein in connection with those provided in the present disclosure.

The electron transport region may include at least one compound selected from Compounds ET1 to ET36, but embodiments of the electron transport region are not limited thereto:

ET1
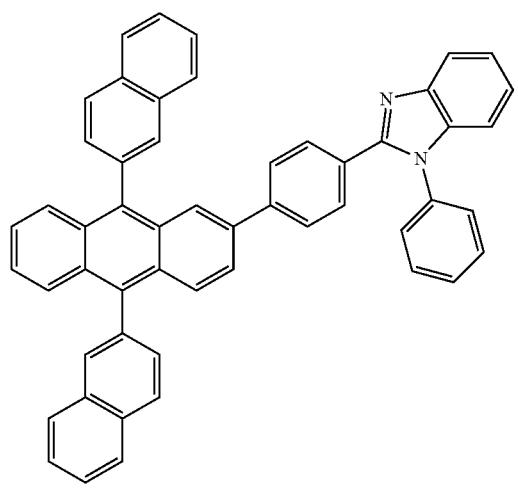
ET2
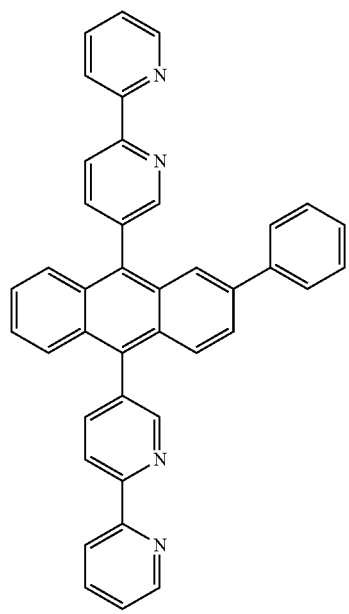
ET3
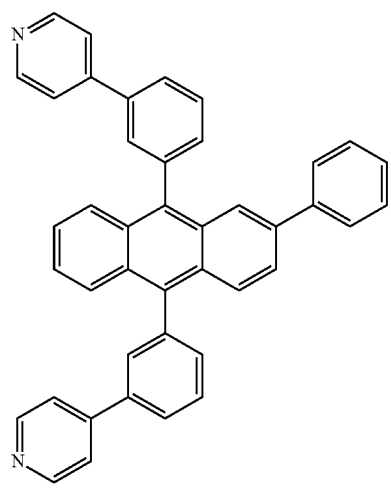
ET4
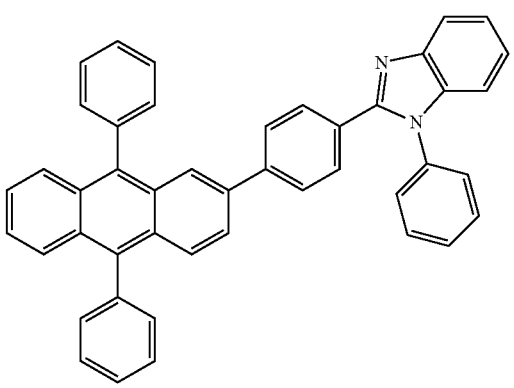
ET5
ET6
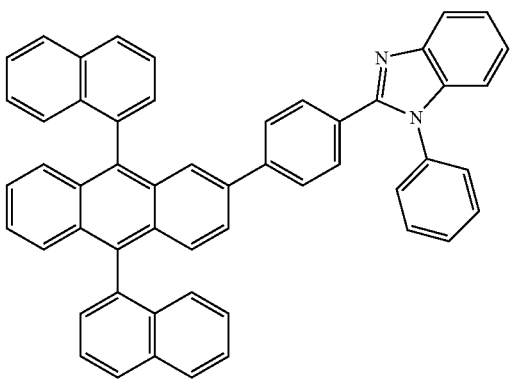

ET7
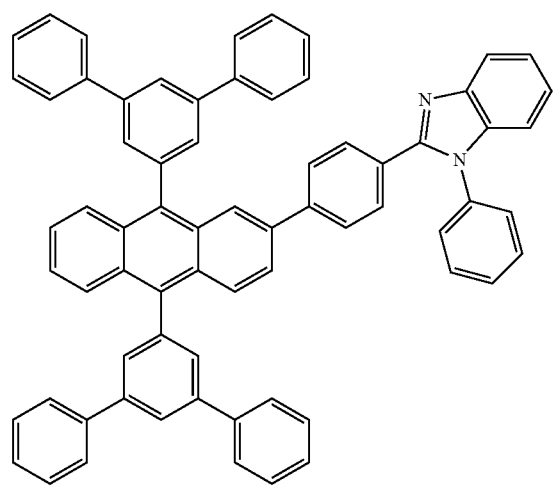
ET8
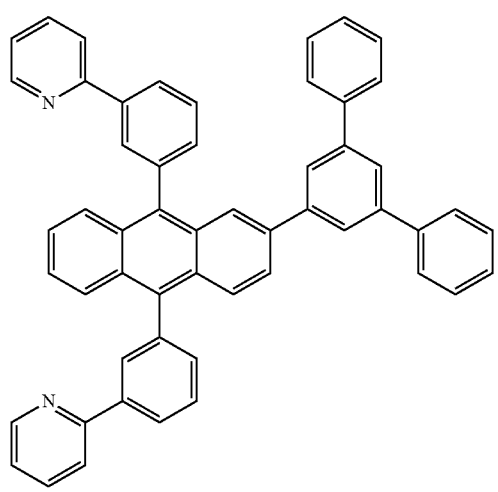
ET9
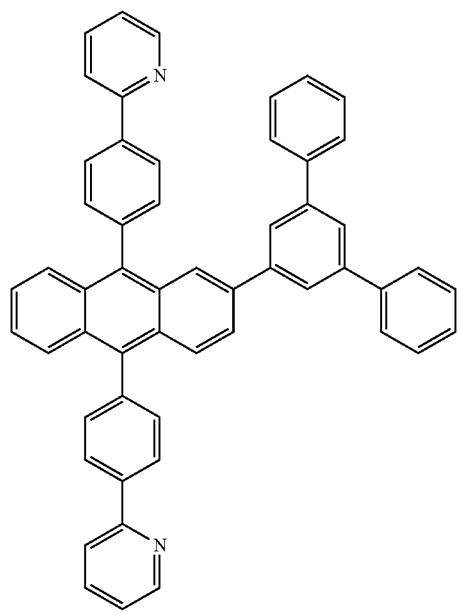
ET10
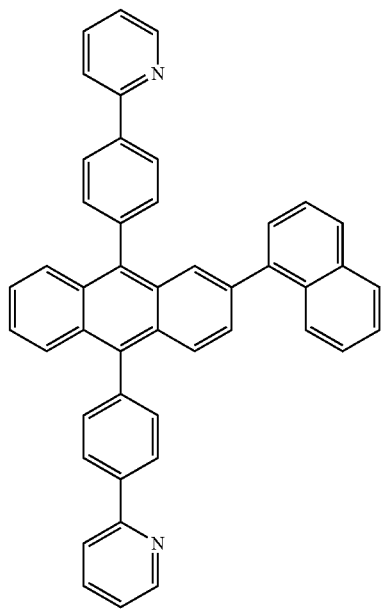
ET11
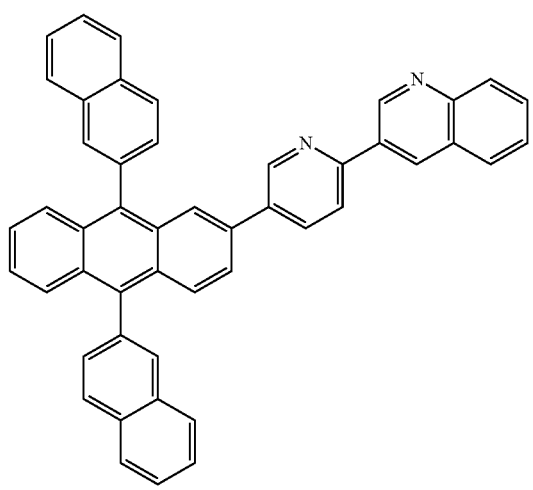
ET12
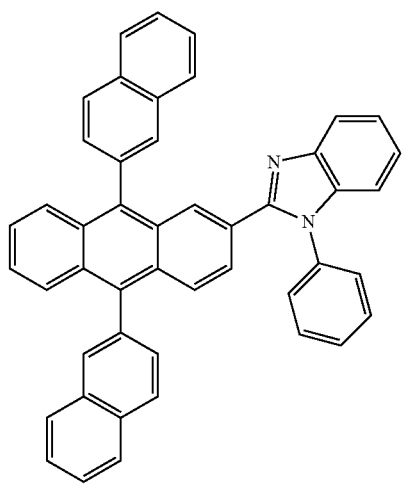

ET13
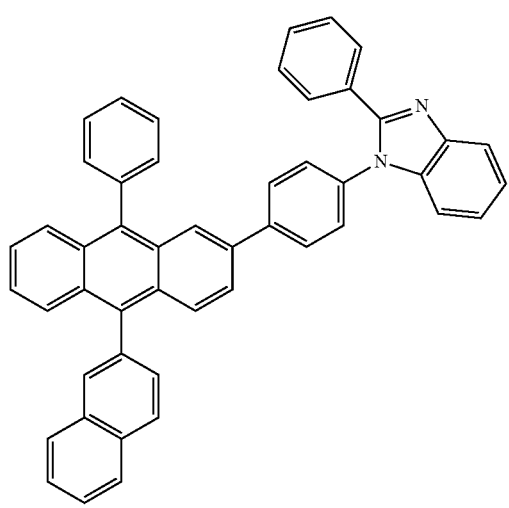
ET14
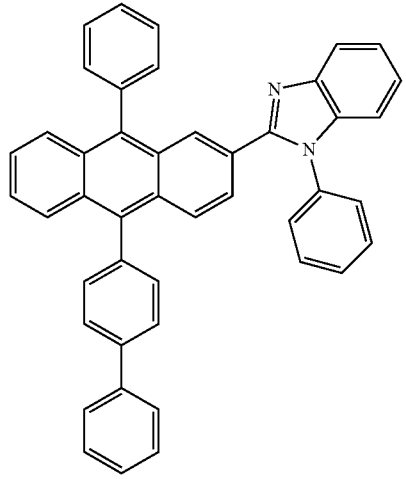
ET15
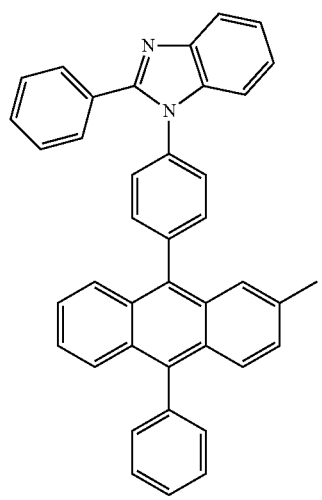
ET16
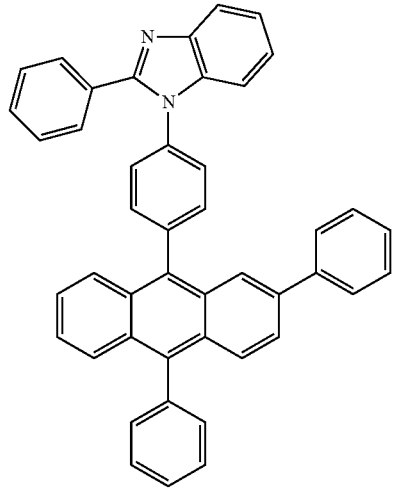
ET17
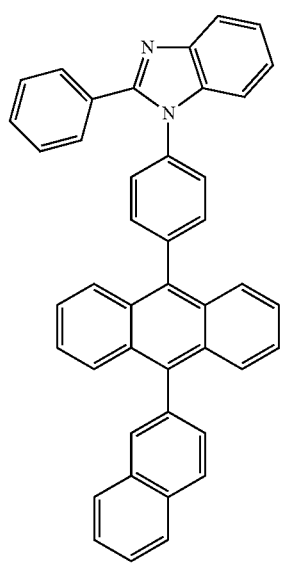
ET18
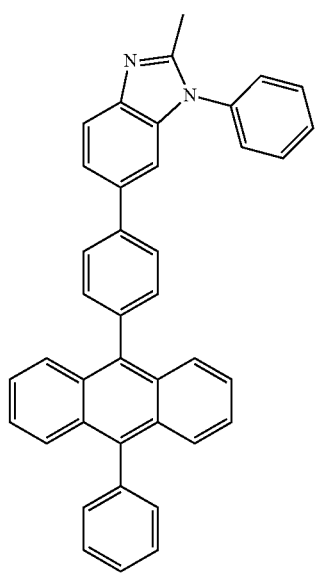

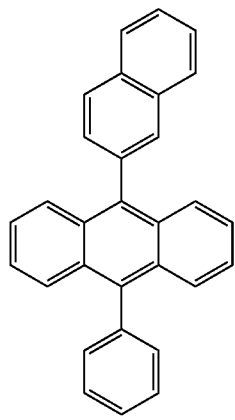
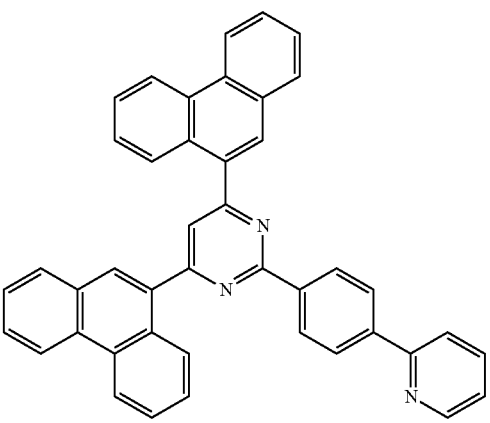
ET19
ET22
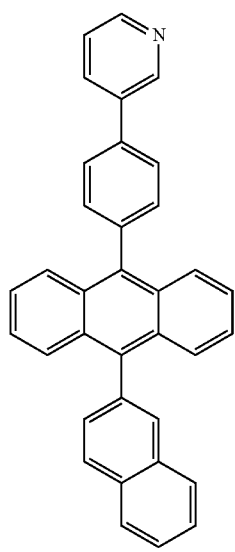
ET20
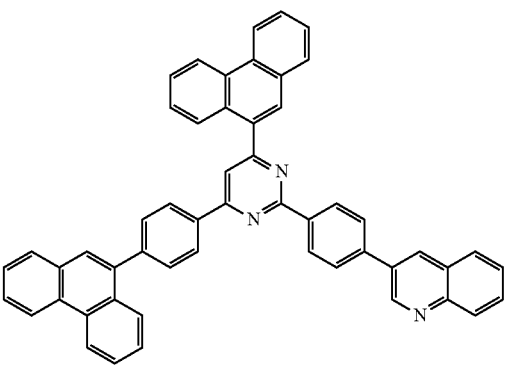
ET23
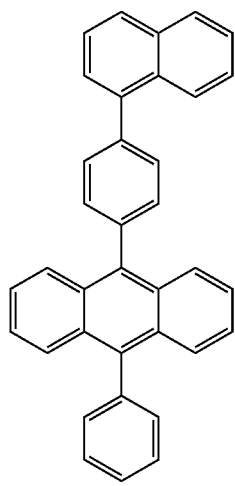
ET21
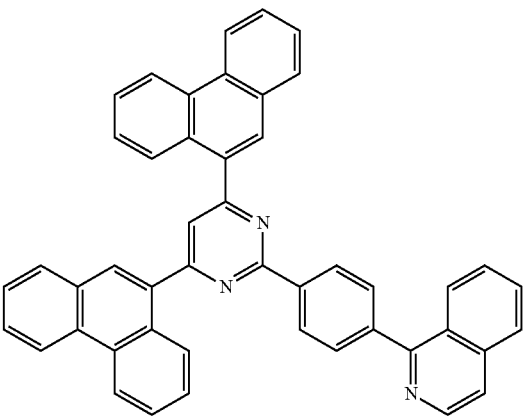
ET24

ET25
ET26
ET27
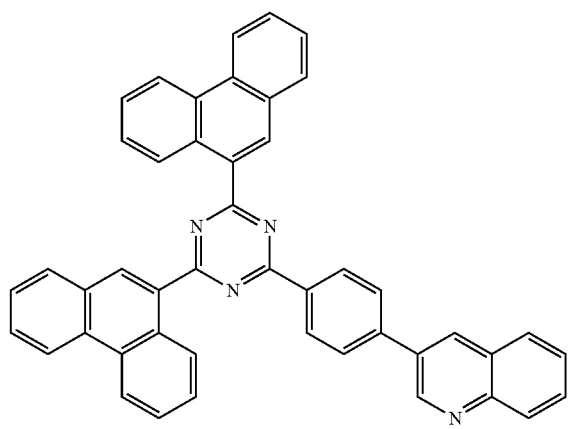
ET28
ET29
ET30
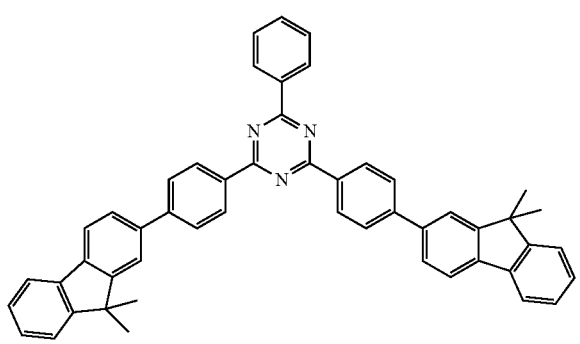
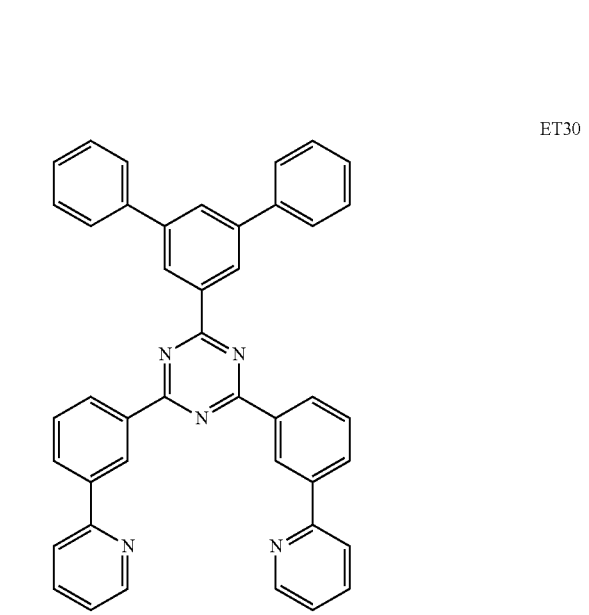

ET31 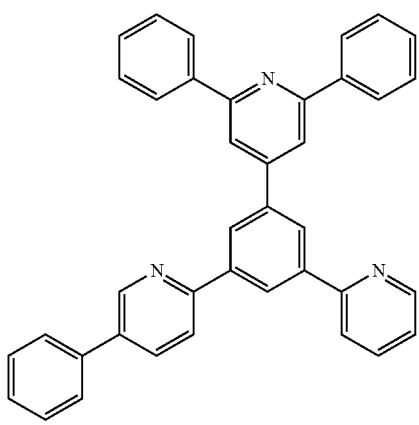
ET32 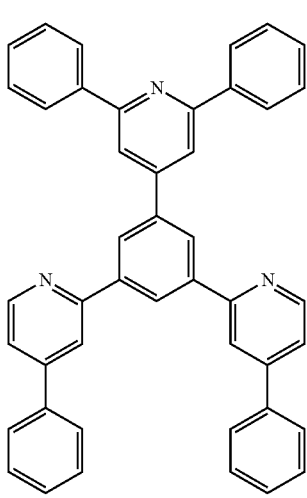
ET33 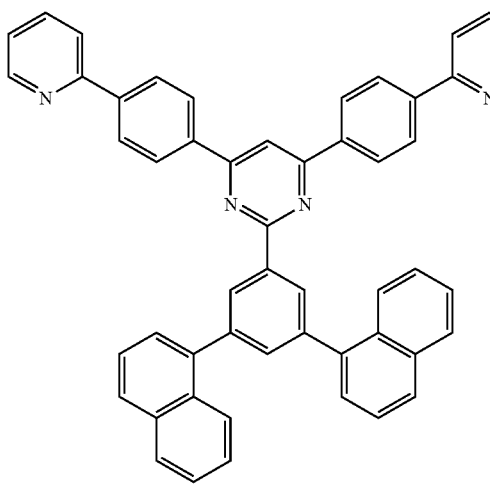
ET34 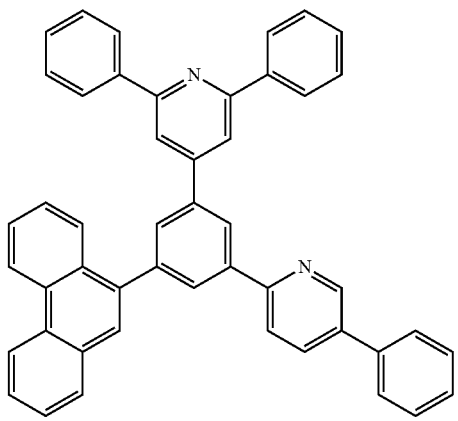
ET35 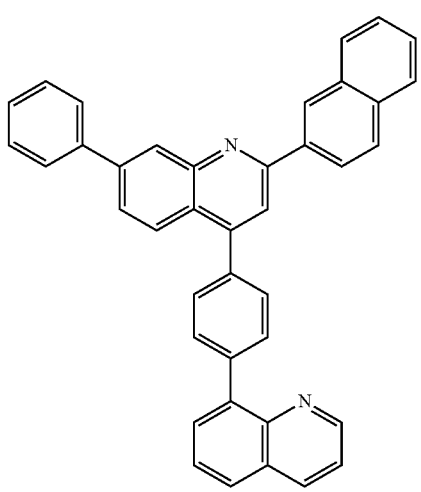
ET36 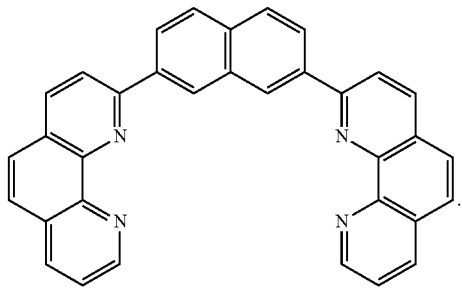
In various embodiments, the electron transport region may include at least one selected from 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ:

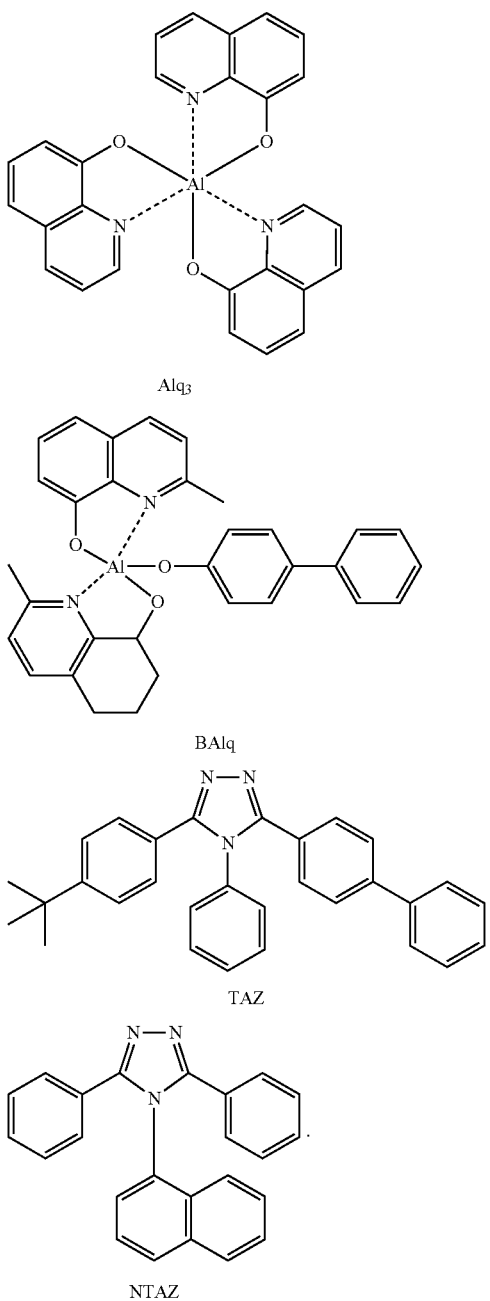

Alq₃

BAlq

TAZ

NTAZ

Respective thicknesses of a buffer layer, a hole blocking layer, or an electron control layer may be in a range of about 20 Å to about 1,000 Å, for example, about 30 Å to about 300 Å. When the thickness of the buffer layer, the hole blocking layer blocking layer, or the electron control layer is within these ranges, excellent hole blocking characteristics and/or electron adjustment characteristics may be obtained without a substantial increase in driving voltage.

A thickness of the electron transport layer may be in a range of about 100 Å to about 1,000 Å, for example, about 150 Å to about 500 Å. When the thickness of the electron transport layer is within these ranges, suitable or satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth metal complex. The alkali metal complex may include a metal ion selected from a Li ion, a sodium (Na) ion, a potassium (K) ion, a rubidium (Rb), and a cesium (Cs) ion, and the alkaline earth metal complex may include a metal ion selected from a Be ion, a Mg ion, a Ca ion, a strontium (Sr) ion, and a barium (Ba) ion. Each ligand coordinated with the metal ion of the alkali metal complex and the alkaline earth metal complex may independently be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxyphenyl oxadiazole, a hydroxyphenyl thiadiazol, a hydroxyphenyl pyridine, a hydroxyphenyl benzimidazole, a hydroxyphenyl benzothiazole, a bipyridine, a phenanthroline, and a cyclopentadiene, but embodiments of the metal-containing material are not limited thereto.

For example, the metal-containing material may include a Li complex. The Li complex may include, for example, Compound ET-D1 (lithium quinolate (LiQ)) or Compound ET-D2.

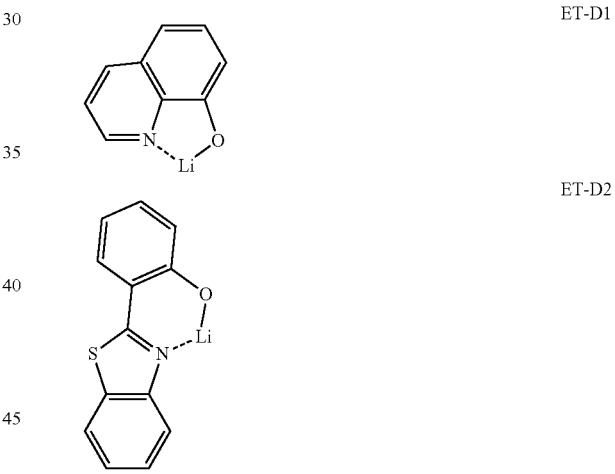

ET-D1

ET-D2

The electron transport region may include the electron injection layer that facilitates injection of electrons from the second electrode 190. The electron injection layer may directly contact (e.g., physically contact) the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combinations thereof.

The alkali metal may be selected from Li, Na, K, Rb, and Cs. In an embodiment, the alkali metal may be Li, Na, or Cs.

In various embodiments, the alkali metal may be Li or Cs, but embodiments of the alkali metal are not limited thereto.

The alkaline earth metal may be selected from Mg, Ca, Sr, and Ba.

The rare earth metal may be selected from scandium (Sc), yttrium (Y), cerium (Ce), terbium (Tb), ytterbium (Yb), and gadolinium (Gd).

The alkali metal compound, the alkaline earth metal compound, and the rare earth metal compound may be respectively selected from oxides and halides (for example, fluorides, chlorides, bromides, and iodines) of the alkali metal, the alkaline earth metal, and the rare earth metal.

The alkali metal compound may be selected from alkali metal oxides, such as $Li_2O$, $Cs_2O$, and $K_2O$, and alkali metal halides, such as LiF, NaF, CsF, KF, LiI, NaI, CsI, KI, and RbI. In an embodiment, the alkali metal compound may be selected from LiF, LizO, NaF, LiI, NaI, CsI, and KI, but embodiments of the alkali metal compound are not limited thereto.

The alkaline earth metal compound may be selected from alkaline earth metal compounds, such as BaO, SrO, CaO, $Ba_xSr_{1-x}O$ (0<x<1), and $Ba_xCa_{1-x}O$ (0<x<1). In an embodiment, the alkaline earth metal compound may be selected from BaO, SrO, and CaO, but embodiments of the alkaline earth metal compound are not limited thereto.

The rare earth metal compound may be selected from $YbF_3$, $ScF_3$, $ScO_3$, $Y_2O_3$, $Ce_2O_3$, $GdF_3$, and $TbF_3$. In an embodiment, the rare earth metal compound may be selected from $YbF_3$, $ScF_3$, $TbF_3$, $YbI_3$, $ScI_3$, and $TbI_3$, but embodiments of the rare earth metal compound are not limited thereto.

The alkali metal complex, the alkaline earth metal complex, and the rare earth metal complex may each include an alkali metal ion, an alkaline earth metal ion, and a rare earth metal ion as described above, and each ligand coordinated with a metal ion of the alkali metal complex, the alkaline earth metal complex, and the rare earth metal complex may be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxyphenyl thiadiazol, a hydroxyphenyl pyridine, a hydroxyphenyl benzimidazole, a hydroxyphenyl benzothiazole, a bipyridine, a phenanthroline, and a cyclopentadiene, but embodiments of the alkali metal complex, the alkaline earth metal complex, and the rare earth metal complex are not limited thereto.

The electron injection layer may include only (e.g., may consist of) the alkali metal, the alkaline earth metal, the rare earth metal, the alkali metal compound, the alkaline earth metal compound, the rare earth metal compound, the alkali metal complex, the alkaline earth metal complex, the rare earth metal complex, or any combinations thereof as described above. In various embodiments, the electron injection layer may further include, in addition to the alkali metal, the alkaline earth metal, the rare earth metal, the alkali metal compound, the alkaline earth metal compound, the rare earth metal compound, the alkali metal complex, the alkaline earth metal complex, the rare earth metal complex, or any combinations thereof, an organic material. When the electron injection layer further includes the organic material, the alkali metal, the alkaline earth metal, the rare earth metal, the alkali metal compound, the alkaline earth metal compound, the rare earth metal compound, the alkali metal complex, the alkaline earth metal complex, the earth metal based metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the ranges above, suitable or satisfactory electron injecting characteristics may be obtained without a substantial increase in driving voltage.

Second Electrode 190

The second electrode 190 may be disposed on the organic layer 150 having such a structure as described above. The second electrode 190 may be a cathode, which is an electron injection electrode, and in this regard, a material for the second electrode 190 may be selected from a metal, an alloy, an electrically conductive compound, and a combination thereof, which have a relatively low work function.

The second electrode 190 may include at least one selected from Li, Ag, Mg, Al, Al—Li, Ca, Mg—In, Mg—Ag, ITO, and IZO, but embodiments of the second electrode are not limited thereto. The second electrode 190 may be a reflective electrode, a semi-transmissive electrode, or a transmissive electrode.

The second electrode 190 may have a single-layered structure, or a multi-layered structure including a plurality of layers.

Figure 2:
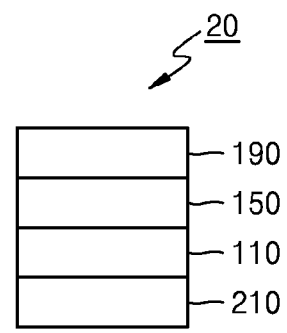
FIG. 2 is a schematic diagram illustrating an organic light-emitting device according to another embodiment.
Figure 3:
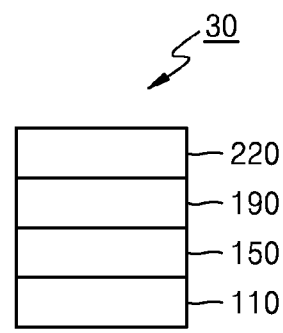
FIG. 3 is a schematic diagram illustrating an organic light-emitting device according to another embodiment.
Figure 4:
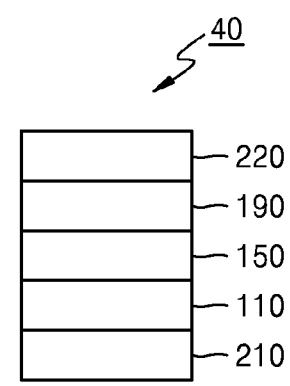
FIG. 4 is a schematic diagram illustrating an organic light-emitting device according to another embodiment.

Descriptions of FIGS. 2 to 4

An organic light-emitting device 20 of FIG. 2 includes a first capping layer 210, a first electrode 110, an organic layer 150, and a second electrode 190, which are sequentially stacked in the stated order. An organic light-emitting device 30 of FIG. 3 includes a first electrode 110, an organic layer 150, a second electrode 190, and a second capping layer 220, which are sequentially stacked in the stated order. An organic light-emitting device 40 of FIG. 4 includes a first capping layer 210, a first electrode 110, an organic layer 150, a second electrode 190, and a second capping layer 220, which are sequentially stacked in the stated order.

In FIGS. 2-4, the first electrode 110, the organic layer 150, and the second electrode 190 may each independently be the same as described herein in connection with those provided in the present disclosure (e.g., may be the same as the corresponding features described in connection with FIG. 1).

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may include at least one material selected from a carbocyclic compound, a heterocyclic compound, an amine-based compound, a porphine derivative, a phthalocyanine derivative, a naphthalocyanine derivative, an alkali metal complex, and an alkaline earth metal complex. The carbocyclic compound, the heterocyclic compound, and the amine-based compound may be optionally substituted with a substituent containing at least one element selected from O, N, S, Se, Si, F, Cl, Br, and I. In various embodiments, at least one selected from the first capping layer 210 and the second capping layer 220 may include the amine-based compound.

In various embodiments, at least one selected from the first capping layer 210 and the second capping layer 220 may include the compound represented by Formula 201 or the compound represented by Formula 202.

In various embodiments, at least one selected from the first capping layer 210 and the second capping layer 220 may include a compound selected from Compounds HT28 to HT33 and Compounds CP1 to CP5, but embodiments of the first capping layer 210 and the second capping layer 220 are not limited thereto:

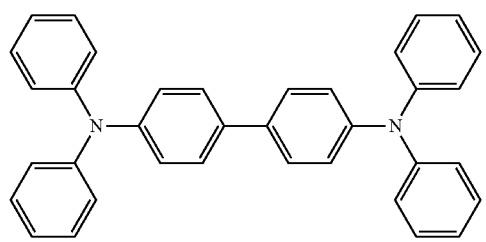

CP1

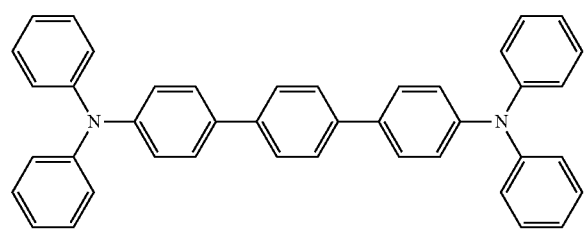

CP2

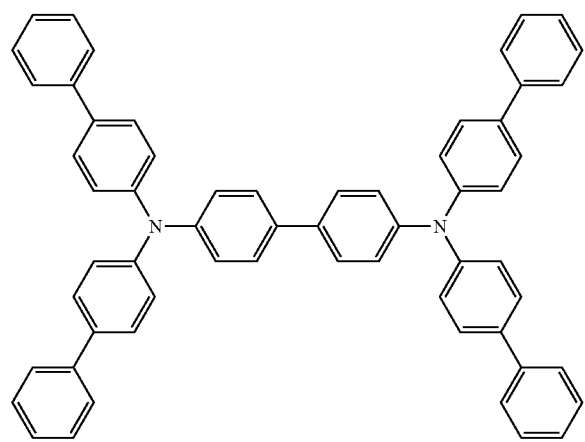

CP3

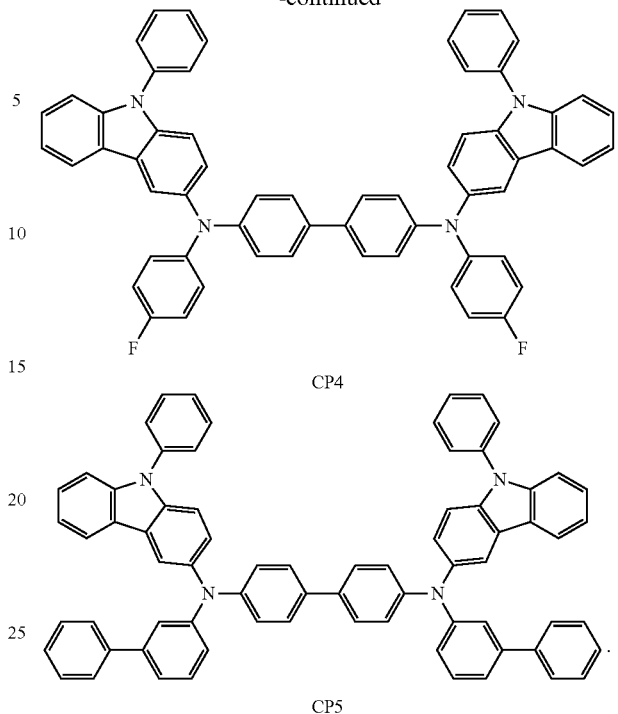

CP4

CP5

Figure 5:
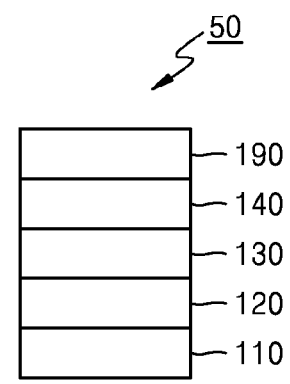
FIG. 5 is schematic diagram illustrating an organic light-emitting device according to another embodiment.

An organic light-emitting device 50 of FIG. 5 includes a first electrode 110, a hole transport region 120, an emission layer 130, an electron transport region 140, and a second electrode 190, which are sequentially stacked in the stated order. The first electrode 110, the hole transport region 120, the emission layer 130, the electron transport region 140, and the second electrode 190 may each independently be the same as described herein in connection with those provided in the present disclosure.

Hereinabove, the organic light-emitting device has been described with reference to FIGS. 1 to 5, but the organic light-emitting device is not limited thereto.

Layers constituting the hole transport region, the emission layer, and layers constituting the electron transport region may be formed in a certain region by using one or more suitable methods selected from vacuum deposition, spin coating, casting Langmuir-Blodgett deposition, ink-jet printing, laser-printing, and laser induced thermal imaging (LITI).

When layers constituting the hole transport region, the emission layer, and layers constituting the electron transport region are each formed by vacuum deposition, for example, the vacuum deposition may be performed at a deposition temperature of about 100 to about 500° C., at vacuum degree of about $10^{-8}$ to about $10^{-3}$ torr, and at a deposition rate of about 0.01 to about 100 Å/sec, by taking into account a material utilized to form the layer and the structure of the layer to be formed.

When layers constituting the hole transport region, the emission layer, and layers constituting the electron transport region are each formed by spin coating, for example, the spin coating may be performed at a coating rate of about 2,000 rpm to about 5,000 rpm and at a temperature of about 80° C. to about 200° C., by taking into account a material utilized to form the layer and the structure of the layer to be formed.

General Definition of Substituents

Hereinafter, the representative substituents selected from the substituents used in the present disclosure can be defined as follows (the number of carbon atoms limiting the substituent is non-limited and does not limit the characteristics of the substituents, and substituents not defined in the present disclosure can be defined in accordance with the general definition thereof).

As used herein, the term "$C_1$-$C_{60}$ alkyl group" refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. As used herein, the term "$C_1$-$C_{60}$ alkylene group" refers to a divalent group having substantially the same structure as the $C_1$-$C_{60}$ alkyl group, except that the $C_1$-$C_{60}$ alkylene group is divalent instead of monovalent.

As used herein, the term "$C_2$-$C_{60}$ alkenyl group" refers to a hydrocarbon group having at least one carbon-carbon double bond in a main chain (e.g., in the middle) or at either terminal end of the $C_2$-$C_{60}$ alkyl group, and examples thereof include an ethenyl group, a propenyl group, and a butenyl group. As used herein, the term "$C_2$-$C_{60}$ alkenylene group" refers to a divalent group having substantially the same structure as the $C_2$-$C_{60}$ alkenyl group, except that the $C_2$-$C_{60}$ alkenylene group is divalent instead of monovalent.

As used herein, the term "$C_2$-$C_{60}$ alkynyl group" refers to a hydrocarbon group having at least one carbon-carbon triple bond in a main chain (e.g., in the middle) or at either terminal end of the $C_2$-$C_{60}$ alkyl group, and examples thereof include an ethynyl group and a propynyl group. As used herein, the term "$C_2$-$C_{60}$ alkynylene group" refers to a divalent group having substantially the same structure as the $C_2$-$C_{60}$ alkynyl group, except that the $C_2$-$C_{60}$ alkynylene group is divalent instead of monovalent.

As used herein, the term "$C_1$-$C_{60}$ alkoxy group" refers to a monovalent group represented by -$OA_{101}$ (where $A_{101}$ is the $C_1$-$C_{60}$ alkyl group), and examples thereof include a methoxy group, an ethoxy group, and an isopropyloxy group.

As used herein, the term "$C_3$-$C_{10}$ cycloalkyl group" refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. As used herein, the term "$C_3$-$C_{10}$ cycloalkylene group" may refer to a divalent group having substantially the same structure as the $C_3$-$C_{10}$ cycloalkyl group, except that the $C_3$-$C_{10}$ cycloalkylene group is divalent instead of monovalent.

As used herein, the term "$C_1$-$C_{10}$ heterocycloalkyl group" refers to a monovalent saturated monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. As used herein, the term "$C_1$-$C_{10}$ heterocycloalkylene group" refers to a divalent group having substantially the same structure as the $C_1$-$C_{10}$ heterocycloalkyl group, except that the $C_1$-$C_{10}$ heterocycloalkylene group is divalent instead of monovalent.

As used herein, the term "$C_3$-$C_{10}$ cycloalkenyl group" refers to a monovalent monocyclic group that has 3 to 10 carbon atoms and at least one carbon-carbon double bond in the ring thereof and does not have aromaticity (e.g., the ring is non-aromatic, or the entire group is non-aromatic), and examples thereof include a cyclopentenyl group, a cyclohexenyl group, and a cycloheptenyl group. As used herein, the term "$C_3$-$C_{10}$ cycloalkenylene group" refers to a divalent group having substantially the same structure as the $C_3$-$C_{10}$ cycloalkenyl group, except that the $C_3$-$C_{10}$ cycloalkenylene group is divalent instead of monovalent.

As used herein, the term "$C_1$-$C_{10}$ heterocycloalkenyl group" refers to a monovalent monocyclic group that has at least one heteroatom selected from N, O, Si, P, and S as a ring-forming atom, 1 to 10 carbon atoms, and at least one carbon-carbon double bond in the ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. As used herein, the term "$C_1$-$C_{10}$ heterocycloalkenylene group" refers to a divalent group having substantially the same structure as the $C_1$-$C_{10}$ heterocycloalkenyl group, except that the $C_1$-$C_{10}$ heterocycloalkenylene group is divalent instead of monovalent.

As used herein, the term "$C_6$-$C_{60}$ aryl group" refers to a monovalent group having an aromatic system having 6 to 60 carbon atoms, and, as used herein, the term "$C_6$-$C_{60}$ arylene group" refers to a divalent group having an aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other (e.g., condensed with each other).

As used herein, the term "$C_1$-$C_{60}$ heteroaryl group" refers to a monovalent group having a heterocyclic aromatic system that has at least one heteroatom selected from N, O, Si, P, and S as a ring-forming atom, and 1 to 60 carbon atoms. As used herein, the term "$C_1$-$C_{60}$ heteroarylene group" refers to a divalent group having a heterocyclic aromatic system that has at least one heteroatom selected from N, O, Si, P, and S as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group include two or more rings, the respective rings may be fused to each other (e.g., condensed with each other).

As used herein, the term "$C_6$-$C_{60}$ aryloxy group" refers to a group represented by -$OA_{102}$ (where $A_{102}$ is the $C_6$-$C_{60}$ aryl group), and, as used herein, the term "$C_6$-$C_{60}$ arylthio group" refers to a group represented by -$SA_{103}$ (where $A_{103}$ is the $C_6$-$C_{60}$ aryl group).

As used herein, the term "monovalent non-aromatic condensed polycyclic group" refers to a monovalent group that has two or more rings condensed to each other (e.g., fused together), has only carbon atoms as ring-forming atoms (for example, 8 to 60 carbon atoms), and has non-aromaticity in the entire molecular structure (e.g., the entire molecular structure of the group is non-aromatic). An example of the monovalent non-aromatic condensed polycyclic group includes a fluorenyl group. As used herein, the term "divalent non-aromatic condensed polycyclic group" refers to a divalent group having substantially the same structure as the monovalent non-aromatic condensed polycyclic group, except that the divalent non-aromatic condensed polycyclic group is divalent instead of monovalent.

As used herein, the term "monovalent non-aromatic condensed heteropolycyclic group" refers to a monovalent group that has two or more rings condensed to each other (e.g., fused together), has at least one heteroatom selected from N, O, Si, P, and S as a ring-forming atom, in addition to carbon atoms (for example, 1 to 60 carbon atoms), and has non-aromaticity in the entire molecular structure (e.g., the entire molecular structure of the group is non-aromatic). An example of the monovalent non-aromatic condensed heteropolycyclic group includes a carbazolyl group. A divalent non-aromatic condensed heteropolycyclic group used herein refers to a divalent group having substantially the same structure as the monovalent non-aromatic condensed heteropolycyclic group, except that the divalent non-aromatic condensed heteropolycyclic group is divalent instead of monovalent.

As used herein, the term "$C_5$-$C_{60}$ carbocyclic group" refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as a benzene group, a monovalent group, such as a phenyl group, or a divalent group, such as a phenylene group. In various embodiments, depending on the number of substituents connected to the $C_5$-$C_{60}$ carbocyclic group, the $C_5$-$C_{60}$ carbocyclic group may be a trivalent group or a quadrivalent group (e.g., a tetravalent group).

As used herein, the term "$C_1$-$C_{60}$ heterocyclic group" refers to a group having substantially the same structure as the $C_5$-$C_{60}$ carbocyclic group, except that as a ring-forming atom, at least one heteroatom selected from N, O, Si, P, and S is used in addition to carbon (for example, 1 to 60 carbon atoms).

In the present disclosure, at least one substituent selected from the $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$) ($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$) ($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group (e.g., a hydrazino group), a hydrazono group (e.g., a hydrazono group), a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" used herein refers to a phenyl group, the term "Me" used herein refers to a methyl group, the term "Et" used herein refers to an ethyl group, the term "ter-Bu" or "But" used herein refers to a tert-butyl group, and the term "OMe" used herein refers to a methoxy group.

The term "biphenyl group" used herein refers to "a phenyl group substituted with a phenyl group". The "biphenyl group" may be considered an example of "a substituted phenyl group" having "a $C_6$-$C_{60}$ aryl group" as a substituent.

The term "terphenyl group" used herein refers to "a phenyl group substituted with a biphenyl group". The "terphenyl group" may be considered an example of "a substituted phenyl group" having "a $C_6$-$C_{60}$ aryl group substituted with a $C_6$-$C_{60}$ aryl group" as a substituent.

* and *' used herein, unless defined otherwise, each indicate a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples means that an identical (or substantially identical) number of molar equivalents of A was used in place of molar equivalents of B.

SYNTHESIS EXAMPLES ratio of 5:3:2 (v/v) based on a reagent (0.1 M, 1 eq)) were added to a flask containing starting materials (Compound S (1 eq) and Compound S-1 (1.2 eq)) to form a mixed solution, and then, the mixed solution was stirred under reflux for 12 hours. After the reaction solution was cooled to room temperature, an extraction process was performed thereon

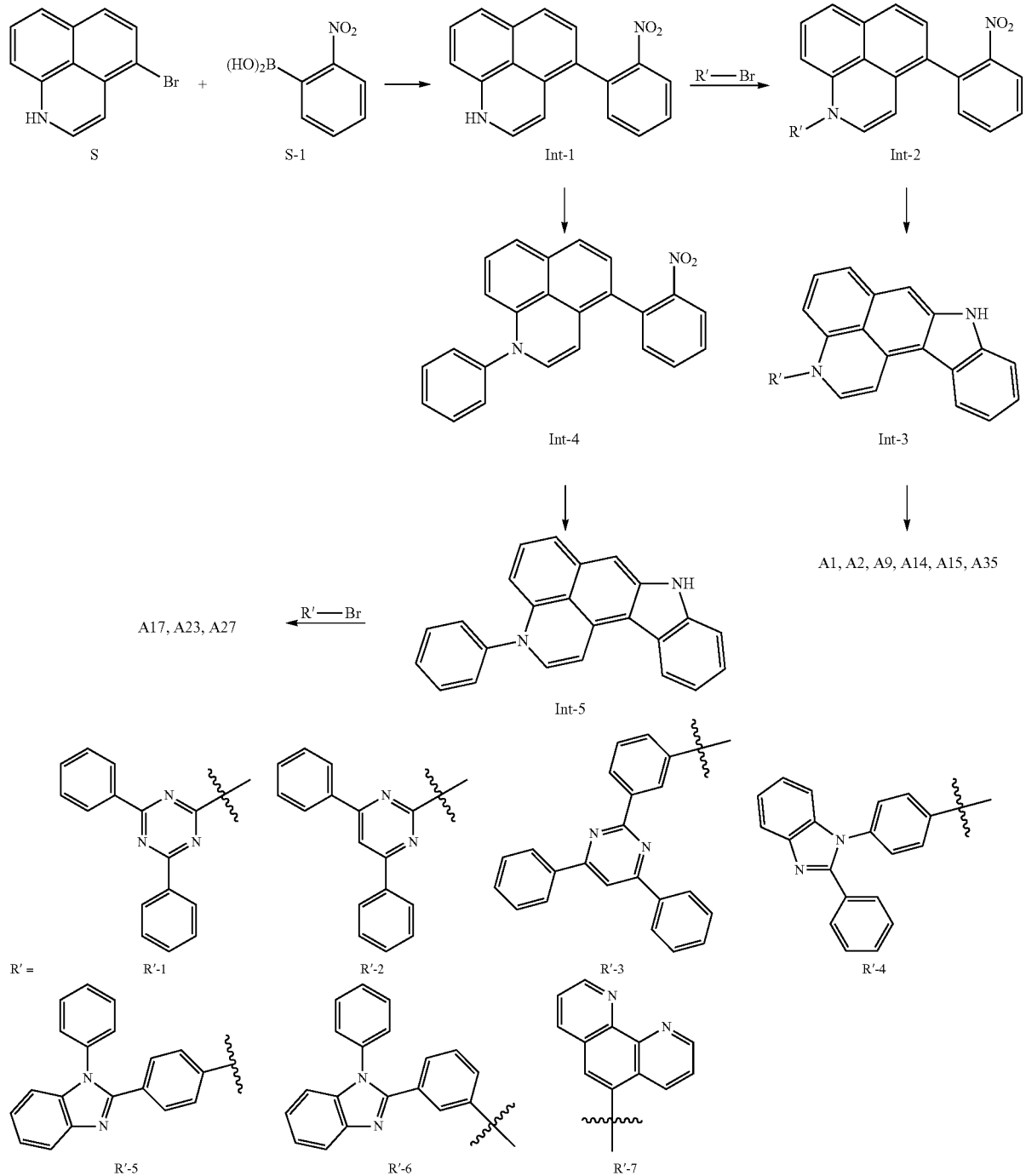

Synthesis of Intermediate 1 (Int-1)

Pd(PPh$_3$)$_4$ (0.02 eq), Na$_2$CO$_3$ (1.2 eq), and a mixture of toluene, distilled water, and ethanol (at a mixing volume using methyl chloride (MC), followed by a washing process performed thereon using distilled water. Then, the resulting product obtained from the washing process was subjected to a drying process using magnesium sulfate ($MgSO_4$) and a distillation process under reduced pressure. The residues obtained therefrom were separated by column chromatography, thereby completing the preparation of Int-1 (yield: 87%).

High Resolution Mass Spectrometry (HRMS) for $C_{18}H_{12}N_2O_2$ [M]+: calculated: 288.31, found: 287.

Synthesis of Int-2

$Pd(dba)_3$ (0.03 eq), $(t-Bu)_3P$ (0.06 eq), and toluene (based on a reagent (0.1M, 1 eq)) were added to a flask containing starting materials (Int-1 (1 eq) and R'—X—Br (1.2 eq)) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Int-2.

Synthesis of Int-3

Int-2 (1 eq) was mixed with triethylphosphite (10 eq) to form a mixed solution, and then, the mixed solution was stirred under reflux in a nitrogen atmosphere for 12 hours. Following substantial completion of the reaction, a vacuum distillation process was performed on the reaction solution to remove unreacted triethylphosphite. The resulting product was purified by column chromatography (Hexane:MC=4:1 (v/v)), thereby completing the preparation of the desired compound, Int-3.

Synthesis of Int-4

$Pd(dba)_3$ (0.03 eq), $(t-Bu)_3P$ (0.06 eq), and toluene (based on a reagent (0.1 M, 1 eq)) were added to a flask containing starting materials (Int-1 (1 eq) and bromobenzene (1.2 eq)) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Int-4 (yield: 81%).

HRMS for $C_{24}H_{16}N_2O_2$ [M]+: calculated: 364.40, found: 363.

Synthesis of Int-5

Int-4 (1 eq) was mixed with triethylphosphite (10 eq) to form a mixed solution, and then, the mixed solution was stirred under reflux in a nitrogen atmosphere for 12 hours. Following the completion of the reaction, a vacuum distillation process was performed on the reaction solution to remove unreacted triethylphosphite. The resulting product was purified by column chromatography (Hexane:MC=4:1 (v/v)), thereby completing the preparation of the desired compound, Int-5.

HRMS for $C_{24}H_{16}N_2$ [M]+: calculated: 332.41, found: 331.

Synthesis Example 1: Synthesis of Compound A1

$Pd(dba)_3$ (0.03 eq), $(t-Bu)_3P$ (0.06 eq), and toluene (based on a reagent (0.1 M, 1 eq)) were added to a flask containing Int-3 (1 eq) (R'=R'-1) and bromobenzene (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A1 (yield: 84.6%).

HRMS for $C_{39}H_{25}N_5$[M]+: calculated: 563.66, found: 562.

Elemental Analysis for $C_{39}H_{25}N_5$ calculated: C, 83.10; H, 4.47; N, 12.42

Synthesis Example 2: Synthesis of Compound A2

Compound A2 (R'=R'-2) (yield: 81.7%) was obtained in the same manner as described in connection with the synthesis of Compound A1 of Synthesis Example 1, except that, in Int-3, R' was R'-2 instead of R'-1.

HRMS for $C_{40}H_{26}N_4$[M]+: calculated: 562.68, found: 561.

Elemental Analysis for $C_{40}H_{26}N_4$ calculated: C, 85.38; H, 4.66; N, 9.96

Synthesis Example 3: Synthesis of Compound A9

Compound A9 (R'=R'-3) (yield: 82.7%) was obtained in the same manner as described in connection with the synthesis of Compound A1 of Synthesis Example 1, except that, in Int-3, R' was R'-3 instead of R'-1.

HRMS for $C_{46}H_{30}N_4$ [M]+: calculated: 638.77, found: 637.

Elemental Analysis for $C_{46}H_{30}N_4$ calculated: C, 86.49; H, 4.73; N, 8.77

Synthesis Example 4: Synthesis of Compound A14

Compound A14 (R'=R'-4) (yield: 80.9%) was obtained in the same manner as described in connection with the synthesis of Compound A1 of Synthesis Example 1, except that, in Int-3, R' was R'-4 instead of R'-1.

HRMS for $C_{46}H_{30}N_4$ [M]+: calculated: 638.77, found: 637.

Elemental Analysis for $C_{46}H_{30}N_4$ calculated: C, 86.49; H, 4.73; N, 8.77

Synthesis Example 5: Synthesis of Compound A15

Compound A15 (R'=R'-5) (yield: 80.4%) was obtained in the same manner as described in connection with the synthesis of Compound A1 of Synthesis Example 1, except that, in Int-3, R' was R'-5 instead of R'-1.

HRMS for $C_{43}H_{28}N_4$ [M]+: calculated: 600.73, found: 599.

Elemental Analysis for $C_{43}H_{28}N_4$ calculated: C, 85.97; H, 4.70; N, 9.33

Synthesis Example 6: Synthesis of Compound A17

$Pd(dba)_3$ (0.03 eq), $(t-Bu)_3P$ (0.06 eq), and toluene (based on a reagent (0.1 M, 1 eq)) were added to a flask containing Int-5 (1 eq) and R'-1 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using MgSO$_4$ and a vacuum distillation process. The residue obtained therefrom was purified by column chromatography, thereby completing the preparation of Compound A17 (yield: 71.4%).

HRMS for C$_{39}$H$_{25}$N$_5$[M]+: calculated: 563.66, found: 562.

Elemental Analysis for C$_{39}$H$_{25}$N$_5$ calculated: C, 83.10; H, 4.47; N, 12.42

Synthesis Example 7: Synthesis of Compound A23

Compound A23 (yield: 72.9%) was obtained in the same manner as described in connection with the synthesis of Compound A17 of Synthesis Example 6, except that, in R'—Br, R' was R'-2 instead of R'-1.

HRMS for C$_{46}$H$_{30}$N$_4$ [M]+: calculated: 638.77, found: 637.

Elemental Analysis for C$_{46}$H$_{30}$N$_4$ calculated: C, 86.49; H, 4.73; N, 8.77

Synthesis Example 8: Compound A27

Compound A27 was obtained in the same manner as described in connection with the synthesis of Compound A17 of Synthesis Example 6, except that, in R'—Br, R' was R'-6 instead of R'-1.

HRMS for C$_{43}$H$_{28}$N$_4$[M]+: calculated: 600.73, found: 599.

Elemental Analysis for C$_{43}$H$_{28}$N$_4$ calculated: C, 85.97; H, 4.70; N, 9.33

Synthesis Example 9: Synthesis of Compound A35

Compound A35 (yield: 68.7%) was obtained in the same manner as described in connection with the synthesis of Compound A17 of Synthesis Example 6, except that, in R'—Br, R' was R'-7 instead of R'-1.

HRMS for C$_{40}$H$_{24}$N$_6$ [M]+: calculated: 588.67, found: 587.

Elemental Analysis for C$_{40}$H$_{24}$N$_6$ calculated: C, 81.61; H, 4.11; N, 14.28

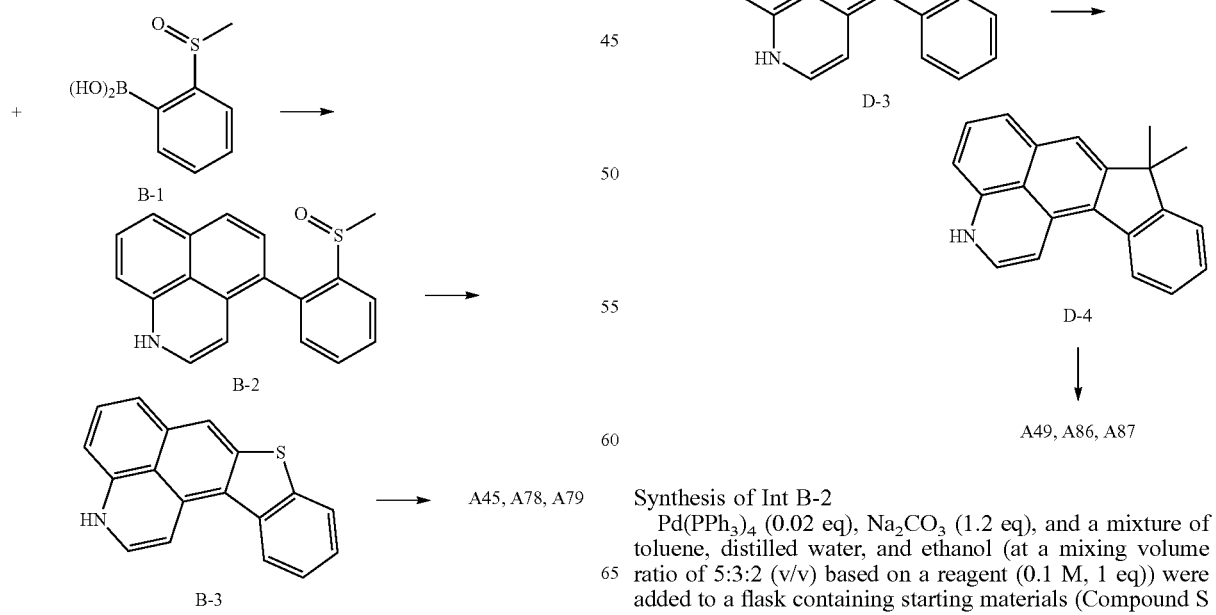

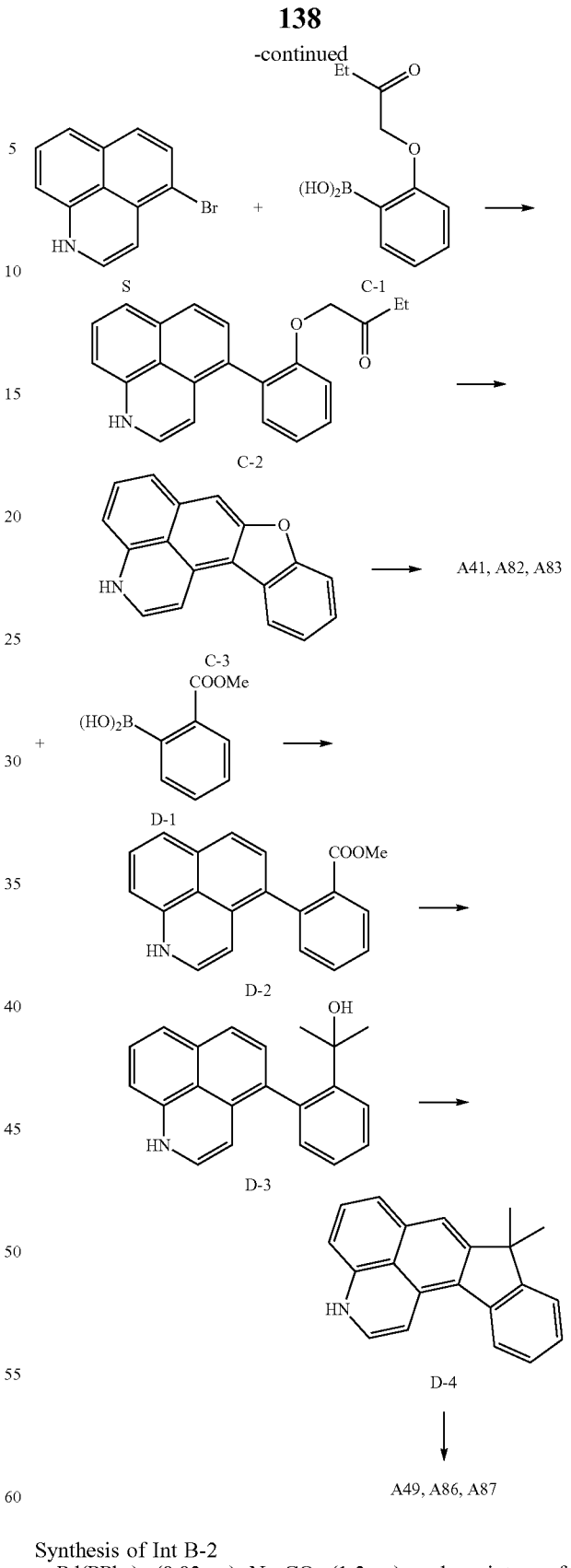

Synthesis of Int B-2

Pd(PPh$_3$)$_4$ (0.02 eq), Na$_2$CO$_3$ (1.2 eq), and a mixture of toluene, distilled water, and ethanol (at a mixing volume ratio of 5:3:2 (v/v) based on a reagent (0.1 M, 1 eq)) were added to a flask containing starting materials (Compound S (1 eq) and Compound B-1 (1.2 eq)) to form a mixed solution, and then, the mixed solution was stirred under reflux for 12 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a distillation process under reduced pressure. The residues obtained therefrom were separated by column chromatography, thereby completing the preparation of Int B-2 (yield: 78%).

HRMS for $C_{19}H_{19}NOS$ [M]+: calculated: 305.40, found: 304.

Synthesis of Int B-3

Int B-2 and trifluoromethanesulfonic acid ($CF_3SO_3H$) were added to a flask to form a mixed solution, and then, the mixed solution was stirred at room temperature for 24 hours. Next, a mixture of water and pyridine (at a mixing ratio of 8:1) was added thereto, and the resulting mixed solution was stirred under reflux for 30 minutes. After the reaction solution was cooled to room temperature, an extraction process was performed thereon using MC. Then, the resulting product obtained from the washing process was subjected to a drying process using $MgSO_4$ and a vacuum distillation process. The residue obtained therefrom was purified by column chromatography, thereby completing the preparation of Int B-3 (yield: 67%).

HRMS for $C_{16}H_{11}NS$ [M]+: calculated: 273.35, found: 272.

Synthesis of Int C-2

$Pd(PPh_3)_4$ (0.02 eq), $Na_2CO_3$ (1.2 eq), and a mixture of toluene, distilled water, and ethanol (at a mixing volume ratio of 5:3:2 (v/v) based on a reagent (0.1 M, 1 eq)) were added to a flask containing starting materials (Compound S (1 eq) and Compound C-1 (1.2 eq)) to formed a mixed solution, and then, the mixed solution was stirred under reflux for 12 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a distillation process under reduced pressure. The residues obtained therefrom were separated by column chromatography, thereby completing the preparation of Int C-2 (yield: 55.4%).

HRMS for $C_{22}H_{19}NO_2$ [M]+: calculated: 329.40, found: 328.

Synthesis of Int C-3

Int C-2 and $CF_3SO_3H$ were added to a flask to form a mixed solution, and then, the mixed solution was stirred at room temperature for 24 hours. Next, a mixture of water and pyridine (at a mixing ratio of 8:1) was added thereto, and the resulting mixed solution was stirred under reflux for 30 minutes. After the reaction solution was cooled to room temperature, an extraction process was performed thereon using MC. Then, the resulting product obtained from the washing process was subjected to a drying process using $MgSO_4$ and a vacuum distillation process. The residue obtained therefrom was purified by column chromatography, thereby completing the preparation of Int C-3 (yield: 41%).

HRMS for $C_{18}H_{11}NS$ [M]+: calculated: 273.35, found: 272.

Synthesis of Int D-2

$Pd(PPh_3)_4$ (0.02 eq), $Na_2CO_3$ (1.2 eq), and a mixture of toluene, distilled water, and ethanol (at a mixing volume ratio of 5:3:2 (v/v) based on a reagent (0.1 M, 1 eq)) were added to a flask containing starting materials (Compound S (1 eq) and Compound D-1 (1.2 eq)) to form a mixed solution, and then, the mixed solution was stirred under reflux for 12 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a distillation process under reduced pressure. The residues obtained therefrom were separated by column chromatography, thereby completing the preparation of Int D-2 (yield: 76.2%).

HRMS for $C_{20}H_{15}NO_2$ [M]+: calculated: 301.35, found: 300.

Synthesis of Int D-3

Int D-2 (1 eq) was dissolved in 100 ml of ether to form a mixed solution, and then, the mixed solution was cooled at a temperature of −78° C. The resulting solution was added to methyllithium (1.2 eq), followed by being stirred for 1 hour. The temperature of the reaction solution was gradually increased to room temperature, and then, the reaction solution was further stirred for 4 hours. After the completion of the reaction, an extraction process was performed thereon using 200 ml of water, and a distillation process was performed on the organic layer under reduced pressure. The resulting product was subjected to re-crystallization using ethanol/acetone (at a volume ratio of 1:1), thereby completing the preparation of Int D-3 (yield: 67%).

HRMS for $C_{21}H_{19}NO$ [M]+: calculated: 301.39, found: 300.

Elemental Analysis for $C_{21}H_{19}NO$ calculated: C, 83.69; H, 6.35; N, 4.65; O, 5.31

Synthesis of Int D-4

Int D-3 was dissolved in 150 ml of a strong (high concentration) $H_3PO_4$ solution to form a mixed solution, and then, the mixed solution was stirred for 5 hours. An extraction process was performed thereon using 200 ml of water and 200 ml of ethyl acetate, and a distillation process was performed on the organic layer under reduced pressure. The resulting product was subjected to re-crystallization using 150 ml of ethanol, thereby completing the preparation of Int D-4 (yield: 72%).

HRMS for $C_{21}H_{17}N$ [M]+: calculated: 283.37, found: 282.

Synthesis Example 10: Synthesis of Compound A41

$Pd(dba)_3$ (0.03 eq), $(t-Bu)_3P$ (0.06 eq), and toluene (based on a reagent (0.1 M 1 eq)) were added to a flask containing Int C-2 (1 eq) and R'-1 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A41 (yield: 71.4%).

HRMS for $C_{33}H_{20}N_4O$ [M]+: calculated: 488.55, found: 487.

Elemental Analysis for $C_{33}H_{20}N_4O$ calculated: C, 81.13; H, 4.13; N, 11.47; O, 3.27

Synthesis Example 11: Synthesis of Compound A45

$Pd(dba)_3$ (0.03 eq), $(t-Bu)_3P$ (0.06 eq), and toluene (based on a reagent (0.1 M 1 eq)) were added to a flask containing Int B-2 (1 eq) and R'-1 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A45 (yield: 68.4%).

HRMS for $C_{33}H_{20}N_4S$ [M]+: calculated: 504.61, found: 503.

Elemental Analysis for $C_{33}H_{20}N_4S$ calculated: C, 78.55; H, 4.00; N, 11.10; S, 6.35

Synthesis Example 12: Synthesis of Compound A49

$Pd(dba)_3$ (0.03 eq), $(t-Bu)_3P$ (0.06 eq), and toluene (based on a reagent (0.1 M 1 eq)) were added to a flask containing Int D-4 (1 eq) and R'-1 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A49 (yield: 80.4%).

HRMS for $C_{36}H_{26}N_4$ [M]+: calculated: 514.63, found: 513.

Elemental Analysis for $C_{36}H_{26}N_4$ calculated: C, 84.02; H, 5.09; N, 10.89

Synthesis Example 13: Compound A78

$Pd(dba)_3$ (0.03 eq), $(t-Bu)_3P$ (0.06 eq), and toluene (based on a reagent (0.1 M 1 eq)) were added to a flask containing Int B-2 (1 eq) and R'-4 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A78 (yield: 71.9%).

HRMS for $C_{37}H_{23}N_3S$ [M]+: calculated: 541.67, found: 540.

Elemental Analysis for $C_{37}H_{23}N_3S$ calculated: C, 82.04; H, 4.28; N, 7.76; S, 5.92

Synthesis Example 14: Synthesis of Compound A79

$Pd(dba)_3$ (0.03 eq), $(t-Bu)_3P$ (0.06 eq), and toluene (based on a reagent (0.1 M 1 eq)) were added to a flask containing Int B-2 (1 eq) and R'-5 (1.2eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A79 (yield: 73%).

HRMS for $C_{37}H_{23}N_3S$ [M]+: calculated: 541.67, found: 540.

Elemental Analysis for $C_{37}H_{23}N_3S$ calculated: C, 82.04; H, 4.28; N, 7.76; S, 5.92

Synthesis Example 15: Synthesis of Compound A82

$Pd(dba)_3$ (0.03 eq), $(t-Bu)_3P$ (0.06 eq), and toluene (based on a reagent (0.1 M 1 eq)) were added to a flask containing Int C-2 (1 eq) and R'-4 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A82 (yield: 74.9%).

HRMS for $C_{37}H_{23}N_3O$ [M]+: calculated: 525.61, found: 524.

Elemental Analysis for $C_{37}H_{23}N_3O$ calculated: C, 84.55; H, 4.41; N, 7.99; O, 3.04

Synthesis Example 16: Synthesis of Compound A83

$Pd(dba)_3$ (0.03 eq), $(t-Bu)_3P$ (0.06 eq), and toluene (based on a reagent (0.1 M 1 eq)) were added to a flask containing Int C-2 (1 eq) and R'-5 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A83 (yield: 75.1%).

HRMS for $C_{37}H_{23}N_3O$ [M]+: calculated: 525.61, found: 524.

Elemental Analysis for $C_{37}H_{23}N_3O$ calculated: C, 84.55; H, 4.41; N, 7.99; O, 3.04

Synthesis Example 17: Synthesis of Compound A86

$Pd(dba)_3$ (0.03 eq), $(t-Bu)_3P$ (0.06 eq), and toluene (based on a reagent (0.1 M 1 eq)) were added to a flask containing Int D-4 (1 eq) and R'-4 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using $MgSO_4$ and a vacuum distillation process. The residue obtained therefrom was purified by column chromatography, thereby completing the preparation of Compound A86 (yield: 75%).

HRMS for $C_{40}H_{29}N_3[M]+$: calculated: 551.69, found: 550.

Elemental Analysis for $C_{40}H_{29}N_3$ calculated: C, 87.08; H, 5.30; N, 7.62

Synthesis Example 18: Synthesis of Compound A87

Pd(dba)$_3$ (0.03 eq), (t-Bu)$_3$P (0.06 eq), and toluene (based on a reagent (0.1 M 1 eq)) were added to a flask containing Int D-4 (1 eq) and R'-5 (1.2 eq) to form a mixed solution, and then, the mixed solution was stirred under reflux for 5 hours. After the reaction solution was cooled to room temperature, an extraction process was performed thereon using MC, followed by a washing process performed thereon using distilled water. Then, the resulting product obtained from the washing process was subjected to a drying process using MgSO$_4$ and a vacuum distillation process. The residue obtained therefrom was purified by column chromatography, thereby completing the preparation of Compound A87 (yield: 72.7%).

HRMS for $C_{40}H_{29}N_3[M]+$: calculated: 551.69, found: 550.

Elemental Analysis for $C_{40}H_{29}N_3$ calculated: C, 87.08; H, 5.30; N, 7.62

Scheme 3

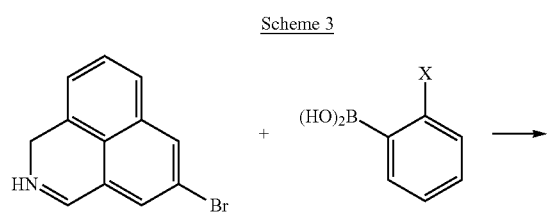

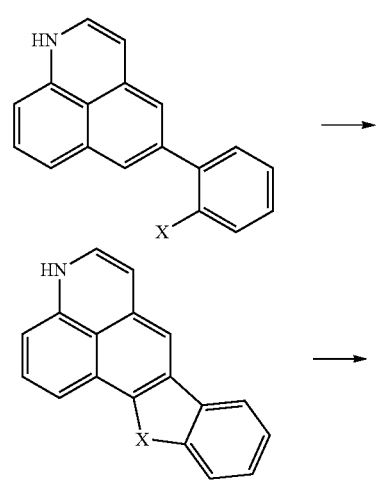

-continued

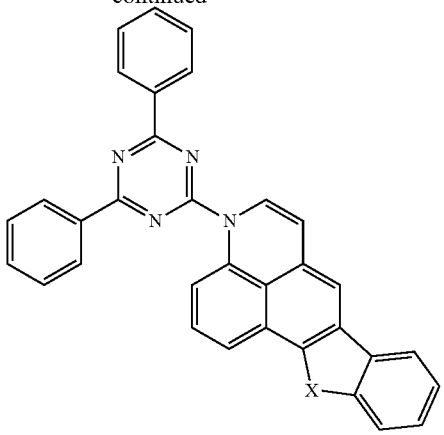

E-1 X = N—Ph
E-2 X = O
E-3 X = S
E-4 X = CCH$_3$CH$_3$

Synthesis Example 19: Synthesis of Compound A89

Compound A89 was obtained according to Scheme 3 in which 5-bromo-1H-benzo[de]quinoline was used as a starting material instead of the 4-bromo-1H-benzo[de]quinoline used in the synthesis of Compound A1.

HRMS for $C_{39}H_{25}N_5[M]+$: calculated: 563.66, found: 562.

Elemental Analysis for $C_{39}H_{25}N_5$ calculated: C, 83.10; H, 4.47; N, 12.42

Synthesis Example 20: Synthesis of Compound A97

Compound A97 was obtained according to Scheme 3 in which 5-bromo-1H-benzo[de]quinoline was used as a starting material instead of the 4-bromo-1H-benzo[de]quinoline used in the synthesis of Compound A41.

HRMS for $C_{33}H_{20}N_4O$ [M]+: calculated: 488.55, found: 487.

Elemental Analysis for $C_{33}H_{20}N_4O$ calculated: C, 81.13; H, 4.13; N, 11.47; O, 3.27

Synthesis Example 21: Synthesis of Compound A93

Compound A93 was obtained according to Scheme 3 in which 5-bromo-1H-benzo[de]quinoline was used as a starting material instead of the 4-bromo-1H-benzo[de]quinoline used in the synthesis of Compound A45.

HRMS for $C_{33}H_{20}N_4S$ [M]+: calculated: 504.61, found: 503.

Elemental Analysis for $C_{33}H_{20}N_4S$ calculated: C, 78.55; H, 4.00; N, 11.10; S, 6.35

Synthesis Example 22: Synthesis of Compound A101

Compound A101 was obtained according to Scheme 3 in which -bromo-1H-benzo[de]quinoline was used as a starting material instead of the 4-bromo-1H-benzo[de]quinoline used in the synthesis of Compound A49.

HRMS for $C_{36}H_{26}N_4$ [M]+: calculated: 514.63, found: 513.

Elemental Analysis for $C_{36}H_{26}N_4$ calculated: C, 84.02; H, 5.09; N, 10.89

EXAMPLES

Examples 1-22

An anode was prepared by cutting a glass substrate (Corning), on which ITO having a thickness of 15 Ω/cm² (1,200 Å) was formed, to a size of 50 mm×50 mm×0.7 mm, ultrasonically cleaning the glass substrate by using isopropyl alcohol and pure water separately for 5 minutes each, and then irradiating UV light for 10 minutes thereto and exposing the glass substrate to ozone to clean the glass substrate. Then, the anode was loaded into a vacuum deposition apparatus.

A material available in the art, 2-TNATA, was deposited on the anode to form a hole injection layer having a thickness of 600 Å, and then, a hole-transporting compound, NPB, was deposited on the hole injection layer to form a hole transport layer having a thickness of 300 Å.

Bis-(1-phenylisoquinolyl) iridium(III)acetylacetonate (Ir (ppy)₃), which is a green light-emitting dopant, and CBP were co-deposited on the hole transport layer at a weight ratio of 15:85 to form an emission layer having a thickness of 300 Å.

Then, the compounds shown in Table 1 were each deposited on the emission layer to form an electron transport layer having a thickness of 300 Å, and Al was vacuum-deposited on the electron transport layer to form a cathode having a thickness of 1,200 Å, thereby forming an Al electrode and completing the manufacture of an organic light-emitting device:

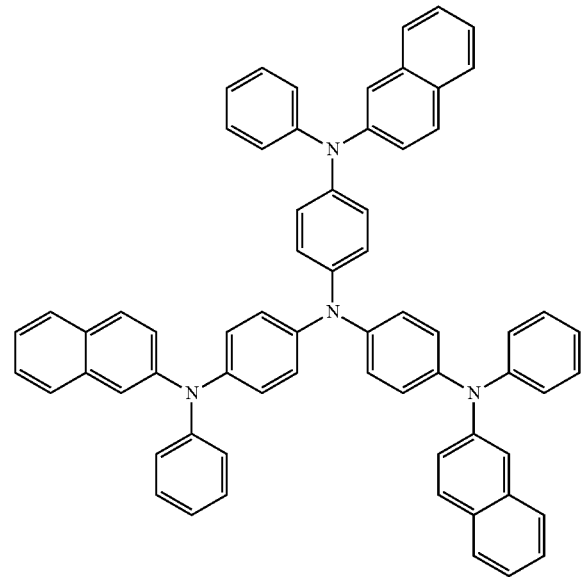

2-TNATA

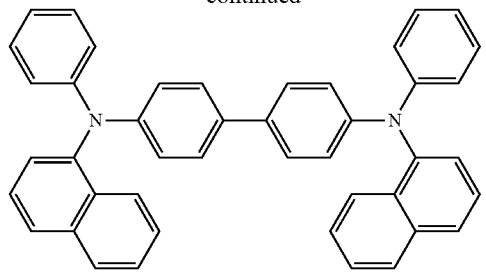

NPB

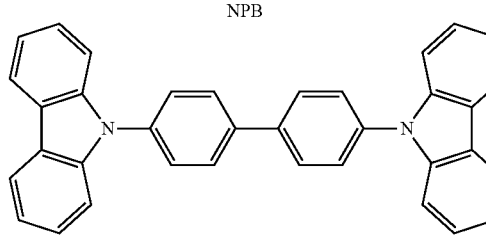

CBP

Comparative Example 1

An organic light-emitting device was manufactured in the same manner as described in connection with Example 1, except that a compound available in the art, Alq₃, was used in the formation of the electron transport layer.

Comparative Example 2

An organic light-emitting device was manufactured in the same manner as described in connection with Example 1, except that Compound Inv 106 was used in the formation of the electron transport layer.

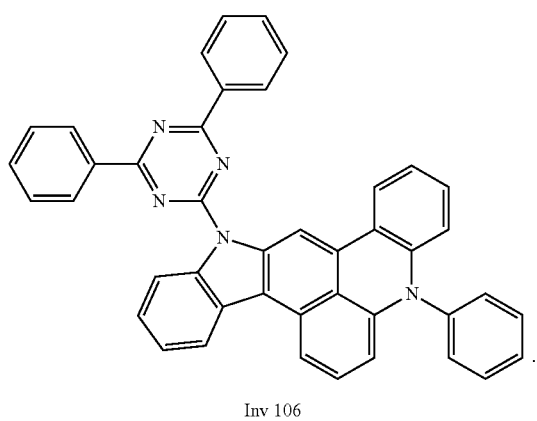 [SMILES: c1ccc(-c2nc(-c3ccccc3)nc(-n3c4ccccc4c4c5cccc6c5c(cc43)-c3ccccc3N6c3ccccc3)n2)cc1]

Inv 106

The composition and properties of the organic light-emitting devices manufactured according to Examples and Comparative Examples described above are summarized in Table 1.

As shown in Table 1, it was confirmed that when the compound according to embodiments of the present disclosure was used as a material for forming the electron transport layer, the efficiency of the organic light-emitting devices increased, especially in terms of lifespan.

TABLE 1

| | Electron transport layer | Efficiency (cd/A) | Lifespan at T$_{95}$ (3,700 nit) |
|---|---|---|---|
| Example 1 | A1 | 51 | 923 |
| Example 2 | A2 | 48.8 | 911 |
| Example 3 | A9 | 47.7 | 897 |
| Example 4 | A14 | 47.9 | 921 |
| Example 5 | A15 | 49.2 | 943 |
| Example 6 | A17 | 48.0 | 937 |
| Example 7 | A23 | 47.9 | 956 |
| Example 8 | A27 | 42 | 942 |
| Example 9 | A35 | 46.4 | 965 |
| Example 10 | A41 | 42.7 | 970 |
| Example 11 | A45 | 51.4 | 985 |
| Example 12 | A49 | 48.1 | 1004 |
| Example 13 | A78 | 55.4 | 1011 |
| Example 14 | A79 | 49.7 | 998 |
| Example 15 | A82 | 51.7 | 964 |
| Example 16 | A83 | 52.3 | 879 |
| Example 17 | A86 | 55 | 957 |
| Example 18 | A87 | 57 | 996 |
| Example 19 | A89 | 50.6 | 1001 |
| Example 20 | A97 | 48.6 | 1105 |
| Example 21 | A93 | 48.4 | 978 |
| Example 22 | A101 | 47.9 | 994 |
| Comparative Example 1 | Alq3 | 38.4 | 789 |
| Comparative Example 2 | Inv 106 | 47.4 | 884 |

As described above, an organic light-emitting device according to one or more embodiments may have improved characteristics by including a compound represented by Formula 1 or Formula 2.

It should be understood that the embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. A compound represented by one selected from Formulae 1 and 2:

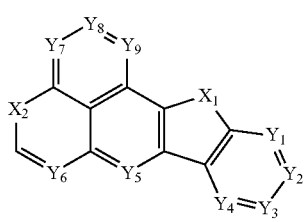

Formula 1

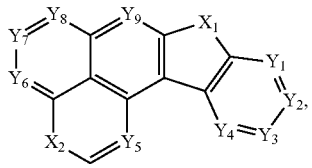

Formula 2 wherein, in Formulae 1 and 2, $X_1$ and $X_2$ are each independently selected from O, S, N(Ar$_1$), and C(Ar$_2$)(Ar$_3$), provided that $X_1$ and $X_2$ are different from or identical to each other and at least one selected from $X_1$ and $X_2$ is N(Ar$_1$), $Y_1$ to $Y_9$ are each independently N or C(R$_1$), provided that $Y_1$ to $Y_9$ are different from or identical to each other, and a plurality of R$_1$s are different from or identical to each other when R$_1$ is plural in number, Ar$_1$ to Ar$_3$ and R$_1$ are each independently selected from hydrogen, deuterium, halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), and —B(Q$_{16}$)(Q$_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group; and a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), and —B(Q$_{26}$)(Q$_{27}$), and Q$_{11}$ to Q$_{17}$ and Q$_{21}$ to Q$_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_1$-C$_{60}$ heteroaryl group, a monovalent non-aromatic condensed polycyclic group, and a monovalent non-aromatic condensed heteropolycyclic group.

2. The compound of claim 1, wherein, in Formulae 1 and 2, Ar$_2$ and Ar$_3$ are each independently selected from a substituted or unsubstituted C$_1$-C$_{60}$ alkyl group, a substituted or unsubstituted C$_6$-C$_{60}$ aryl group, and a substituted or unsubstituted C$_1$-C$_{60}$ heteroaryl group.

3. The compound of claim 1, wherein, in Formulae 1 and 2, at least one Ar$_1$ is one selected from groups represented by Formulae 2a to 2g:

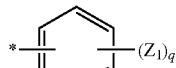
2a

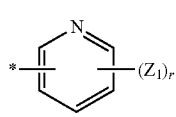
2b

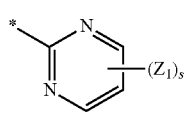
2c

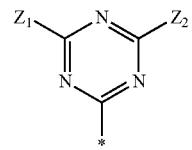
2d

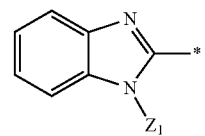
2e

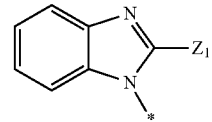
2f

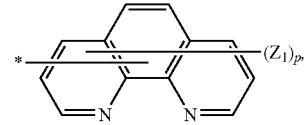
2g wherein, in Formulae 2a to 2g, Z$_1$ and Z$_2$ are each independently selected from hydrogen, deuterium, halogen, a substituted or unsubstituted C$_1$-C$_{20}$ alkyl group, a substituted or unsubstituted C$_6$-C$_{20}$ aryl group, a substituted or unsubstituted C$_1$-C$_{20}$ heteroaryl group, a substituted or unsubstituted monovalent non-aromatic condensed polycyclic group, and a substituted or unsubstituted monovalent non-aromatic condensed heteropolycyclic group, p is an integer selected from 1 to 7, q is an integer selected from 1 to 5, r is an integer selected from 1 to 4, and s is an integer selected from 1 to 3, Z$_1$s are identical to or different from each other, when one selected from p, q, r, and s is two or more, and

* indicates a binding site.

4. The compound of claim 1, wherein the compound represented by one selected from Formulae 1 and 2 is represented by one selected from Formulae 3 and 4, respectively:

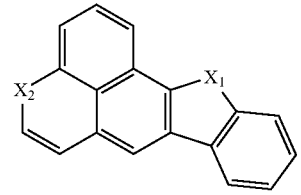
Formula 3

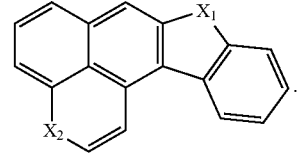
Formula 4

5. The compound of claim 1, wherein the compound represented by one selected from Formulae 1 and 2 is represented by one selected from Formulae 5 and 6, respectively:

Formula 5
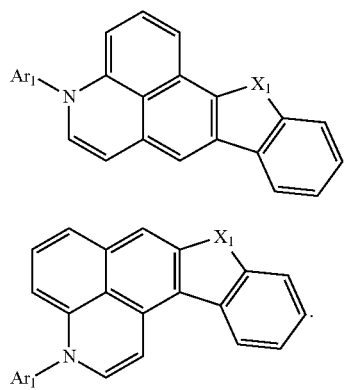
Formula 6
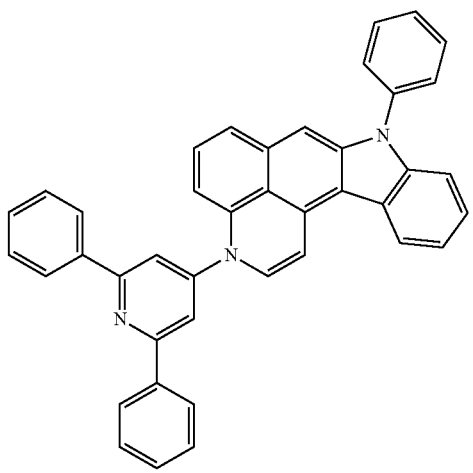
6. The compound of claim 1, wherein the compound represented by one selected from Formulae 1 and 2 is selected from the following compounds:
A1
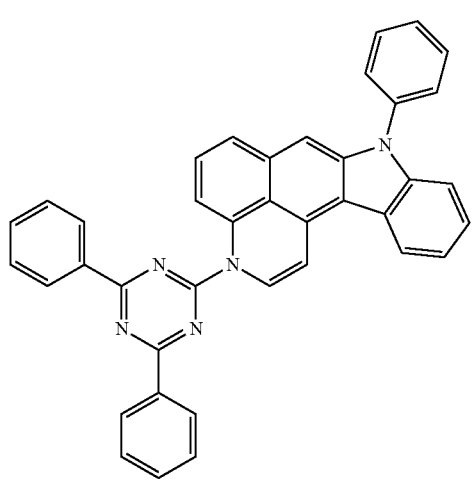
A2
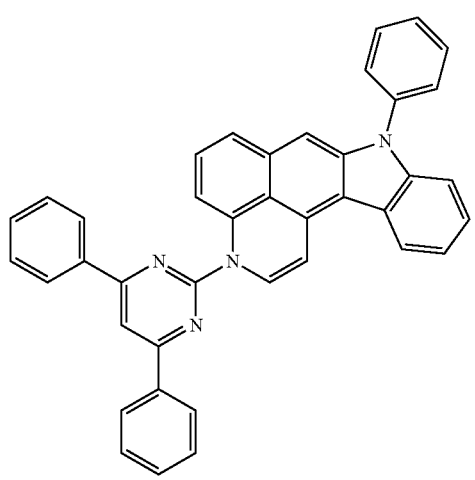
A3
A4
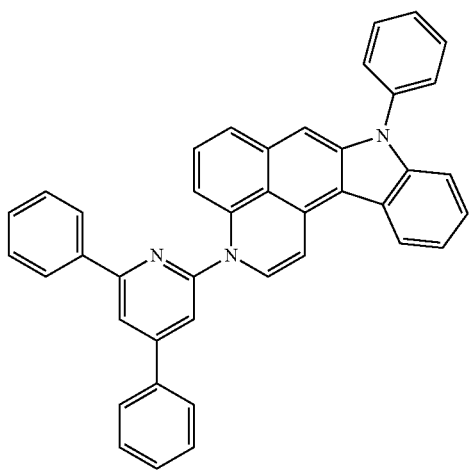
A5
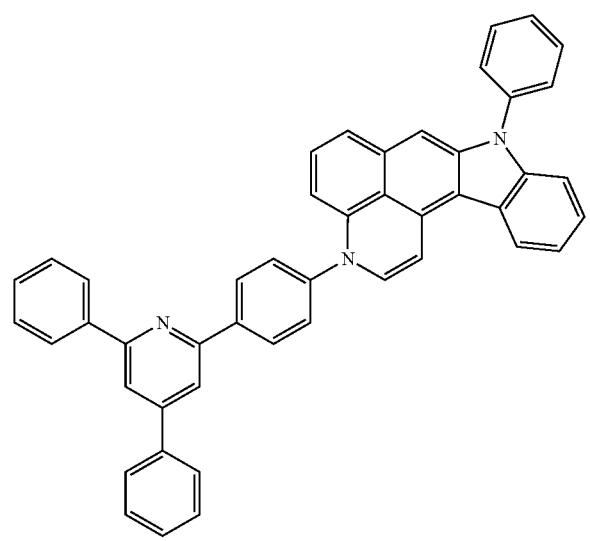

-continued
A6
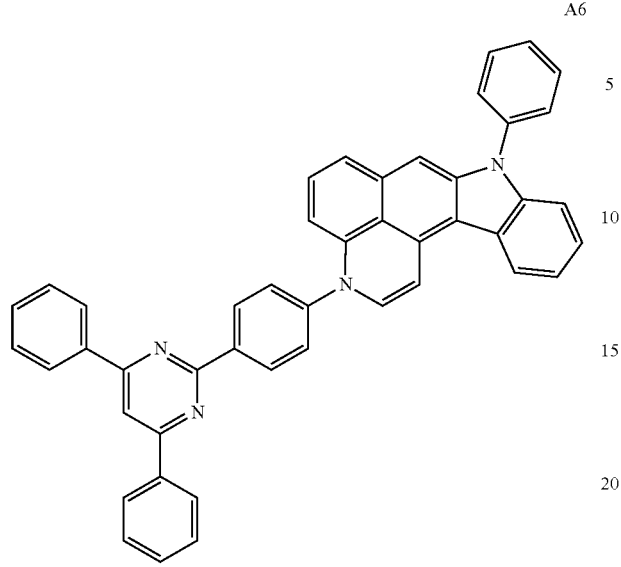
A7
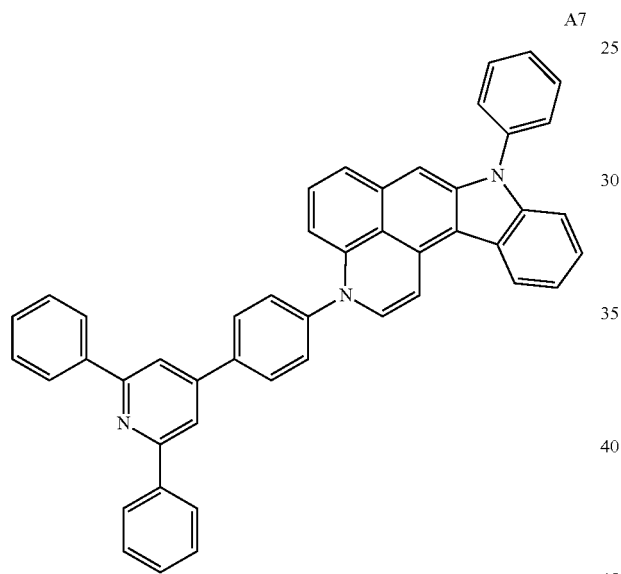
A8
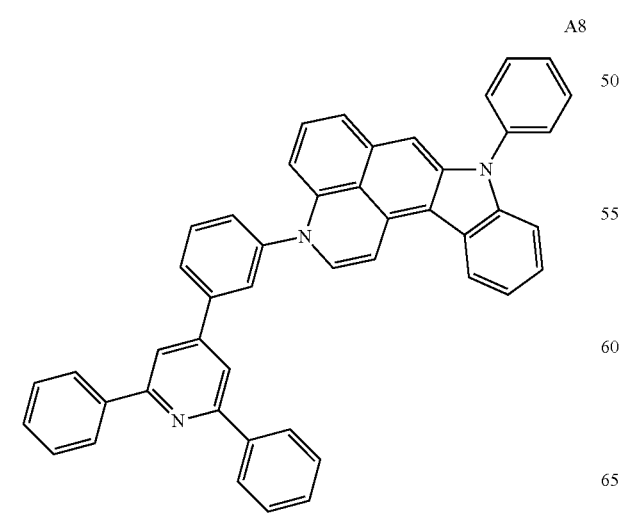
-continued
A9
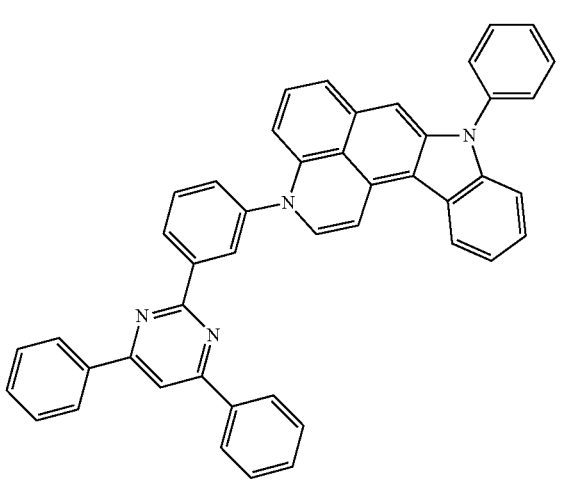
A10
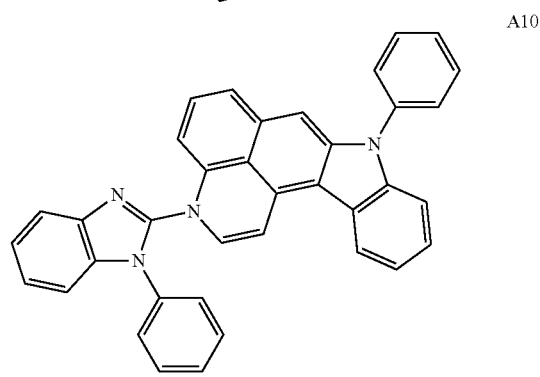
A11
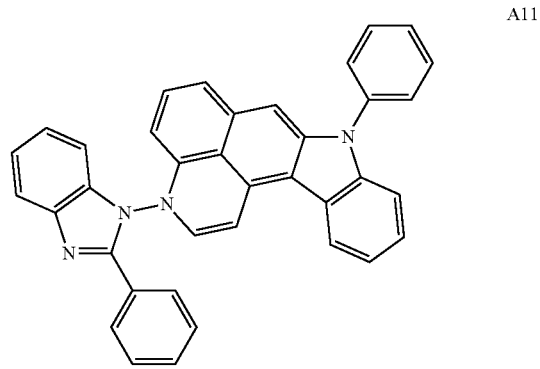
A12
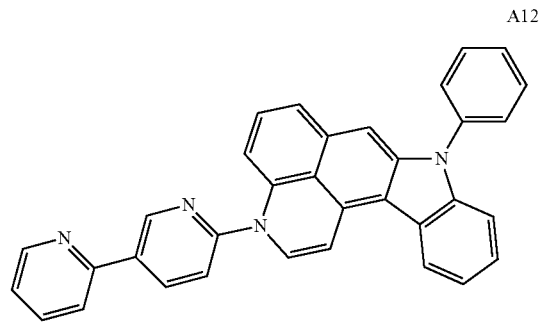

A13
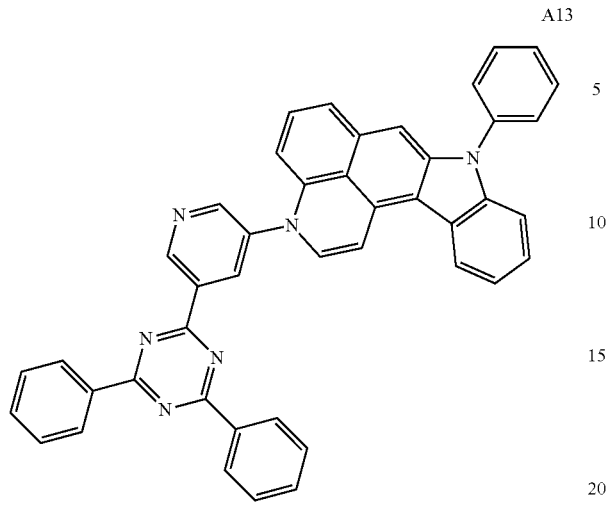
A17
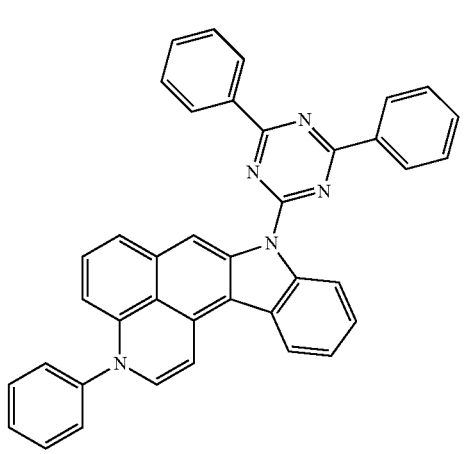
A14
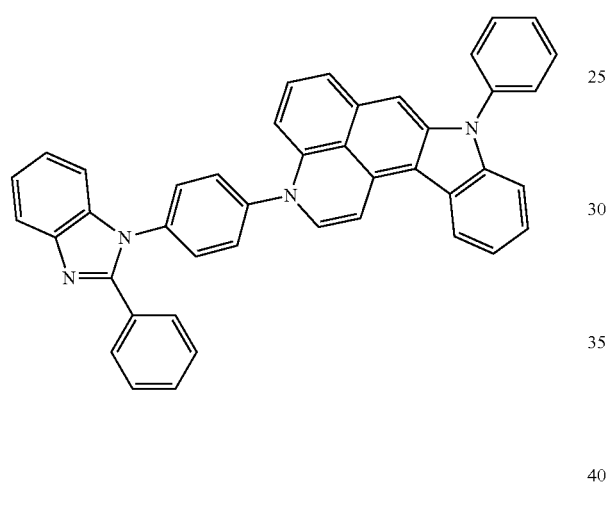
A18
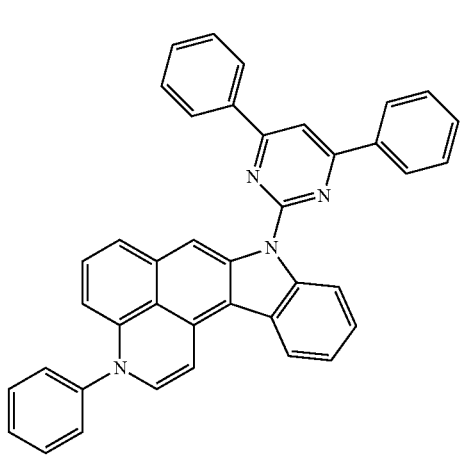
A15
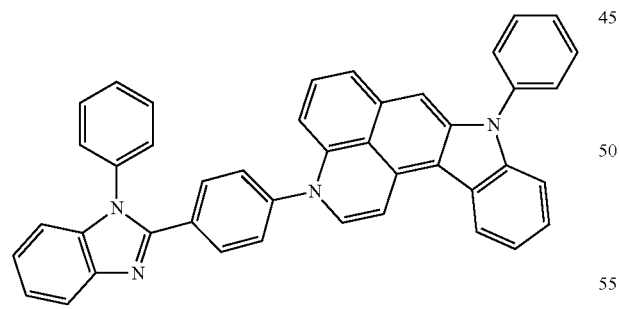
A19
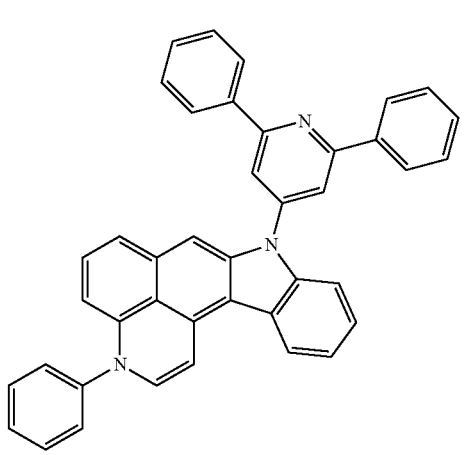
A16
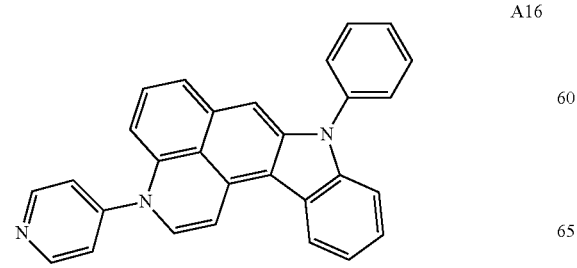

-continued
A20
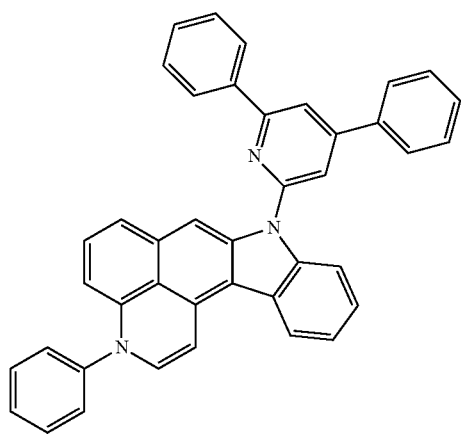
A21
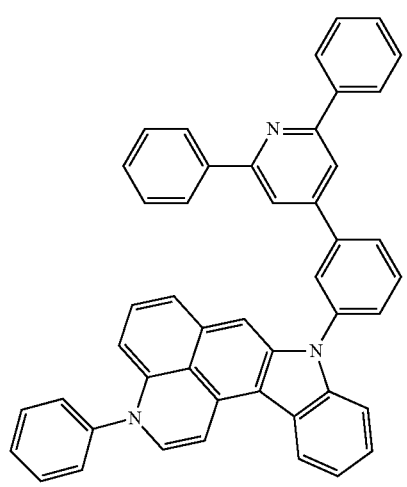
A22
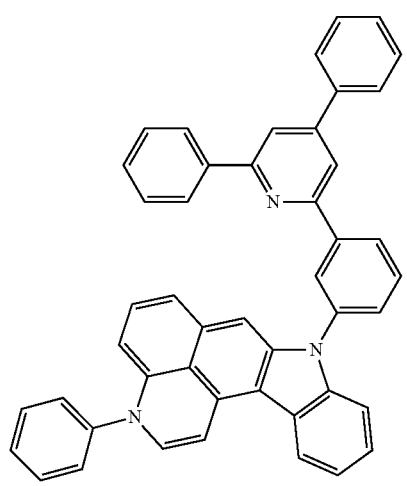
-continued
A23
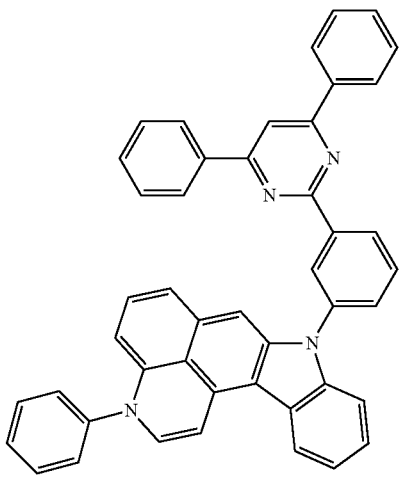
A24
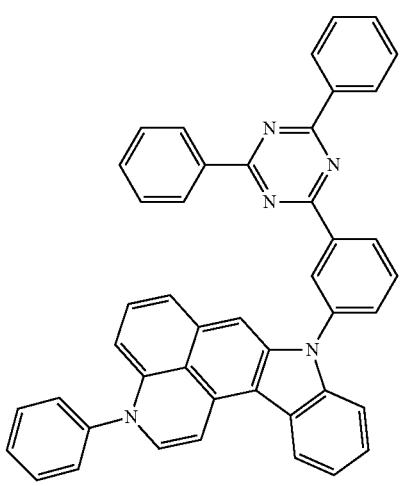
A25
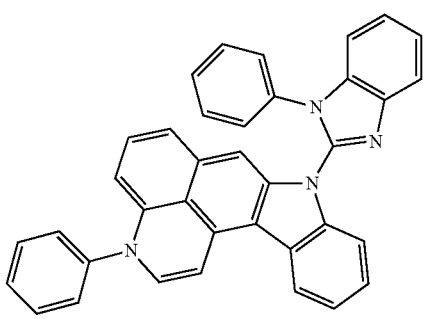

A26
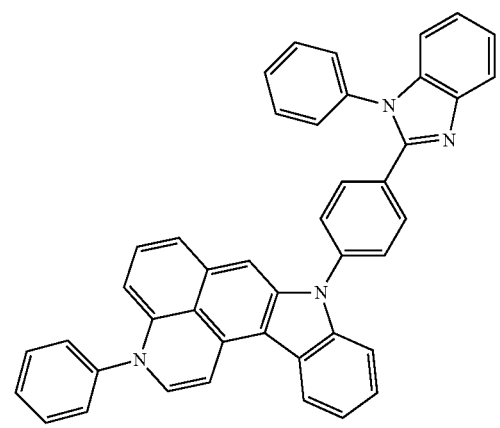
A27
A28
A29
A30
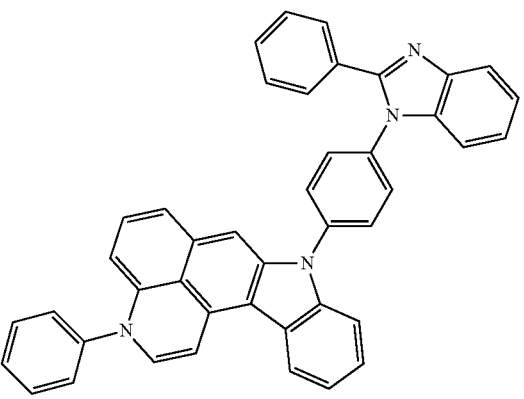
A31
A32
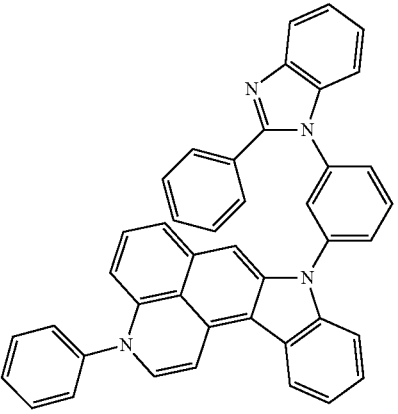
A33
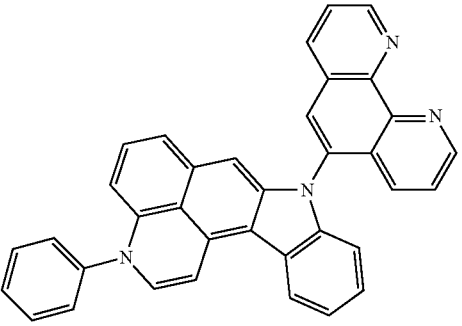

-continued
A34
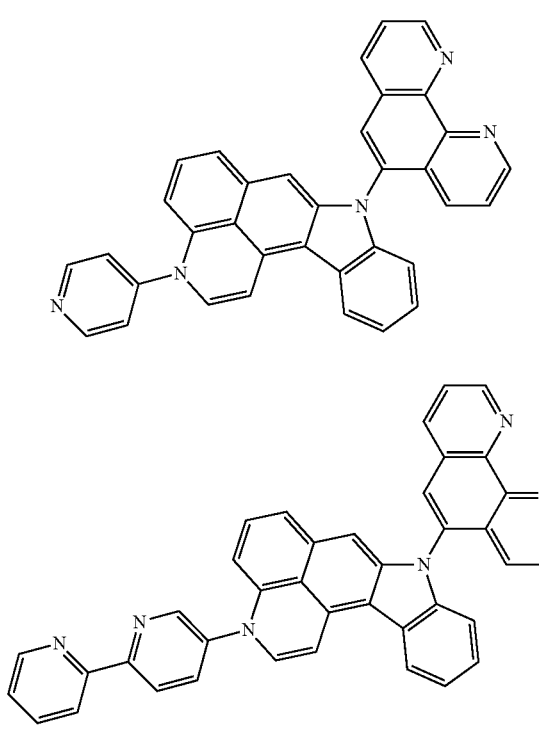
A35
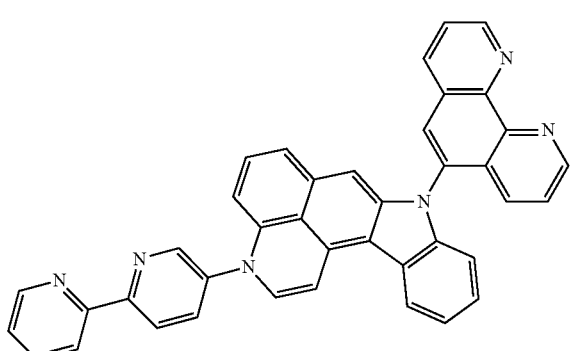
A36
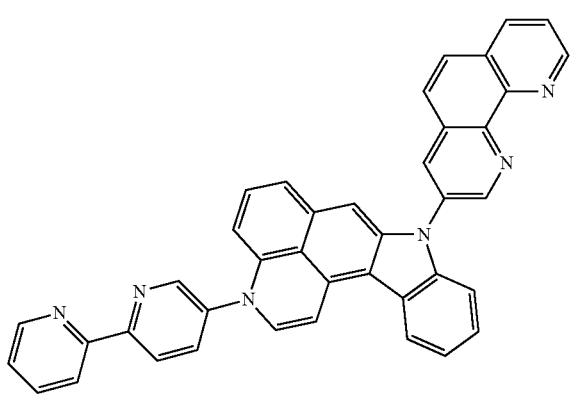
A37
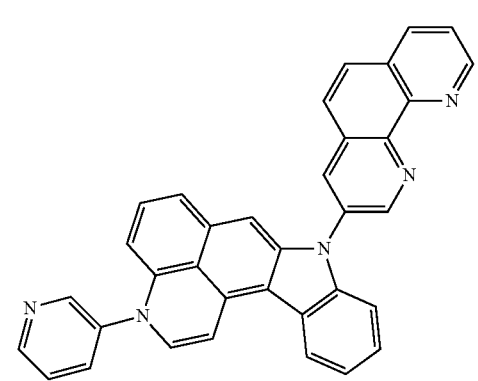
-continued
A38
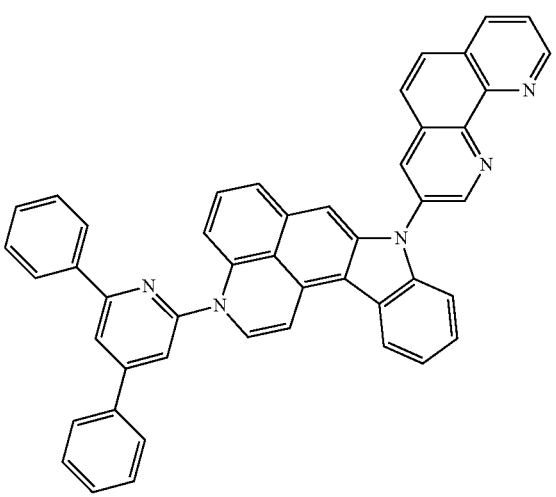
A39
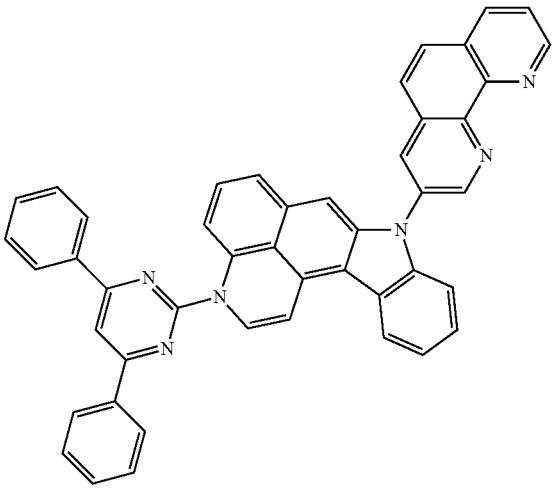
A40
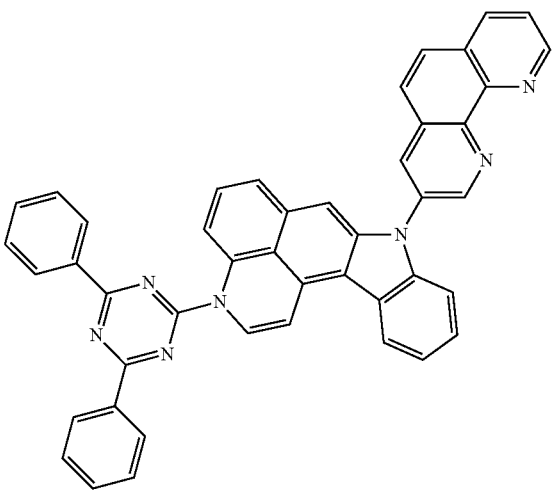

A41 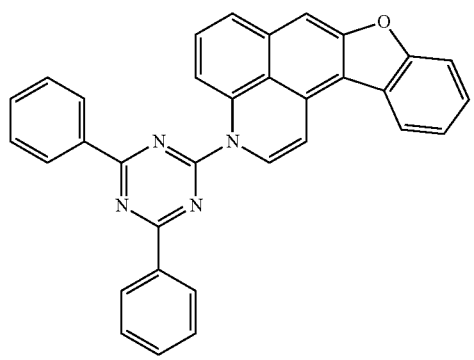
A42 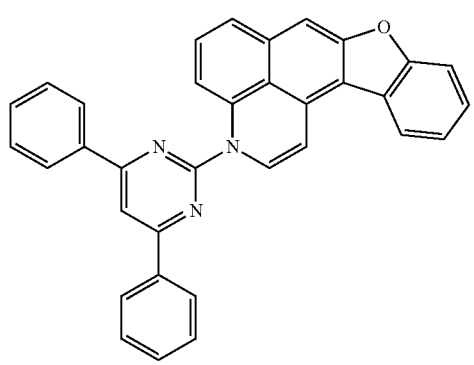
A43 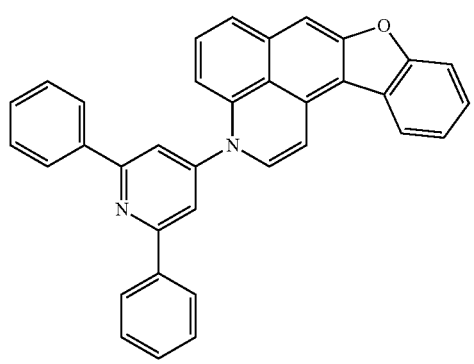
A44 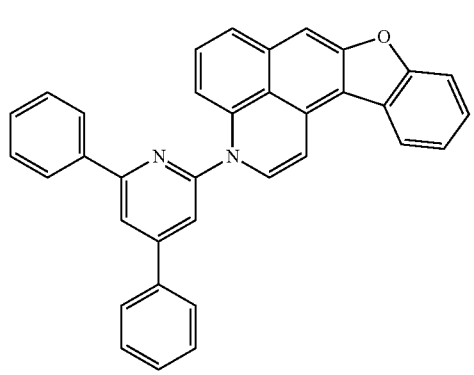
A45 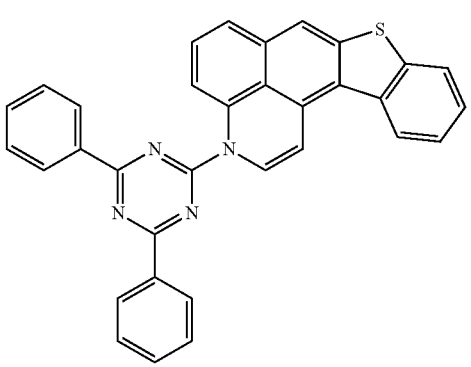
A46 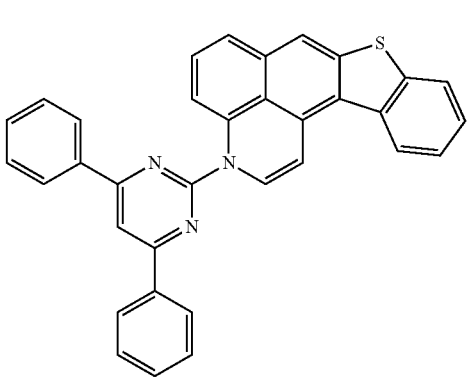
A47 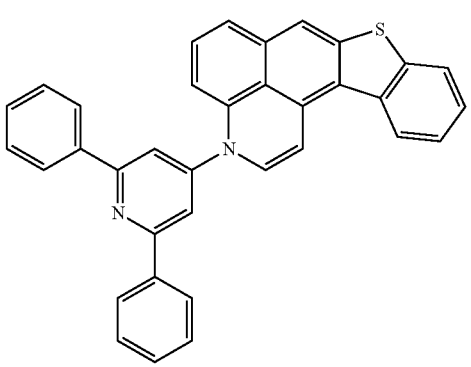
A48 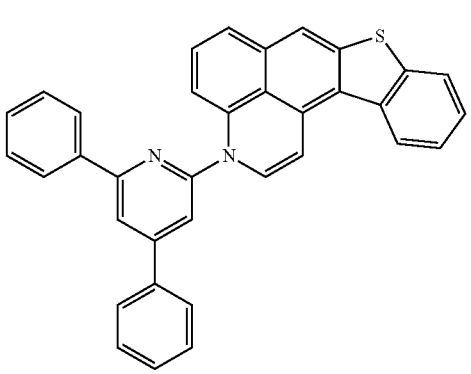

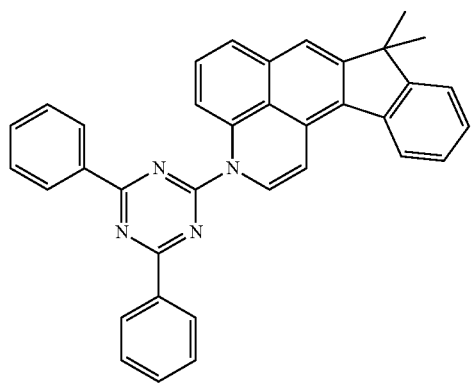
A49
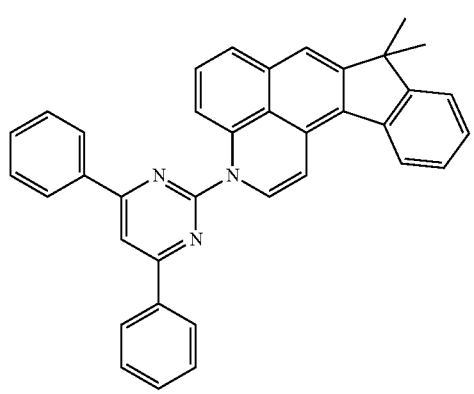
A50
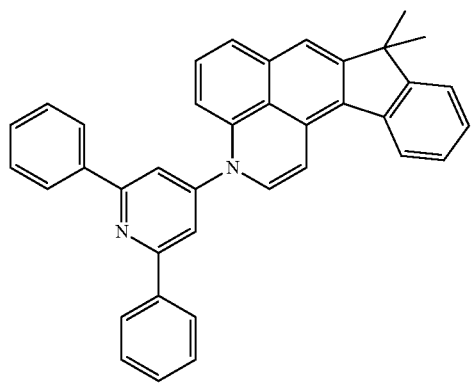
A51
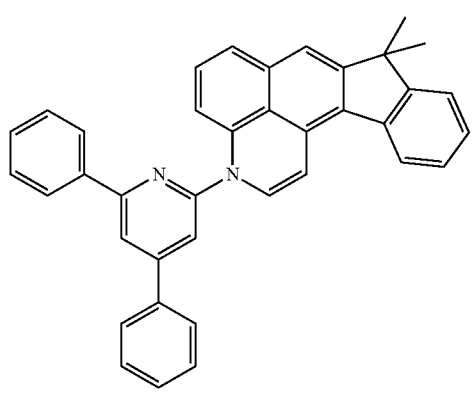
A52
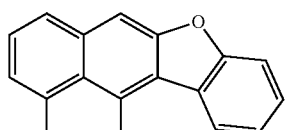
A53
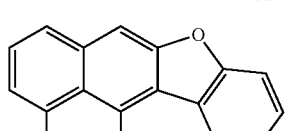
A54
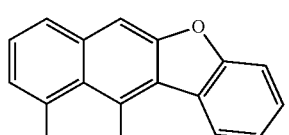
A55

-continued
A56
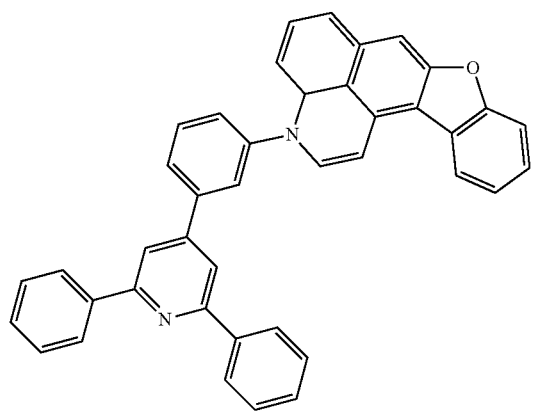
A57
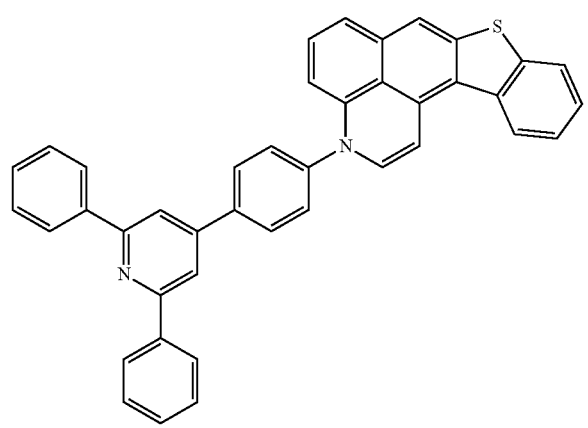
A58
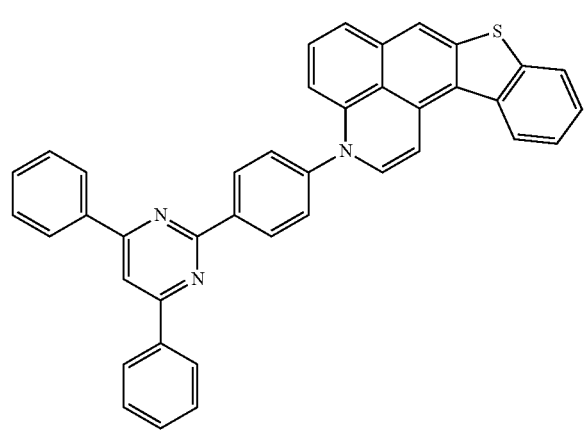
-continued
A59
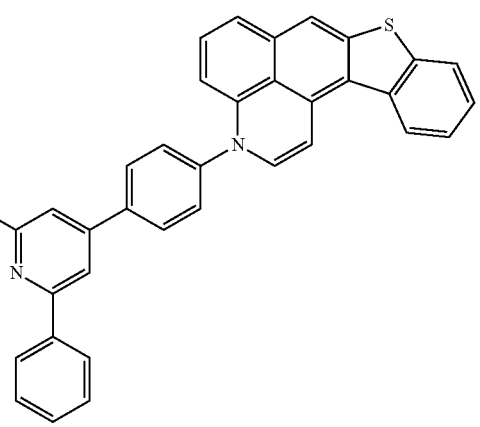
A60
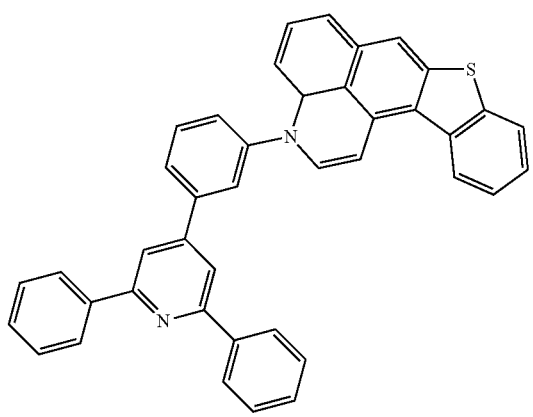
A61
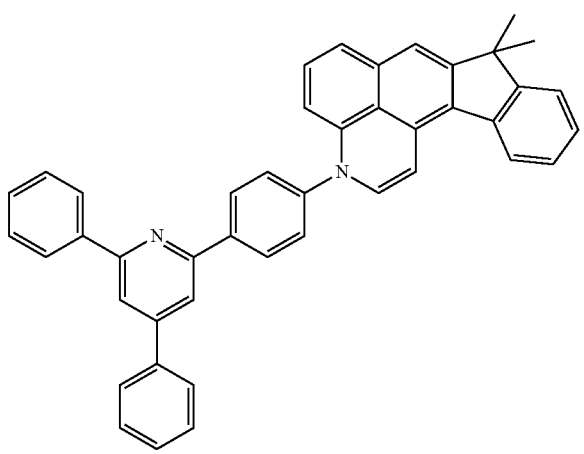

-continued
A62
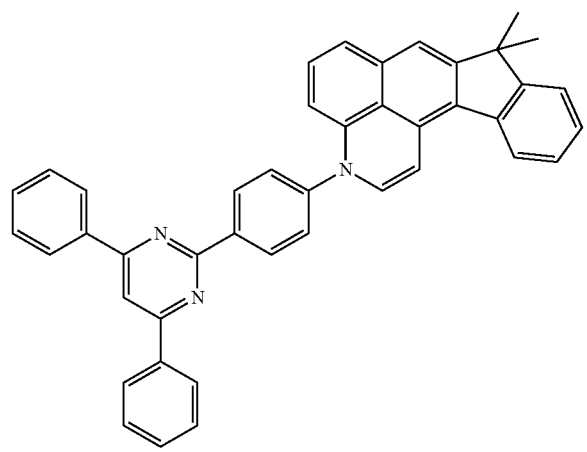
A63
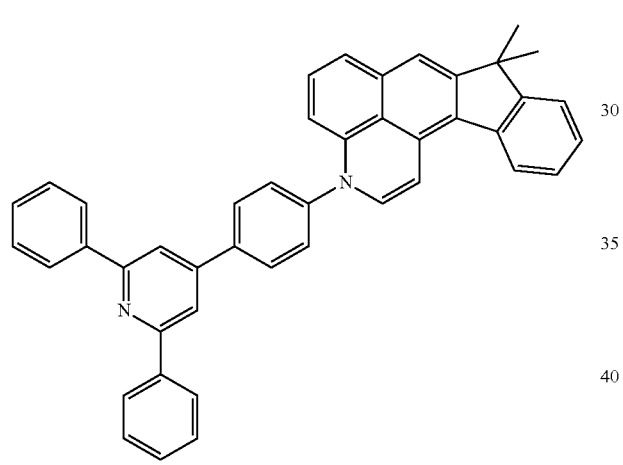
A64
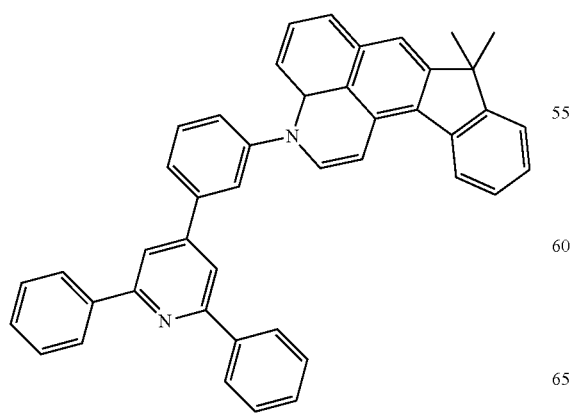
-continued
A65
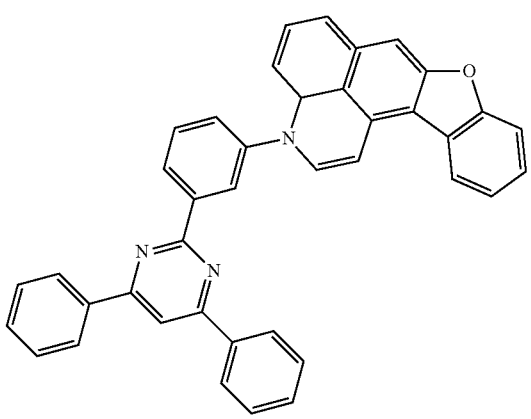
A66
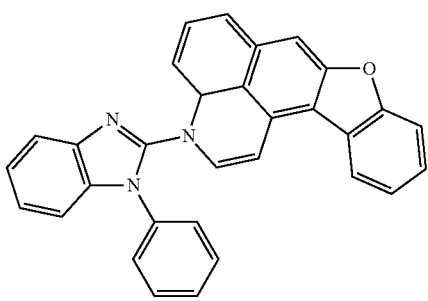
A67
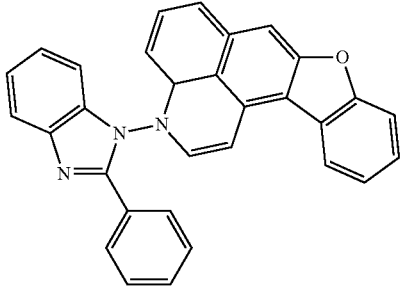
A68
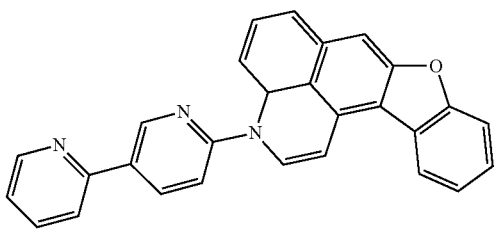

A69
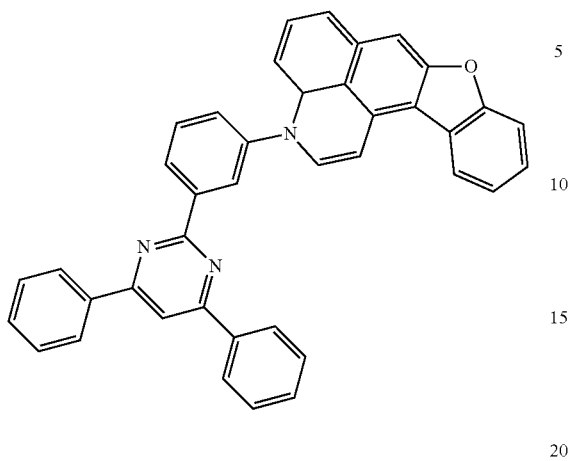
A70
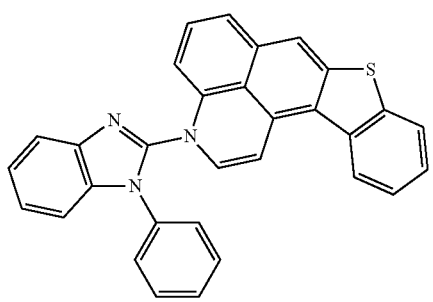
A71
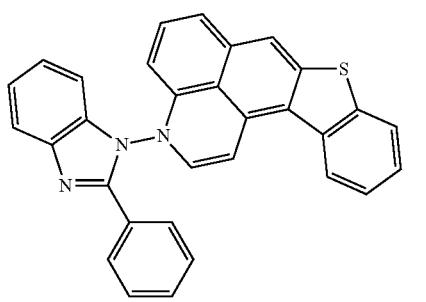
A72
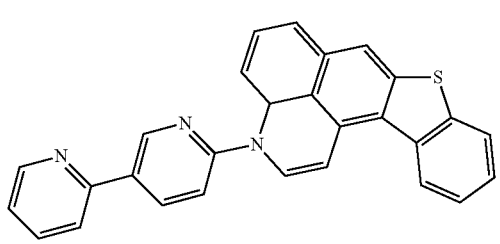
A73
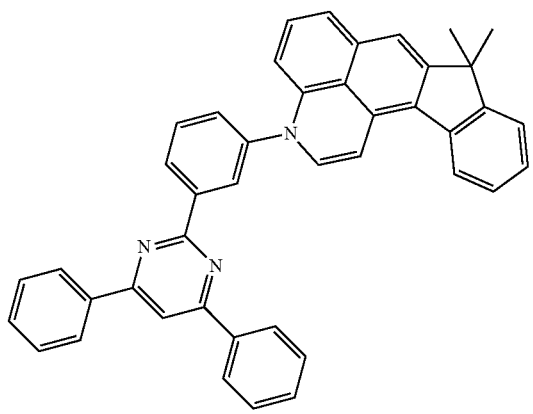
A74
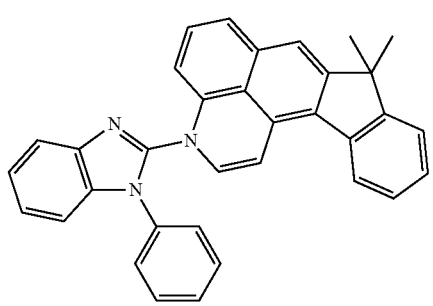
A75
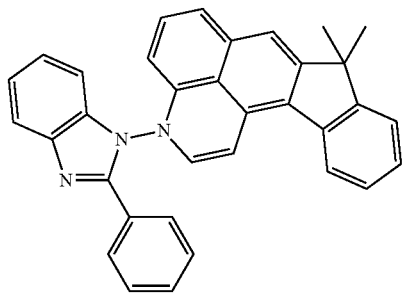
A76
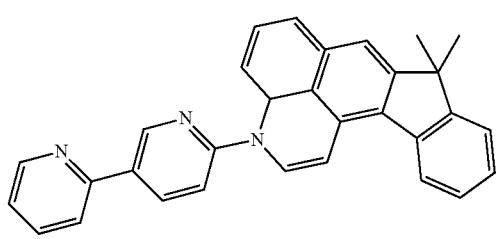

A77
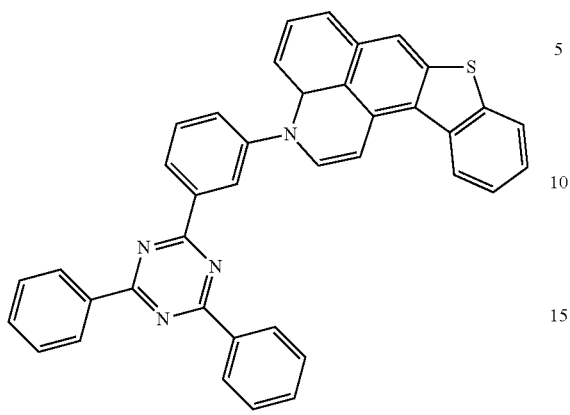
A78
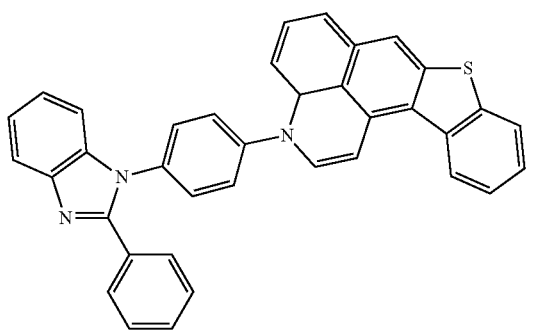
A79
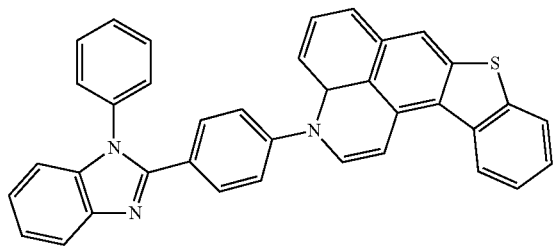
A80
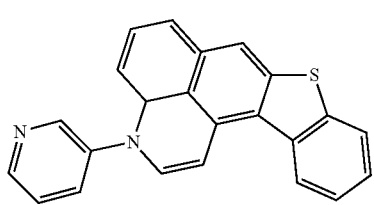
A81
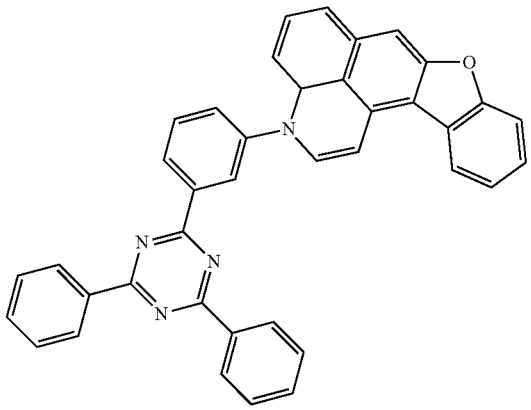
A82
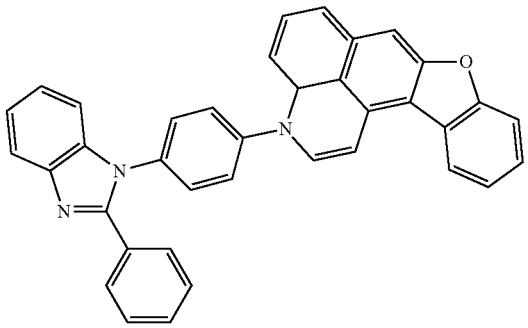
A83
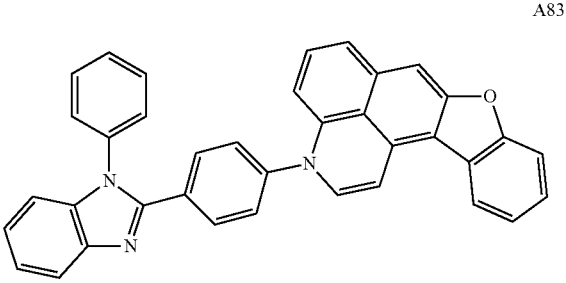
A84
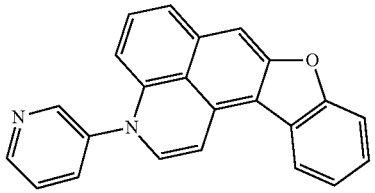

A85
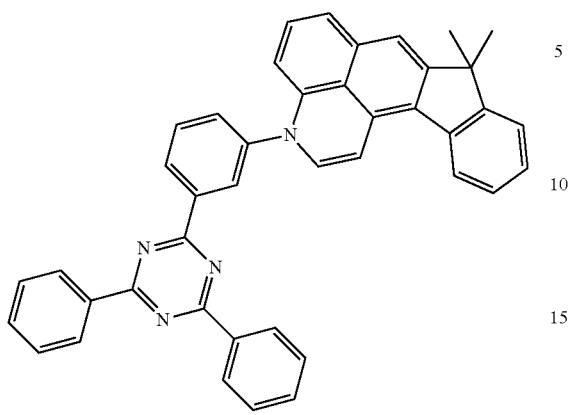
A86
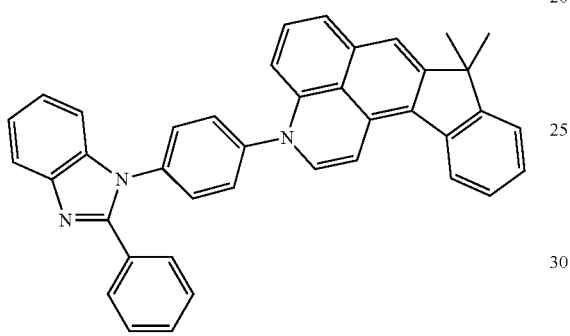
A87
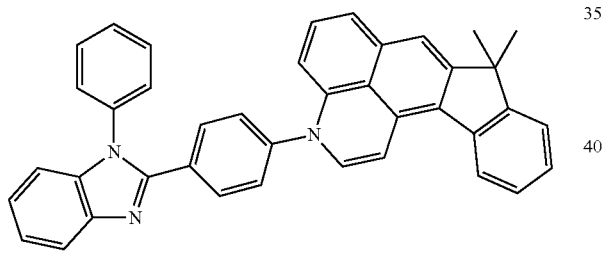
A88
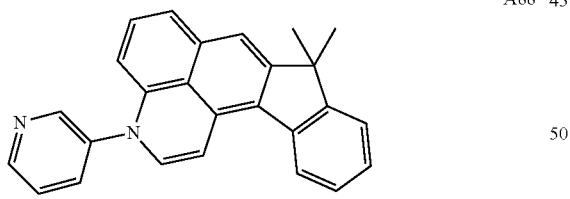
A89
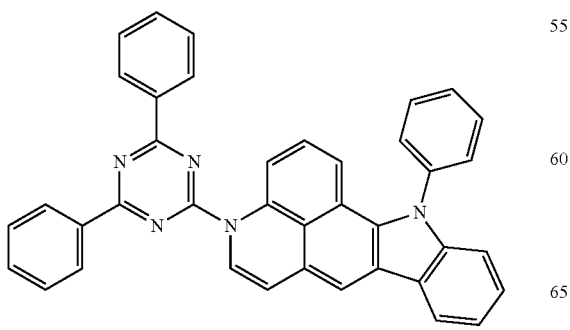
A90
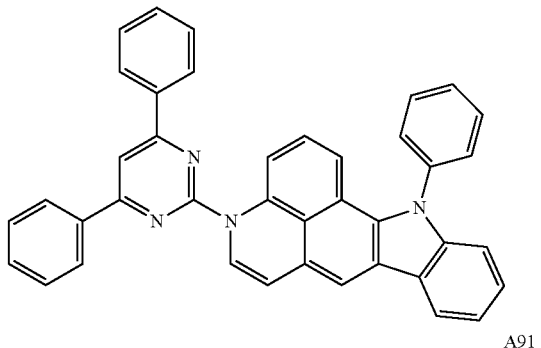
A91
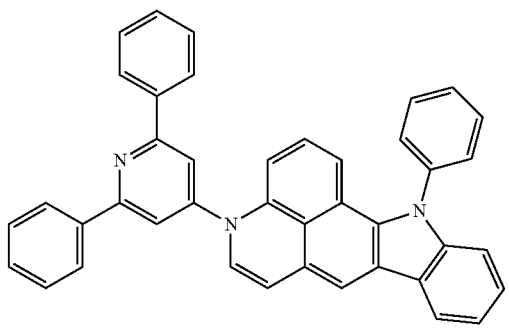
A92
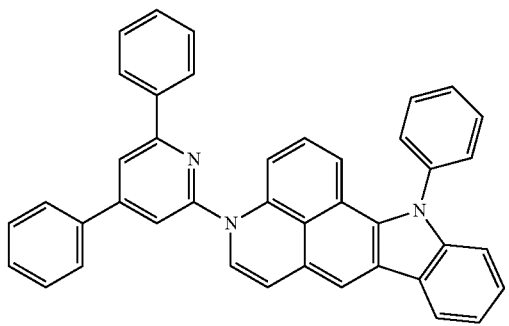
A93
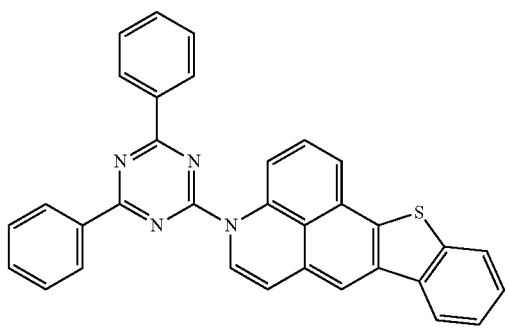

-continued
A94
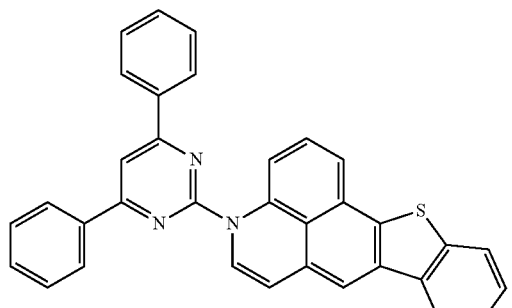
A95
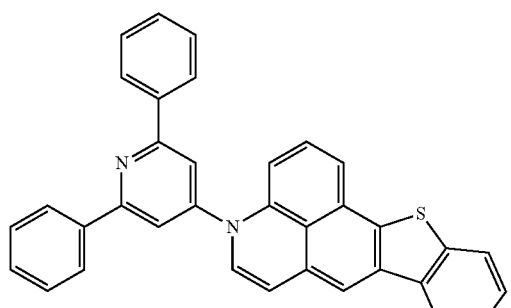
A96
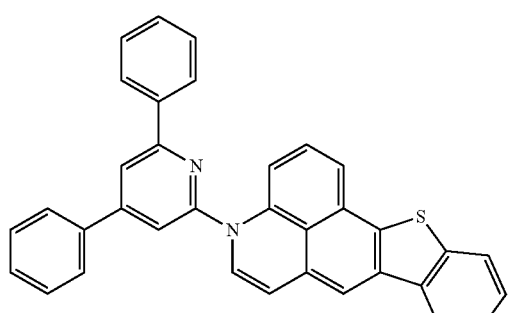
A97
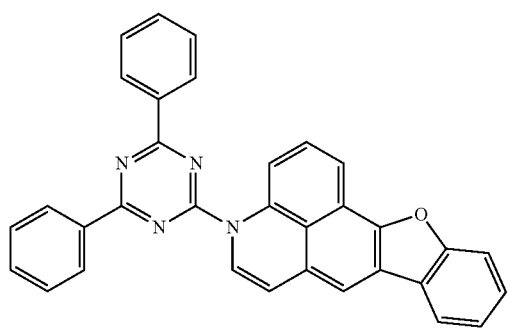
A98
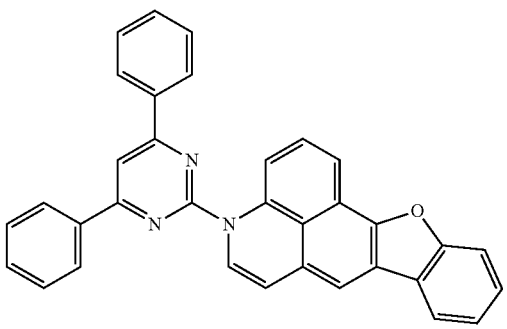
A99
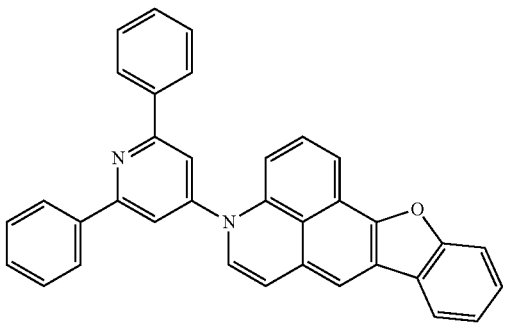
A100
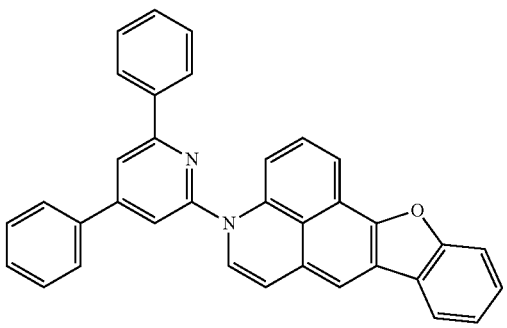
A101
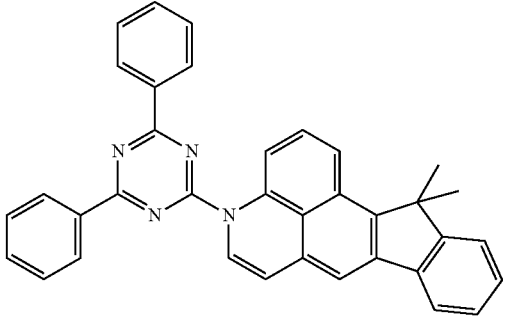

-continued
A102
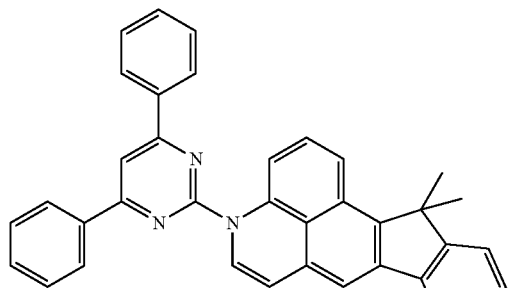
A103
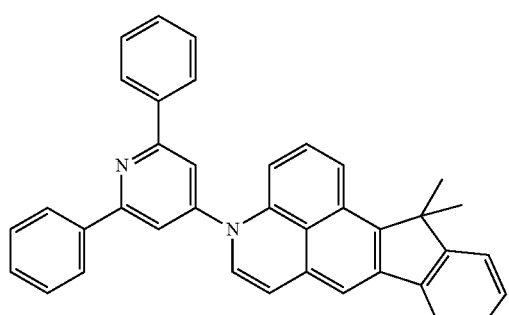
A104
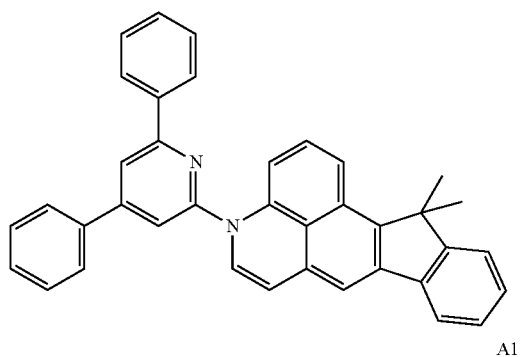
A105
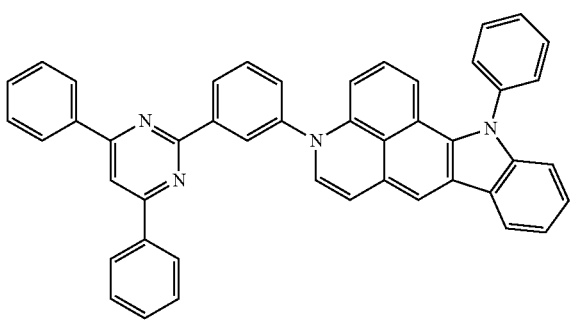
-continued
A106
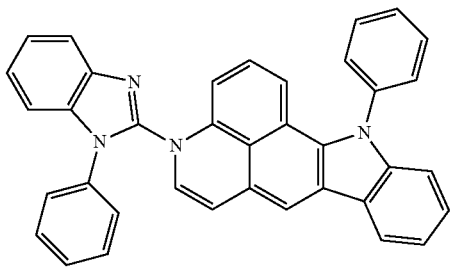
A107
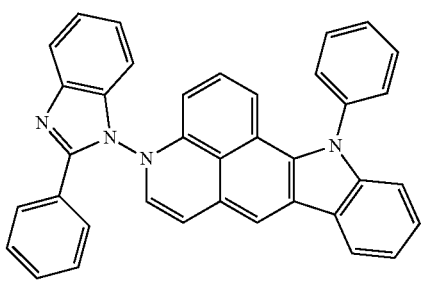
A108
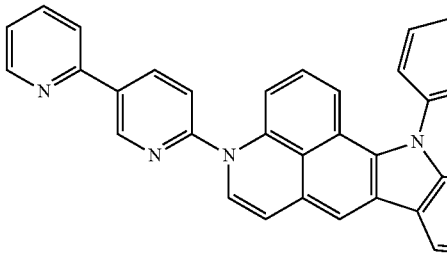
A109
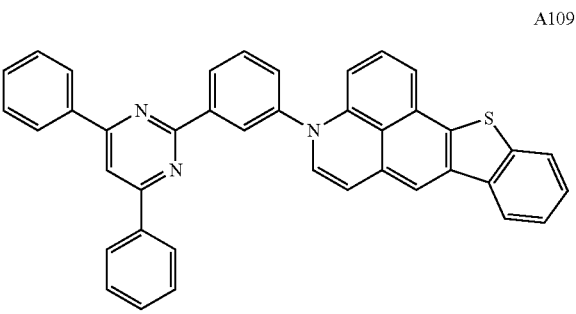
A110
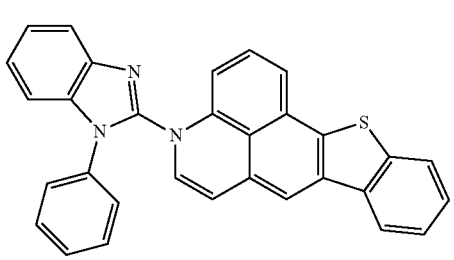

A111
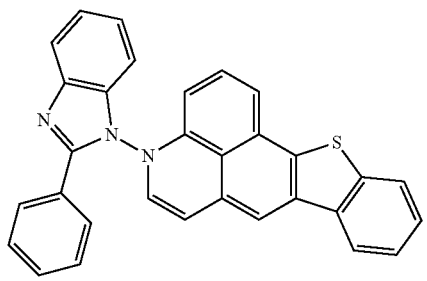
A112
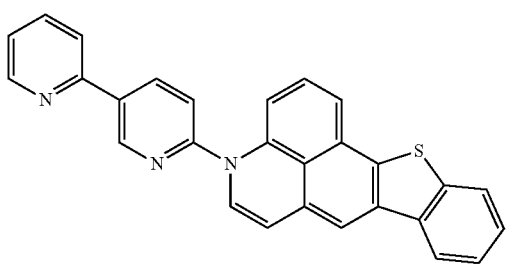
A113
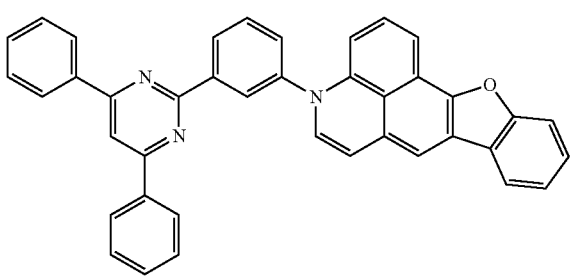
A114
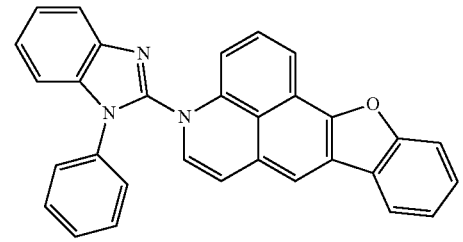
A115
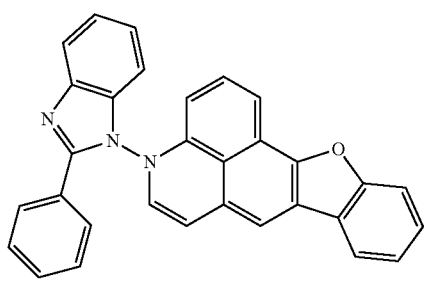
A116
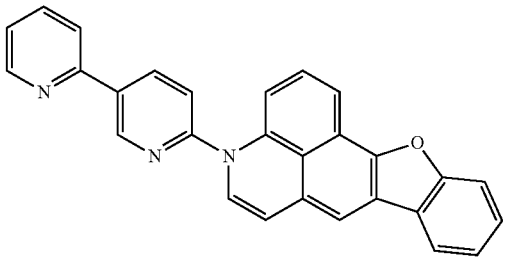
A117
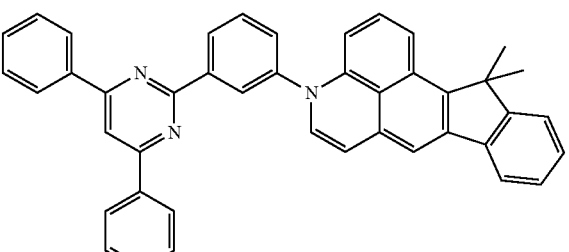
A118
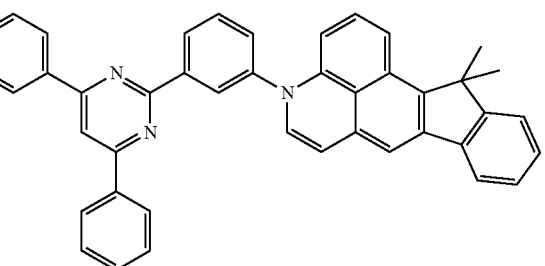
A119
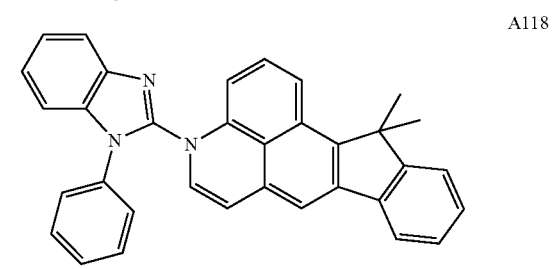
A120
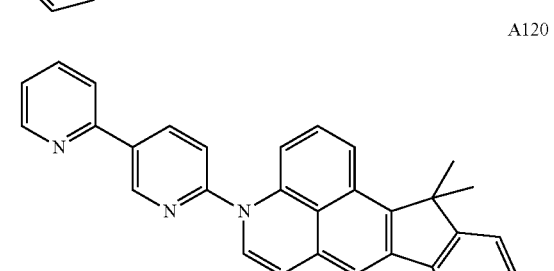
7. An organic light-emitting device comprising:
a first electrode;
a second electrode facing the first electrode; and
an organic layer between the first electrode and the second electrode, the organic layer comprising an emission layer,
wherein the organic layer comprises the compound of claim 1.

8. The organic light-emitting device of claim 7, wherein the organic layer is formed using a solution process.

9. The organic light-emitting device of claim 7, wherein the first electrode is an anode, the second electrode is a cathode, and the organic layer comprises at least one selected from:
  i) a hole transport region between the first electrode and the emission layer and comprising at least one selected from a hole injection layer, a hole transport layer, and an electron blocking layer; and
  ii) an electron transport region between the emission layer and the second electrode and comprising at least one selected from an electron transport layer, a hole blocking layer, and an electron injection layer.

10. The organic light-emitting device of claim 9, wherein the electron transport region comprises the compound.

11. The organic light-emitting device of claim 9, wherein the electron transport layer comprises the compound.

12. The organic light-emitting device of claim 9, wherein the hole transport region comprises a charge-generation material.

13. The organic light-emitting device of claim 12, wherein the charge-generation material is a p-dopant.

14. The organic light-emitting device of claim 12, wherein the charge-generation material is selected from tetracyanoquinodimethane (TCNQ), 2,3,5,6-tetrafluoro-7,7,8,8-tetracyanoquinodimethane (F4-TCNQ), a metal oxide, 1,4,5,8,9,11-hexaazatriphenylene-hexacarbonitrile (HAT-CN), and a compound represented by Formula 221:

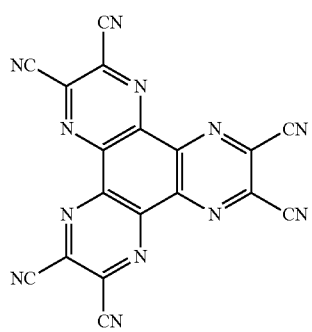

HAT-CN

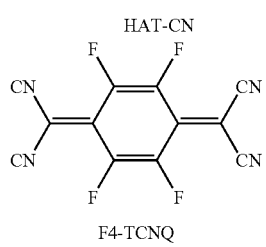

F4-TCNQ

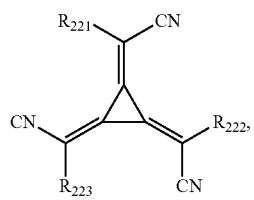

Formula 221 wherein, in Formula 221, $R_{221}$ to $R_{223}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

15. The organic light-emitting device of claim 9, wherein the electron transport region comprises a metal-containing material.

16. The organic light-emitting device of claim 9, wherein the electron transport region comprises a lithium (Li) complex.

17. The organic light-emitting device of claim 9, wherein the electron transport region comprises Compound ET-D1 or Compound ET-D2:

ET-D1

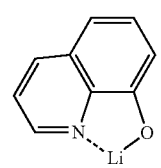

ET-D2

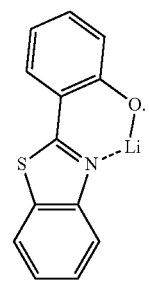

18. A display device comprising the organic light-emitting device of claim 9, wherein the first electrode of the organic light-emitting device is electrically coupled with a source electrode or a drain electrode of a thin film transistor.

19. A compound represented by one selected from Formulae 3 and 4:

Formula 3

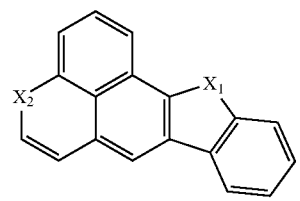

Formula 4

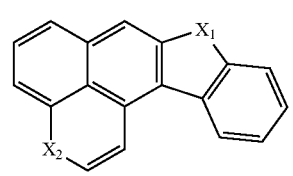

wherein, in Formulae 3 and 4, $X_1$ and $X_2$ are each independently selected from O, S, $N(Ar_1)$, and $C(Ar_2)(Ar_3)$, provided that $X_1$ and $X_2$ are different from or identical to each other and at least one selected from $X_1$ and $X_2$ is $N(Ar_1)$, $Ar_2$ and $Ar_3$ are each independently selected from hydrogen, deuterium, halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$, and $Q_{11}$ to $Q_{17}$ and $Q_{21}$ to $Q_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, wherein at least one $Ar_1$ is one selected from groups represented by Formulae 2a to 2g:

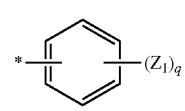

2a

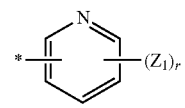

2b

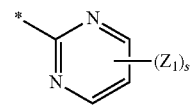

2c

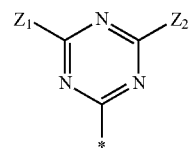

2d

-continued

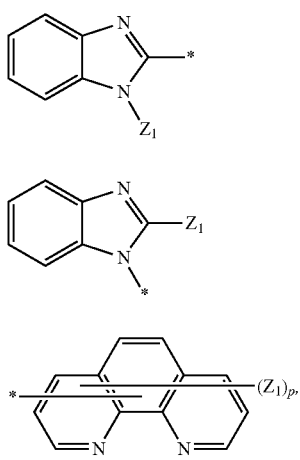

2e

2f

2g wherein, in Formulae 2a to 2g, $Z_1$ and $Z_2$ are each independently selected from hydrogen, deuterium, halogen, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p is an integer selected from 1 to 7, q is an integer selected from 1 to 5, r is an integer selected from 1 to 4, and s is an integer selected from 1 to 3, $Z_1$s are identical to or different from each other, when one selected from p, q, r, and s is two or more, and

* indicates a binding site.

20. The compound of claim 19, wherein the compound represented by one selected from Formulae 3 and 4 is represented by one selected from Formulae 5 and 6, respectively:

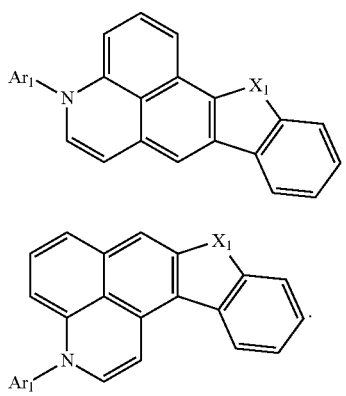

Formula 5

Formula 6

21. The compound of claim 19, wherein $Ar_2$ and $Ar_3$ are each a methyl group.

22. The compound of claim 19, wherein at least one $Ar_1$ is one selected from groups represented by Formulae 3a to 3i:

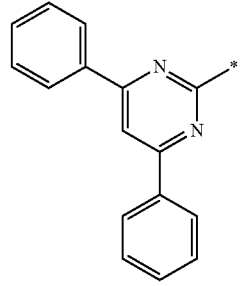

3a

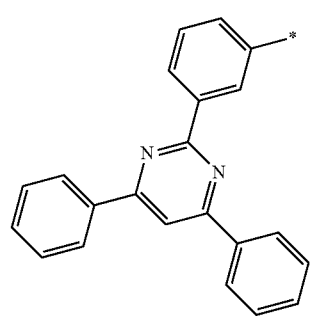

3b

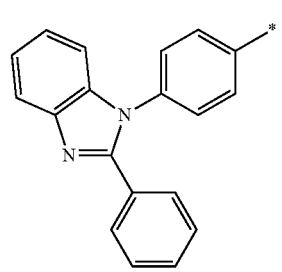

3c

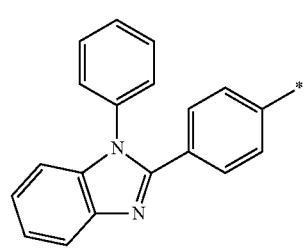

3d

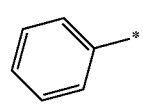

3e

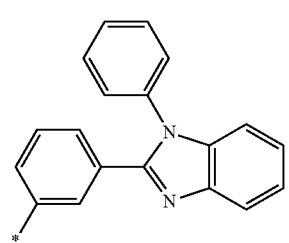

3f

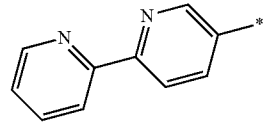

3g

3h
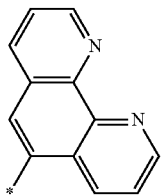
3i
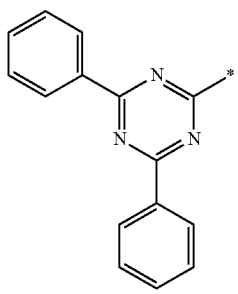
wherein, in Formulae 3a to 3i, * indicates a binding site.
23. The compound of claim 19, wherein the compound represented by one selected from Formulae 3 and 4 is selected from compounds A1, A2, A9, A14, A15, A17, A23, A27, A35, A41, A45, A49, A78, A79, A82, A83, A86, A87, A89, A93, A97, and A101:
A1
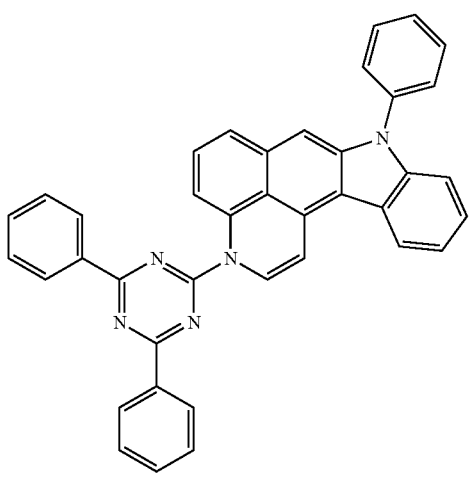
A2
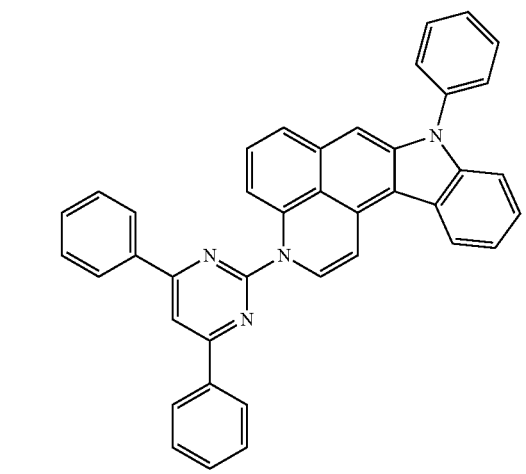
A9
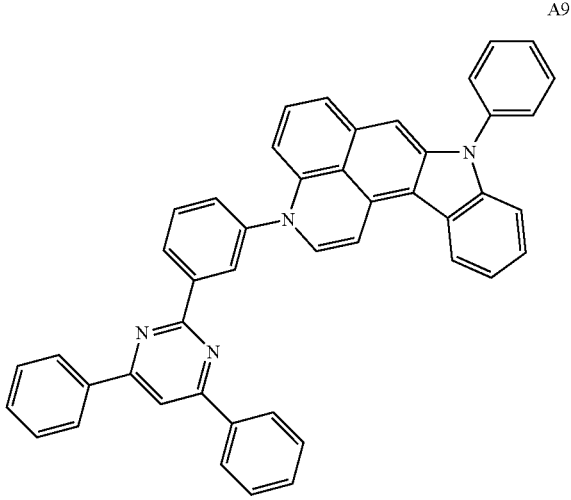
A14
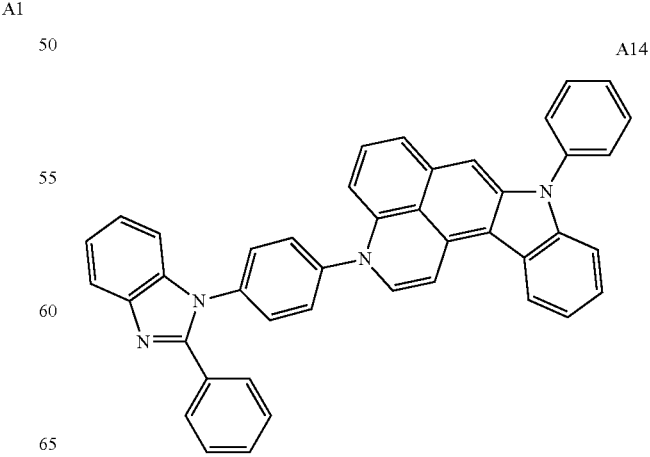

A15
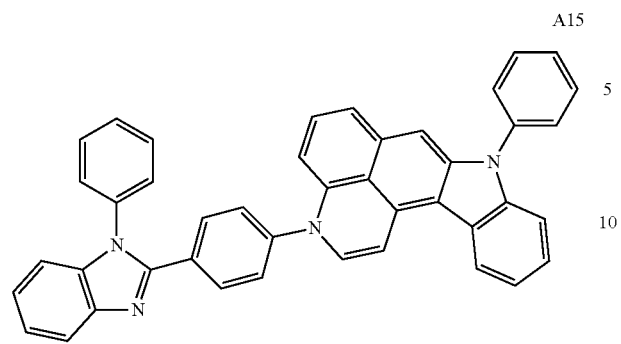
A17
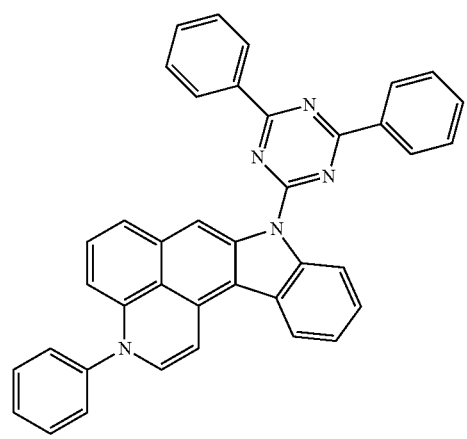
A23
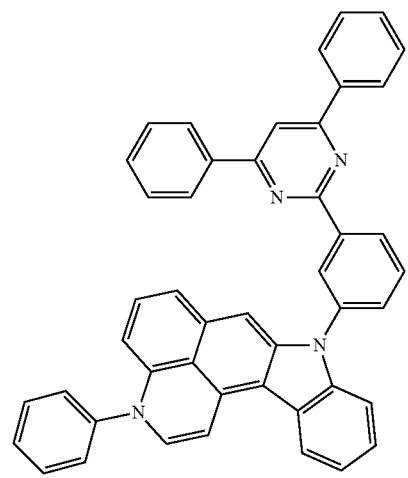
A27
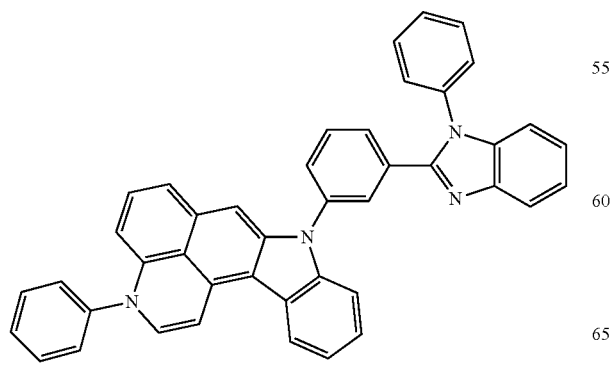
A35
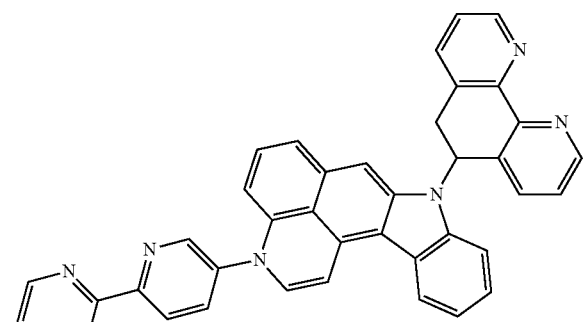
A41
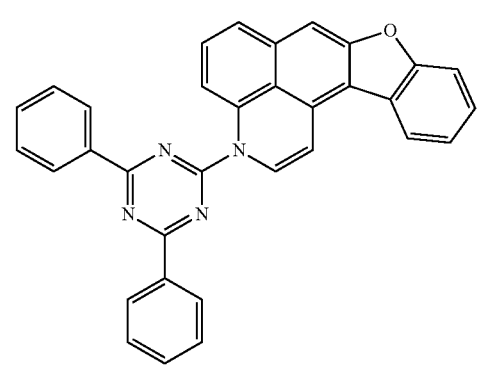
A45
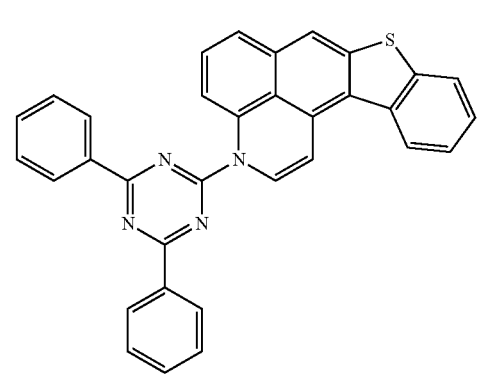
A49
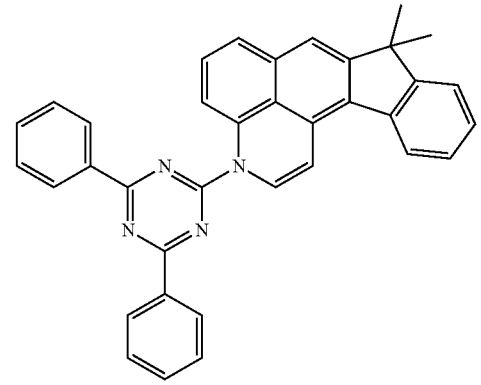

A78
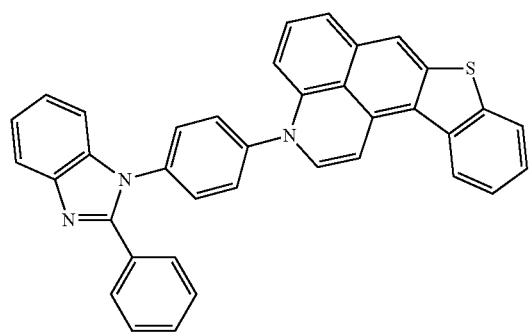
A79
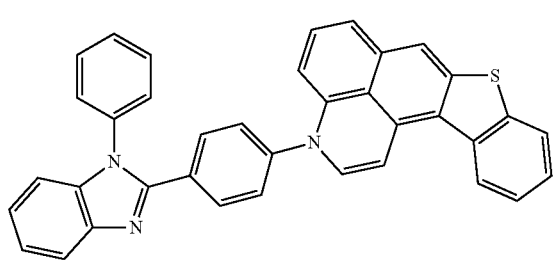
A82
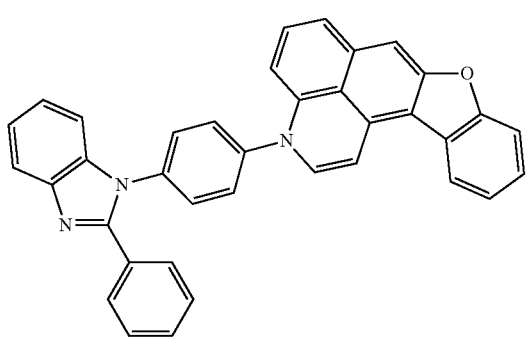
A83
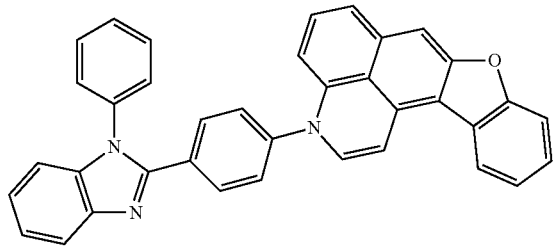
A86
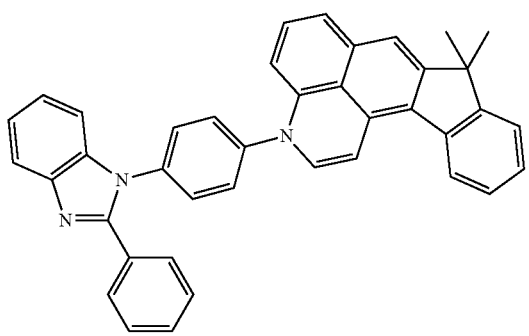
A87
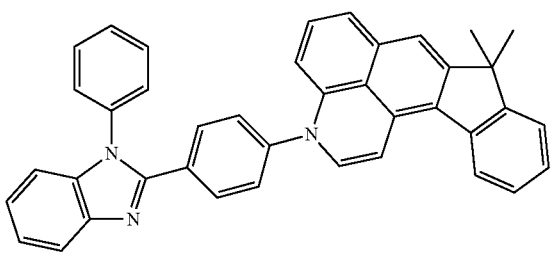
A89
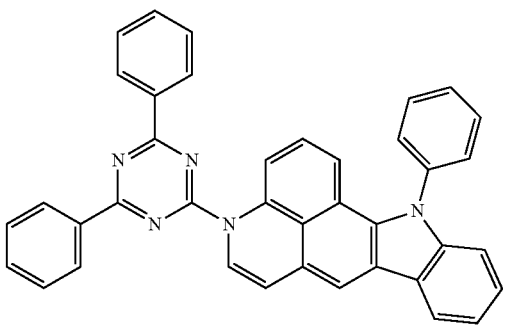
A97
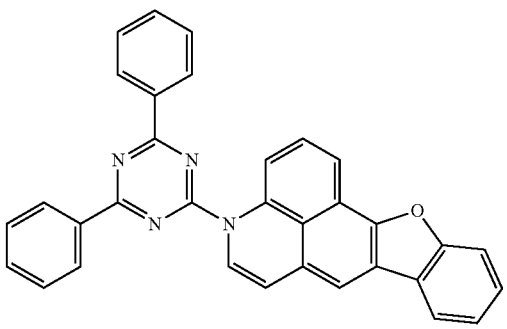
A93
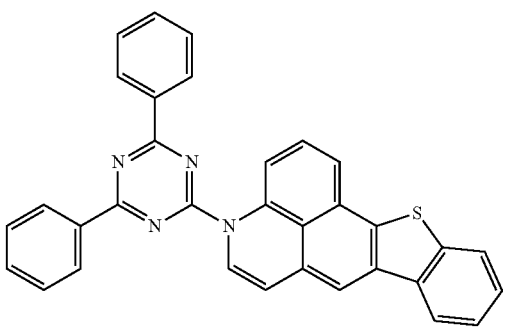

-continued
A101
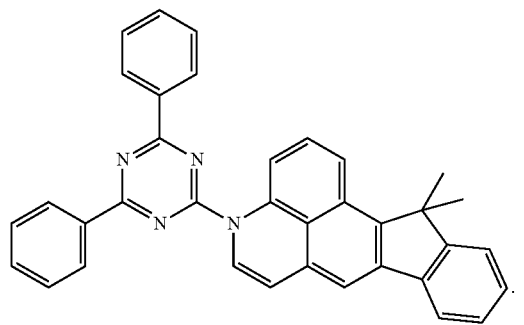
* * * * *